US012655425B2

(12) United States Patent
Hong

(10) Patent No.: US 12,655,425 B2
(45) Date of Patent: Jun. 16, 2026

(54) Nrf-2 DEFICIENT CELLS AND USES THEREOF

(71) Applicant: Pusan National University Industry-University Cooperation Foundation, Busan (KR)

(72) Inventor: Changwan Hong, Busan (KR)

(73) Assignee: Pusan National University Industry-University Cooperation Foundation, Busan (KR)

( * ) Notice: Subject to any disclaimer, the term of this patent is extended or adjusted under 35 U.S.C. 154(b) by 1315 days.

(21) Appl. No.: 17/312,361

(22) PCT Filed: Dec. 9, 2019

(86) PCT No.: PCT/US2019/065227

§ 371 (c)(1),
(2) Date: Jun. 9, 2021

(87) PCT Pub. No.: WO2020/123377

PCT Pub. Date: Jun. 18, 2020

(65) Prior Publication Data

US 2022/0016169 A1 Jan. 20, 2022

(30) Foreign Application Priority Data

Dec. 10, 2018 (KR) ........................ 10-2018-0158428

(51) Int. Cl.
| | |
|---|---|
| *C12N 15/113* | (2010.01) |
| *A61K 40/11* | (2025.01) |
| *A61K 40/31* | (2025.01) |
| *A61K 40/42* | (2025.01) |
| *A61K 45/06* | (2006.01) |
| *A61P 35/00* | (2006.01) |
| *C12N 5/0783* | (2010.01) |
| *C12N 15/85* | (2006.01) |
| *C12Q 1/68* | (2018.01) |

(52) U.S. Cl.
CPC ............ *C12N 15/113* (2013.01); *A61K 40/11* (2025.01); *A61K 40/31* (2025.01); *A61K 40/42* (2025.01); *A61K 40/4211* (2025.01); *A61K 45/06* (2013.01); *A61P 35/00* (2018.01); *C12N 5/0638* (2013.01); *C12N 15/85* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 5,356,802 | A | 10/1994 | Chandrasegaran |
| 5,436,150 | A | 7/1995 | Chandrasegaran |
| 5,487,994 | A | 1/1996 | Chandrasegaran |
| 5,709,874 | A | 1/1998 | Hanson et al. |
| 5,759,542 | A | 6/1998 | Gurewich |
| 5,840,674 | A | 11/1998 | Yatvin et al. |
| 5,900,252 | A | 5/1999 | Calanchi et al. |
| 5,972,366 | A | 10/1999 | Haynes et al. |
| 6,004,534 | A | 12/1999 | Langer et al. |
| 6,039,975 | A | 3/2000 | Shah et al. |
| 6,048,736 | A | 4/2000 | Kosak |
| 6,060,082 | A | 5/2000 | Chen et al. |
| 6,071,495 | A | 6/2000 | Unger et al. |
| 6,120,751 | A | 9/2000 | Unger |
| 6,131,570 | A | 10/2000 | Schuster et al. |
| 6,139,865 | A | 10/2000 | Friend et al. |
| 6,253,872 | B1 | 7/2001 | Neumann |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,453,242 | B1 | 9/2002 | Eisenberg et al. |
| 7,732,417 | B2 | 6/2010 | Beach et al. |
| 8,202,846 | B2 | 6/2012 | Hannon et al. |
| 8,383,599 | B2 | 2/2013 | Hannon et al. |
| 9,782,437 | B2 | 10/2017 | Holmes et al. |

(Continued)

FOREIGN PATENT DOCUMENTS

| | | |
|---|---|---|
| CN | 104877967 A | 9/2015 |
| WO | WO-9712622 A1 | 4/1997 |

(Continued)

OTHER PUBLICATIONS

Tsai et al., Blood vol. 130 (suppl_1):205, Dec. 7, 2017.*
Jo et al., The Journal of Immunology Vool. 196 (suppl 1): 143.15, May 1, 2016.*
Beerli, R.R., et al., "Engineering Polydactyl Zinc-Finger Transcription Factors," Nature Biotechnology 20(2):135-141, Nature America Publishing, United States (Feb. 2002).
Belfort, J., et al., "Homing Endonucleases: Keeping the House in Order," Nucleic Acids Research 25(17):3379-3388, Oxford University Press, England (Sep. 1997).

(Continued)

*Primary Examiner* — Sean McGarry
(74) *Attorney, Agent, or Firm* — Sterne, Kessler, Goldstein & Fox P.L.L.C.

(57) ABSTRACT

The present disclosure relates to T cell anticancer immunotherapy based on modulation of Nrf2 expression, that is, to an Nrf2-targeting immune cell, e.g., T cell, anticancer therapy. The present disclosure allows deep interference with the Nrf2 expression in T cells, thereby solving the problem of immune tolerance shown by cancer cells to T cells; in other words, the effect of anticancer immunotherapy can be improved by targeting Nrf2. The present disclosure can provide an Nrf2-targeting new T cell anticancer immunotherapy and a T cell for the second-generation anticancer immunotherapy. This technology is applicable to the preparation of CAR-T, engineered T, and TIL T cells, and to the treatment of various solid carcinomas, including lymphoma. It can be said to be a new anticancer therapy that improves the therapeutic efficacy effectively.

12 Claims, 20 Drawing Sheets

Specification includes a Sequence Listing.

(56) References Cited

U.S. PATENT DOCUMENTS

| | | | |
|---|---|---|---|
| 10,047,355 | B2 | 8/2018 | Yin et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2006/0063231 | A1 | 3/2006 | Li et al. |
| 2006/0188987 | A1 | 8/2006 | Guschin et al. |
| 2011/0145940 | A1 | 6/2011 | Voytas et al. |
| 2011/0239315 | A1 | 9/2011 | Bonas et al. |
| 2015/0275148 | A1 | 10/2015 | Joiner et al. |

FOREIGN PATENT DOCUMENTS

| | | | |
|---|---|---|---|
| WO | WO-9817815 | A1 | 4/1998 |
| WO | WO-9817816 | A1 | 4/1998 |
| WO | WO-9818934 | A1 | 5/1998 |
| WO | WO-9931251 | A1 | 6/1999 |
| WO | WO-03078619 | A1 | 9/2003 |
| WO | WO-2004031346 | A2 | 4/2004 |
| WO | WO-2005105989 | A1 | 11/2005 |
| WO | WO-2006097784 | A1 | 9/2006 |
| WO | WO-2006097853 | A1 | 9/2006 |
| WO | WO-2006097854 | A1 | 9/2006 |
| WO | WO-2008114262 | A2 | 9/2008 |
| WO | WO-2010079430 | A1 | 7/2010 |
| WO | WO-2013142578 | A1 | 9/2013 |
| WO | WO-2013176772 | A1 | 11/2013 |
| WO | WO-2014065596 | A1 | 5/2014 |
| WO | WO-2014089290 | A1 | 6/2014 |
| WO | WO-2014093622 | A2 | 6/2014 |
| WO | WO-2014099750 | A2 | 6/2014 |
| WO | WO-2014131833 | A1 | 9/2014 |
| WO | WO-2020028400 | A1 | 2/2020 |
| WO | WO-2020123377 | A1 | 6/2020 |

OTHER PUBLICATIONS

Bialk, P., et al., "Functional Gene Knockout of NRF2 Increases Chemosensitivity of Human Lung Cancer A549 Cells in Vitro and in a Xenograft Mouse Model," Molecular Therapy Oncolytics 11:75-89, Cell Press, United States (Oct. 2018).

Bitinaite, J., et al., "Foki Dimerization Is Required for DNA Cleavage," Proceedings of the National Academy of Sciences of the United States of America 95(18):10570-10575, National Academy of Sciences, United States (Sep. 1998).

Capecchi, M.R., et al., "High Efficiency Transformation by Direct Microinjection of DNA Into Cultured Mammalian Cells," Cell 22 (Pt 2):479-488, Cell Press, United States (Nov. 1980).

Chames, P., et al., "In Vivo Selection of Engineered Homing Endonucleases Using Double-strand Break Induced Homologous Recombination," Nucleic Acids Research 33(20):e178, Oxford University Press, England (Nov. 2005).

Chen, C., and Okayama H., "High-efficiency Transformation of Mammalian Cells by Plasmid DNA," Molecular and Cellular Biology 7(8):2745-2752, American Society for Microbiology, United States (Aug. 1987).

Chen, Z., et al., "A Highly Sensitive Selection Method for Directed Evolution of Homing Endonucleases," Nucleic Acids Research 33(18):e154, Oxford University Press, England (Oct. 2005).

Chevalier, B.S., et al., "Design, Activity, and Structure of a Highly Specific Artificial Endonuclease," Molecular Cell 10(4):895-905, Cell Press, Cambridge (Oct. 2002).

Choo, Y., et al., "Advances in zinc finger engineering," Current Opinion in Structural Biology 10(4):411-416, Elsevier Science, England (Aug. 2000).

Christian, M., et al., "Targeting DNA Double Strand Breaks With TAL Effector Nucleases," Genetics 186(2):757-761, Oxford University Press, United Kingdom (Oct. 2010).

Cong, L., et al., "Multiplex Genome Engineering Using CRISPR/Cas Systems," Science 339(6121):819-823, American Association for the Advancement of Science, United States (Feb. 2013).

Epinat, J.C., et al., "A Novel Engineered Meganuclease Induces Homologous Recombination in Yeast and Mammalian Cells," Nucleic Acids Research 31(11):2952-2962, Oxford University Press, England (Jun. 2003).

Fire, A., et al., "Potent and Specific Genetic Interference by Double-stranded Rna in Caenorhabditis Elegans," Nature 391(6669):806-811, Nature Publishing Group, England (Feb. 1998).

Gimble, F.S., et al., "Assessing the Plasticity of DNA Target Site Recognition of the Pi-Scei Homing Endonuclease Using a Bacterial Two-hybrid Selection System," Journal of Molecular Biology 334(5):993-1008, Elsevier, England (Dec. 2003).

Gruen, M., et al., "An in Vivo Selection System for Homing Endonuclease Activity," Nucleic Acids Research 30(7):e29, Oxford University Press, England (Apr. 2002).

Guhan, N., et al., "Structural and Functional Characteristics of Homing Endonucleases," Critical Reviews in Biochemistry and Molecular Biology 38(3):199-248, Informa Healthcare, England (Jan. 2003).

Heiser, W.C., et al., "Optimizing Electroporation Conditions for the Transformation of Mammalian Cells," Methods in Molecular Biology 130:117-134, Humana Press, United States (Jan. 2000).

Hwang, W.Y., et al., "Efficient Genome Editing in Zebrafish Using a CRISPR-Cas System," Nature Biotechnology 31(3):227-229, Nature America Publishing, United States (Jan. 2013).

International Search Report and Written Opinion for International Application No. PCT/US2019/065227, European Patent Office, Netherlands, mailed on Mar. 25, 2020, 17 pages.

Isalan, M., et al., "A Rapid, Generally Applicable Method to Engineer Zinc Fingers Illustrated by Targeting the HIV-1 Promoter," Nature Biotechnology 19:656-660, Nature America Publishing, United States (Jul. 2001).

Jiang, W., et al., "CRISPR-Assisted Editing of Bacterial Genomes," Nature Biotechnology 31(3):233-239, Nature America Publishing, United States (Mar. 2013).

Jinek, M., et al., "A Programmable Dual-RNA-Guided DNA Endonuclease in Adaptive Bacterial Immunity," Science 337(6096):816-821, American Association for the Advancement of Science, United States (Aug. 2012).

Jo, Y., et al., "Nrf2 Expression Is Upregulated in Tumor Infiltrating T Cells and Induces T Cell Anergy," Journal of Immunology 196(1):1-5, American Association of Immunologist, United States (May 2016).

Jurica, M.S., et al., "Homing Endonucleases: Structure, Function and Evolution," Cellular and Molecular Life Sciences 55(10):1304-1326, Springer, Switzerland (Aug. 1999).

Kim, Y.G., et al., "Insertion and Deletion Mutants of Foki Restriction Endonuclease," The Journal of Biological Chemistry 269(50):31978-31982, American Society for Biochemistry and Molecular Biology, United States (Dec. 1994).

Kim, Y.G., et al., "Chimeric Restriction Endonuclease," Proceedings of the National Academy of Sciences of the United States of America 91(3):883-887, National Academy of Sciences, United States (Feb. 1994).

Lewis, W.H., et al., "Parameters Governing the Transfer of the Genes for Thymidine Kinase and Dihydrofolate Reductase Into Mouse Cells Using Metaphase Chromosomes or DNA," Somatic Cell Genetics 6(3):333-347, Plenum, United States (May 1980).

Li, L., et al., "Alteration of the Cleavage Distance of Fok I Restriction Endonuclease by Insertion Mutagenesis," Proceedings of the National Academy of Sciences of the United States of America 90(7):2764-2768, National Academy of Sciences, United States (Apr. 1993).

Li, L., et al., "Functional Domains in Fok I Restriction Endonuclease," Proceedings of the National Academy of Sciences of the United States of America 89(10):4275-4279, National Academy of Sciences, United States (May 1992).

Li, T., et al., "Tal Nucleases (TALNs): Hybrid Proteins Composed of Tal Effectors and Foki DNA-Cleavage Domain," Nucleic Acids Research 39(1):359-372, Oxford University Press, United Kingdom (Jan. 2011).

Liou, G., et al., "Reactive Oxygen Species in Cancer," Free Radical Research 44(5):479-496, Informa Healthcare, England (May 2010).

(56) References Cited

OTHER PUBLICATIONS

Lucas, P., et al., "Rapid Evolution of the DNA-binding Site in LAGLIDADG Homing Endonucleases," Nucleic Acids Research 29(4):960-969, Oxford University Press, England (Feb. 2011).

Mali, P., et al., "RNA-guided human genome engineering via Cas9," Science 339(6121):823-826, American Association for the Advancement of Science, United States (Feb. 2013).

Miller, J., et al., "Repetitive Zinc-Binding Domains in the Protein Transcription Factor IIIA from Xenopus Oocytes," The EMBO Journal 4(6):1609-1614, Wiley Blackwell, England (Jun. 1985).

Miller, J.C., et al., "A TALE Nuclease Architecture for Efficient Genome Editing," Nature Biotechnology 29(2):143-148, Nature America Publishing, United States (Feb. 2011).

Mirzaei, H.R., et al., "Gene-knocked Out Chimeric Antigen Receptor (CAR) T Cells: Tuning up for the Next Generation Cancer Immunotherapy," Cancer Letters 423:95-104, Elsevier Science, Netherlands (Jun. 2018).

Moure, C.M., et al., "Crystal Structure of the Intein Homing Endonuclease PI-Scei Bound to its Recognition Sequence," Nature Structural Biology 9(10):764-770, Nature Publishing, United States (Oct. 2002).

Pabo, C.O., et al., "Design and Selection of Novel Cys2His2 Zinc Finger Proteins," Annual Review of Biochemistry 70:313-340, Annual Reviews, United States (Jul. 2001).

Pandroll, D.M., "The Blockade of Immune Checkpoints in Cancer Immunotherapy," Nature Reviews Cancer 12(4):252-264, Nature Publishing Group, England (Mar. 2012).

Rhodes, D., et al., "Zinc Fingers," Scientific American 268(2):56-59,62-65, Scientific American, United States (Feb. 1993).

Roberts, R.J., et al., "A Nomenclature for Restriction Enzymes, DNA Methyltransferases, Homing Endonucleases and Their Genes," Nucleic Acids Research 31(7):1805-1812, Oxford University Press, England (Apr. 2003).

Roberts, R.J., et al., "Rebase: Restriction Enzymes and Methyltransferases," Nucleic Acids Research 31(1):418-420, Oxford University Press, England (Jan. 2003).

Rosen, L.E., et al., "Homing Endonuclease I-Crei Derivatives With Novel DNA Target Specificities," Nucleic Acids Research 34(17):4791-800, Oxford University Press, England (Oct. 2006).

Rosenberg, S.A., et al., "Durable Complete Responses in Heavily Pretreated Patients With Metastatic Melanoma Using T-Cell Transfer Immunotherapy," Clinical Cancer Research an Official Journal of the American Association for Cancer Research 17(13):4550-4557, The New England Journal of Medicine, United States (Jul. 2011).

Schaffner, W., et al., "Direct Transfer of Cloned Genes From Bacteria to Mammalian Cells," Proceedings of the National Academy of Sciences of the United States of America 77(4):2163-2167, National Academy of Sciences, United States (Apr. 1980).

Scholze, H., et al., "TAL Effector-DNA Specificity," Virulence 1(5):428-432, Taylor & Francis Group, United States (Sep.-Oct. 2010).

Segal, D.J and Barbas 3rd, C.F., "Custom Dna-Binding Proteins Come of Age: Polydactyl Zinc-Finger Proteins," Current Opinion in Biotechnology 12(6):632-637, Elsevier, Netherlands (Dec. 2001).

Seligman, L.M., et al., "Mutations Altering the Cleavage Specificity of a Homing Endonuclease," Nucleic Acids Research, 30(17):3870-3879, Oxford University Press, England (Sep. 2002).

Sharma, P., et al., "Primary, Adaptive, and Acquired Resistance to Cancer Immunotherapy," Cell 168(4):707-723, Cell Press, United States (Feb. 2017).

Smith, J., et al., "A Combinatorial Approach to Create Artificial Homing Endonucleases Cleaving Chosen Sequences," Nucleic Acids Research 34(22):e149, Oxford University Press, England (Dec. 2006).

Stoddard, B.L., et al., "Homing Endonuclease Structure and Function," Quarterly Reviews of Biophysics 38(1):49-95, Cambridge Univ Press, England (Feb. 2005).

Sussman, D., et al., "Isolation and Characterization of New Homing Endonuclease Specificities at Individual Target Site Positions," Journal of Molecular Biology 342(1):31-41, Elsevier, England (Sep. 2004).

Tsai, J., et al., "Nrf2 Is a Critical Mediator of Cd4 T Cell-induced Acute Graft-versus-host Disease," 130(1): 5175-5176, American Society of Hematology, United States (Dec. 2017).

Tsai, J.J., et al., "Nrf2-induced Acute Graft-versus-host Disease in Mice," Blood 132(26):2763-2774, American Association of Hematologists, United States (Dec. 2018).

Wang, J., et al., "Nrf2 Suppresses the Function of Dendritic Cells to Facilitate the Immune Escape of Glioma Cells," Experimental Cell Research 360(2):66-73, Academic Press, United States (Nov. 2017).

Zagorski, J.W., et al., "Nrf2-Dependent and -Independent Effects of tert-Butylhydroquinone, CDDO-Im, and H2O2 in Human Jurkat T Cells as Determined by CRISPR/Cas9 Gene Editing," The Journal of pharmacology and experimental therapeutics 361(2):259-267, Elsevier, Netherlands (May 2017).

* cited by examiner

Calculated tumor volume

FIG. 13B

Calculated Tumor Volume(mm3)

FIG. 13A anti-CD3 stimulation $H_2O_2$ shGFP/CAR-T

IFNγ 10.2 shNRF2/CAR-T

IFNγ 69.3

IFNγ

Nrf2

Nrf2 mRNA expression mock    shGFP    shNRF2

SEQUENCE LISTING

<160> NUMBER OF SEQ ID NOS: 6

<210> SEQ ID NO 1
<211> LENGTH: 605
<212> TYPE: PRT
<213> ORGANISM: Homo sapiens

<400> SEQUENCE: 1

```
Met Met Asp Leu Glu Leu Pro Pro Pro Gly Leu Pro Ser Gln Gln Asp
1               5                   10                  15

Met Asp Leu Ile Asp Ile Leu Trp Arg Gln Asp Ile Asp Leu Gly Val
                20                  25                  30

Ser Arg Glu Val Phe Asp Phe Ser Gln Arg Arg Lys Glu Tyr Glu Leu
            35                  40                  45

Glu Lys Gln Lys Lys Leu Glu Lys Glu Arg Gln Glu Gln Leu Gln Lys
        50                  55                  60

Glu Gln Glu Lys Ala Phe Phe Ala Gln Leu Gln Leu Asp Glu Glu Thr
65                  70                  75                  80

Gly Glu Phe Leu Pro Ile Gln Pro Ala Gln His Ile Gln Ser Glu Thr
                85                  90                  95

Ser Gly Ser Ala Asn Tyr Ser Gln Val Ala His Ile Pro Lys Ser Asp
                100                 105                 110

Ala Leu Tyr Phe Asp Asp Cys Met Gln Leu Leu Ala Gln Thr Phe Pro
            115                 120                 125

Phe Val Asp Asp Asn Glu Val Ser Ser Ala Thr Phe Gln Ser Leu Val
            130                 135                 140

Pro Asp Ile Pro Gly His Ile Glu Ser Pro Val Phe Ile Ala Thr Asn
145                 150                 155                 160

Gln Ala Gln Ser Pro Glu Thr Ser Val Ala Gln Val Ala Pro Val Asp
                165                 170                 175

Leu Asp Gly Met Gln Gln Asp Ile Glu Gln Val Trp Glu Glu Leu Leu
                180                 185                 190

Ser Ile Pro Glu Leu Gln Cys Leu Asn Ile Glu Asn Asp Lys Leu Val
            195                 200                 205

Glu Thr Thr Met Val Pro Ser Pro Glu Ala Lys Leu Thr Glu Val Asp
        210                 215                 220

Asn Tyr His Phe Tyr Ser Ser Ile Pro Ser Met Glu Lys Glu Val Gly
225                 230                 235                 240

Asn Cys Ser Pro His Phe Leu Asn Ala Phe Glu Asp Ser Phe Ser Ser
                245                 250                 255

Ile Leu Ser Thr Glu Asp Pro Asn Gln Leu Thr Val Asn Ser Leu Asn
                260                 265                 270

Ser Asp Ala Thr Val Asn Thr Asp Phe Gly Asp Glu Phe Tyr Ser Ala
        275                 280                 285

Phe Ile Ala Glu Pro Ser Ile Ser Asn Ser Met Pro Ser Pro Ala Thr
        290                 295                 300

Leu Ser His Ser Leu Ser Glu Leu Leu Asn Gly Pro Ile Asp Val Ser
305                 310                 315                 320

Asp Leu Ser Leu Cys Lys Ala Phe Asn Gln Asn His Pro Glu Ser Thr
                325                 330                 335
```

```
Ala Glu Phe Asn Asp Ser Asp Ser Gly Ile Ser Leu Asn Thr Ser Pro
            340                 345                 350

Ser Val Ala Ser Pro Glu His Ser Val Glu Ser Ser Ser Tyr Gly Asp
            355                 360                 365

Thr Leu Leu Gly Leu Ser Asp Ser Glu Val Glu Glu Leu Asp Ser Ala
        370                 375                 380

Pro Gly Ser Val Lys Gln Asn Gly Pro Lys Thr Pro Val His Ser Ser
385                 390                 395                 400

Gly Asp Met Val Gln Pro Leu Ser Pro Ser Gln Gly Gln Ser Thr His
                405                 410                 415

Val His Asp Ala Gln Cys Glu Asn Thr Pro Glu Lys Glu Leu Pro Val
            420                 425                 430

Ser Pro Gly His Arg Lys Thr Pro Phe Thr Lys Asp Lys His Ser Ser
            435                 440                 445

Arg Leu Glu Ala His Leu Thr Arg Asp Glu Leu Arg Ala Lys Ala Leu
        450                 455                 460

His Ile Pro Phe Pro Val Glu Lys Ile Ile Asn Leu Pro Val Val Asp
465                 470                 475                 480

Phe Asn Glu Met Met Ser Lys Glu Gln Phe Asn Glu Ala Gln Leu Ala
                485                 490                 495

Leu Ile Arg Asp Ile Arg Arg Arg Gly Lys Asn Lys Val Ala Ala Gln
            500                 505                 510

Asn Cys Arg Lys Arg Lys Leu Glu Asn Ile Val Glu Leu Glu Gln Asp
            515                 520                 525

Leu Asp His Leu Lys Asp Glu Lys Glu Lys Leu Leu Lys Glu Lys Gly
        530                 535                 540

Glu Asn Asp Lys Ser Leu His Leu Leu Lys Lys Gln Leu Ser Thr Leu
545                 550                 555                 560

Tyr Leu Glu Val Phe Ser Met Leu Arg Asp Glu Asp Gly Lys Pro Tyr
                565                 570                 575

Ser Pro Ser Glu Tyr Ser Leu Gln Gln Thr Arg Asp Gly Asn Val Phe
            580                 585                 590

Leu Val Pro Lys Ser Lys Lys Pro Asp Val Lys Lys Asn
        595                 600                 605

<210> SEQ ID NO 2
<211> LENGTH: 589
<212> TYPE: PRT
<213> ORGANISM: Homo sapiens

<400> SEQUENCE: 2

Met Asp Leu Ile Asp Ile Leu Trp Arg Gln Asp Ile Asp Leu Gly Val
1               5                   10                  15

Ser Arg Glu Val Phe Asp Phe Ser Gln Arg Arg Lys Glu Tyr Glu Leu
                20                  25                  30

Glu Lys Gln Lys Lys Leu Glu Lys Glu Arg Gln Glu Gln Leu Gln Lys
            35                  40                  45

Glu Gln Glu Lys Ala Phe Phe Ala Gln Leu Gln Leu Asp Glu Glu Thr
        50                  55                  60

Gly Glu Phe Leu Pro Ile Gln Pro Ala Gln His Ile Gln Ser Glu Thr
65                  70                  75                  80

Ser Gly Ser Ala Asn Tyr Ser Gln Val Ala His Ile Pro Lys Ser Asp
                85                  90                  95

Ala Leu Tyr Phe Asp Asp Cys Met Gln Leu Leu Ala Gln Thr Phe Pro
                100                 105                 110
```

```
Phe Val Asp Asp Asn Glu Val Ser Ser Ala Thr Phe Gln Ser Leu Val
        115                 120                 125

Pro Asp Ile Pro Gly His Ile Glu Ser Pro Val Phe Ile Ala Thr Asn
    130                 135                 140

Gln Ala Gln Ser Pro Glu Thr Ser Val Ala Gln Val Ala Pro Val Asp
145                 150                 155                 160

Leu Asp Gly Met Gln Gln Asp Ile Glu Gln Val Trp Glu Glu Leu Leu
                165                 170                 175

Ser Ile Pro Glu Leu Gln Cys Leu Asn Ile Glu Asn Asp Lys Leu Val
            180                 185                 190

Glu Thr Thr Met Val Pro Ser Pro Glu Ala Lys Leu Thr Glu Val Asp
        195                 200                 205

Asn Tyr His Phe Tyr Ser Ser Ile Pro Ser Met Glu Lys Glu Val Gly
    210                 215                 220

Asn Cys Ser Pro His Phe Leu Asn Ala Phe Glu Asp Ser Phe Ser Ser
225                 230                 235                 240

Ile Leu Ser Thr Glu Asp Pro Asn Gln Leu Thr Val Asn Ser Leu Asn
                245                 250                 255

Ser Asp Ala Thr Val Asn Thr Asp Phe Gly Asp Glu Phe Tyr Ser Ala
            260                 265                 270

Phe Ile Ala Glu Pro Ser Ile Ser Asn Ser Met Pro Ser Pro Ala Thr
            275                 280                 285

Leu Ser His Ser Leu Ser Glu Leu Leu Asn Gly Pro Ile Asp Val Ser
    290                 295                 300

Asp Leu Ser Leu Cys Lys Ala Phe Asn Gln Asn His Pro Glu Ser Thr
305                 310                 315                 320

Ala Glu Phe Asn Asp Ser Asp Ser Gly Ile Ser Leu Asn Thr Ser Pro
                325                 330                 335

Ser Val Ala Ser Pro Glu His Ser Val Glu Ser Ser Ser Tyr Gly Asp
            340                 345                 350

Thr Leu Leu Gly Leu Ser Asp Ser Glu Val Glu Glu Leu Asp Ser Ala
        355                 360                 365

Pro Gly Ser Val Lys Gln Asn Gly Pro Lys Thr Pro Val His Ser Ser
    370                 375                 380

Gly Asp Met Val Gln Pro Leu Ser Pro Ser Gln Gly Gln Ser Thr His
385                 390                 395                 400

Val His Asp Ala Gln Cys Glu Asn Thr Pro Glu Lys Glu Leu Pro Val
                405                 410                 415

Ser Pro Gly His Arg Lys Thr Pro Phe Thr Lys Asp Lys His Ser Ser
            420                 425                 430

Arg Leu Glu Ala His Leu Thr Arg Asp Glu Leu Arg Ala Lys Ala Leu
        435                 440                 445

His Ile Pro Phe Pro Val Glu Lys Ile Ile Asn Leu Pro Val Val Asp
    450                 455                 460

Phe Asn Glu Met Met Ser Lys Glu Gln Phe Asn Glu Ala Gln Leu Ala
465                 470                 475                 480

Leu Ile Arg Asp Ile Arg Arg Arg Gly Lys Asn Lys Val Ala Ala Gln
                485                 490                 495

Asn Cys Arg Lys Arg Lys Leu Glu Asn Ile Val Glu Leu Glu Gln Asp
            500                 505                 510

Leu Asp His Leu Lys Asp Glu Lys Glu Lys Leu Leu Lys Glu Lys Gly
        515                 520                 525
```

-continued

```
Glu Asn Asp Lys Ser Leu His Leu Leu Lys Lys Gln Leu Ser Thr Leu
    530                 535                 540

Tyr Leu Glu Val Phe Ser Met Leu Arg Asp Glu Asp Gly Lys Pro Tyr
545                 550                 555                 560

Ser Pro Ser Glu Tyr Ser Leu Gln Gln Thr Arg Asp Gly Asn Val Phe
                565                 570                 575

Leu Val Pro Lys Ser Lys Lys Pro Asp Val Lys Lys Asn
                580                 585

<210> SEQ ID NO 3
<211> LENGTH: 582
<212> TYPE: PRT
<213> ORGANISM: Homo sapiens

<400> SEQUENCE: 3

Met Asp Leu Ile Asp Ile Leu Trp Arg Gln Asp Ile Asp Leu Gly Val
1               5                   10                  15

Ser Arg Glu Val Phe Asp Phe Ser Gln Arg Arg Lys Glu Tyr Glu Leu
                20                  25                  30

Glu Lys Gln Lys Lys Leu Glu Lys Glu Arg Gln Glu Gln Leu Gln Lys
        35                  40                  45

Glu Gln Glu Lys Ala Phe Phe Ala Gln Leu Gln Leu Asp Glu Glu Thr
    50                  55                  60

Gly Glu Phe Leu Pro Ile Gln Pro Ala Gln His Ile Gln Ser Glu Thr
65                  70                  75                  80

Ser Gly Ser Ala Asn Tyr Ser Gln Val Ala His Ile Pro Lys Ser Asp
                85                  90                  95

Ala Leu Tyr Phe Asp Asp Cys Met Gln Leu Leu Ala Gln Thr Phe Pro
                100                 105                 110

Phe Val Asp Asp Asn Glu Ser Leu Val Pro Asp Ile Pro Gly His Ile
                115                 120                 125

Glu Ser Pro Val Phe Ile Ala Thr Asn Gln Ala Gln Ser Pro Glu Thr
    130                 135                 140

Ser Val Ala Gln Val Ala Pro Val Asp Leu Asp Gly Met Gln Gln Asp
145                 150                 155                 160

Ile Glu Gln Val Trp Glu Glu Leu Leu Ser Ile Pro Glu Leu Gln Cys
                165                 170                 175

Leu Asn Ile Glu Asn Asp Lys Leu Val Glu Thr Thr Met Val Pro Ser
                180                 185                 190

Pro Glu Ala Lys Leu Thr Glu Val Asp Asn Tyr His Phe Tyr Ser Ser
                195                 200                 205

Ile Pro Ser Met Glu Lys Glu Val Gly Asn Cys Ser Pro His Phe Leu
    210                 215                 220

Asn Ala Phe Glu Asp Ser Phe Ser Ser Ile Leu Ser Thr Glu Asp Pro
225                 230                 235                 240

Asn Gln Leu Thr Val Asn Ser Leu Asn Ser Asp Ala Thr Val Asn Thr
                245                 250                 255

Asp Phe Gly Asp Glu Phe Tyr Ser Ala Phe Ile Ala Glu Pro Ser Ile
                260                 265                 270

Ser Asn Ser Met Pro Ser Pro Ala Thr Leu Ser His Ser Leu Ser Glu
                275                 280                 285

Leu Leu Asn Gly Pro Ile Asp Val Ser Asp Leu Ser Leu Cys Lys Ala
    290                 295                 300

Phe Asn Gln Asn His Pro Glu Ser Thr Ala Glu Phe Asn Asp Ser Asp
305                 310                 315                 320
```

```
Ser Gly Ile Ser Leu Asn Thr Ser Pro Ser Val Ala Ser Pro Glu His
            325                 330                 335

Ser Val Glu Ser Ser Ser Tyr Gly Asp Thr Leu Leu Gly Leu Ser Asp
            340                 345                 350

Ser Glu Val Glu Glu Leu Asp Ser Ala Pro Gly Ser Val Lys Gln Asn
            355                 360                 365

Gly Pro Lys Thr Pro Val His Ser Ser Gly Asp Met Val Gln Pro Leu
    370                 375                 380

Ser Pro Ser Gln Gly Gln Ser Thr His Val His Asp Ala Gln Cys Glu
385                 390                 395                 400

Asn Thr Pro Glu Lys Glu Leu Pro Val Ser Pro Gly His Arg Lys Thr
                405                 410                 415

Pro Phe Thr Lys Asp Lys His Ser Ser Arg Leu Glu Ala His Leu Thr
            420                 425                 430

Arg Asp Glu Leu Arg Ala Lys Ala Leu His Ile Pro Phe Pro Val Glu
            435                 440                 445

Lys Ile Ile Asn Leu Pro Val Val Asp Phe Asn Glu Met Met Ser Lys
    450                 455                 460

Glu Gln Phe Asn Glu Ala Gln Leu Ala Leu Ile Arg Asp Ile Arg Arg
465                 470                 475                 480

Arg Gly Lys Asn Lys Val Ala Ala Gln Asn Cys Arg Lys Arg Lys Leu
                485                 490                 495

Glu Asn Ile Val Glu Leu Glu Gln Asp Leu Asp His Leu Lys Asp Glu
            500                 505                 510

Lys Glu Lys Leu Leu Lys Glu Lys Gly Glu Asn Asp Lys Ser Leu His
            515                 520                 525

Leu Leu Lys Lys Gln Leu Ser Thr Leu Tyr Leu Glu Val Phe Ser Met
    530                 535                 540

Leu Arg Asp Glu Asp Gly Lys Pro Tyr Ser Pro Ser Glu Tyr Ser Leu
545                 550                 555                 560

Gln Gln Thr Arg Asp Gly Asn Val Phe Leu Val Pro Lys Ser Lys Lys
                565                 570                 575

Pro Asp Val Lys Lys Asn
            580
```

```
<210> SEQ ID NO 4
<211> LENGTH: 2446
<212> TYPE: DNA
<213> ORGANISM: Homo sapiens

<400> SEQUENCE: 4
gattaccgag tgccggggag cccggaggag ccgccgacgc agccgccacc gccgccgccg      60
ccgccaccag agccgccctg tccgcgccgc gcctcggcag ccggaacagg gccgccgtcg     120
gggagcccca acacacggtc cacagctcat catgatggac ttggagctgc gccgccgggg     180
actcccgtcc cagcaggaca tggatttgat tgacatactt tggaggcaag atatagatct     240
tggagtaagt cgagaagtat ttgacttcag tcagcgacgg aaagagtatg agctggaaaa     300
acagaaaaaa cttgaaaagg aaagacaaga acaactccaa aaggagcaag agaaagcctt     360
tttcgctcag ttacaactag atgaagagac aggtgaattt ctcccaattc agccagccca     420
gcacatccag tcagaaacca gtggatctgc caactactcc caggttgccc acattcccaa     480
atcagatgct ttgtactttg atgactgcat gcagcttttg cgcagacat  tcccgtttgt     540 agatgacaat gaggtttctt cggctacgtt tcagtcactt gttcctgata ttcccggtca     600
```

-continued

```
catcgagagc ccagtcttca ttgctactaa tcaggctcag tcacctgaaa cttctgttgc     660
tcaggtagcc cctgttgatt tagacggtat gcaacaggac attgagcaag tttgggagga     720
gctattatcc attcctgagt tacagtgtct taatattgaa aatgacaagc tggttgagac     780
taccatggtt ccaagtccag aagccaaact gacagaagtt gacaattatc atttttactc     840
atctataccc tcaatggaaa aagaagtagg taactgtagt ccacattttc ttaatgcttt     900
tgaggattcc ttcagcagca tcctctccac agaagacccc aaccagttga cagtgaactc     960
attaaattca gatgccacag tcaacacaga ttttggtgat gaattttatt ctgctttcat    1020
agctgagccc agtatcagca acagcatgcc ctcacctgct actttaagcc attcactctc    1080
tgaacttcta aatgggccca ttgatgtttc tgatctatca ctttgcaaag ctttcaacca    1140
aaaccaccct gaaagcacag cagaattcaa tgattctgac tccggcattt cactaaacac    1200
aagtcccagt gtggcatcac cagaacactc agtggaatct tccagctatg gagacacact    1260
acttggcctc agtgattctg aagtggaaga gctagatagt gcccctggaa gtgtcaaaca    1320
gaatggtcct aaaacaccag tacattcttc tgggggatatg gtacaaccct tgtcaccatc    1380
tcaggggcag agcactcacg tgcatgatgc ccaatgtgag aacacaccag agaaagaatt    1440
gcctgtaagt cctggtcatc ggaaaacccc attcacaaaa gacaaacatt caagccgctt    1500
ggaggctcat ctcacaagag atgaacttag ggcaaaagct ctccatatcc cattccctgt    1560
agaaaaaatc attaacctcc ctgttgttga cttcaacgaa atgatgtcca aagagcagtt    1620
caatgaagct caacttgcat taattcggga tatacgtagg aggggtaaga ataaagtggc    1680
tgctcagaat tgcagaaaaa gaaaactgga aaatatagta gaactagagc aagatttaga    1740
tcatttgaaa gatgaaaaag aaaaaattgct caaagaaaaa ggagaaaatg acaaaagcct    1800
tcacctactg aaaaaacaac tcagcacctt atatctcgaa gttttcagca tgctacgtga    1860
tgaagatgga aaaccttatt ctcctagtga atactccctg cagcaaacaa gagatggcaa    1920
tgttttcctt gttcccaaaa gtaagaagcc agatgttaag aaaaactaga tttaggagga    1980 tttgacctttt tctgagctag ttttttttgta ctattatact aaaagctcct actgtgatgt    2040
gaaatgctca tactttataa gtaattctat gcaaaatcat agccaaaact agtatagaaa    2100
ataatacgaa actttaaaaa gcattggagt gtcagtatgt tgaatcagta gtttcacttt    2160
aactgtaaac aatttcttag gacaccattt gggctagttt ctgtgtaagt gtaaatacta    2220
caaaaactta tttatactgt tcttatgtca tttgttatat tcatagattt atatgatgat    2280
atgacatctg gctaaaaaga aattattgca aaactaacca ctatgtactt ttttataaat    2340
actgtatgga caaaaaatgg cattttttat attaaattgt ttagctctgg caaaaaaaaa    2400
aaattttaag agctggtact aataaaggat tattatgact gttaaa                   2446
```

<210> SEQ ID NO 5
<211> LENGTH: 2862
<212> TYPE: DNA
<213> ORGANISM: Homo sapiens

<400> SEQUENCE: 5

```
ggcccttccg gggctgcgcg gctcccccgc ctcggtgccg gcaaaaatgt gcctagtcac     60
ggggccgctc tcgggggaac tgaggtcgcc ttcgggctgg gacccggagc cccttcgccg    120
cgccccaaga cctccttgag tgcgggctgc gacgcgctca ccccgctggg ccgtctgtgg    180
gcgcggcttt gcgaagtcat ccatctctcg gatcactctc tggcagcctt gagctctctt    240
```

-continued

```
gaaagcccag cccccgggacg agggaggagc gccttaagtg cccagcgggc tcagaagccc      300
cgacgtgtgg cggctgagcc gggccccgcg cactttctcg gccggggagg ggttcgggct      360
cgggcacccg gagttggccc ctcgtaacgc cgcgggaaag tgcgggcgag ggcagtggac      420
tctgaggccg gagtcggcgg cacccggggc ttctagttcg gacgcggtgc ccctggtgg      480 cgctcaccgc gcgcgtggcc ttggcttccg tgacagcgct cggttggccg tcacagcagc      540
cctcggttgg cccttcctg ctttatagcg tgcaaacctc gccgcgccag ggccaaggga      600
caggacatgg atttgattga catactttgg aggcaagata tagatcttgg agtaagtcga      660
gaagtatttg acttcagtca gcgacggaaa gagtatgagc tggaaaaaca gaaaaaactt      720
gaaaaggaaa gacaagaaca actccaaaag gagcaagaga aagccttttt cgctcagtta      780
caactagatg aagagacagg tgaatttctc ccaattcagc cagcccagca catccagtca      840
gaaaccagtg gatctgccaa ctactcccag gttgcccaca ttcccaaatc agatgctttg      900
tactttgatg actgcatgca gcttttggcg cagacattcc cgtttgtaga tgacaatgag      960
gtttcttcgg ctacgtttca gtcacttgtt cctgatattc ccggtcacat cgagagccca     1020
gtcttcattg ctactaatca ggctcagtca cctgaaactt ctgttgctca ggtagcccct     1080
gttgatttag acggtatgca acaggacatt gagcaagttt gggaggagct attatccatt     1140
cctgagttac agtgtcttaa tattgaaaat gacaagctgg ttgagactac catggttcca     1200
agtccagaag ccaaactgac agaagttgac aattatcatt tttactcatc tataccctca     1260
atggaaaaag aagtaggtaa ctgtagtcca cattttctta atgcttttga ggattccttc     1320
agcagcatcc tctccacaga agaccccaac cagttgacag tgaactcatt aaattcagat     1380
gccacagtca acacagattt tggtgatgaa ttttattctg ctttcatagc tgagcccagt     1440
atcagcaaca gcatgcccct acctgctact ttaagccatt cactctctga acttctaaat     1500
gggcccattg atgtttctga tctatcactt tgcaaagctt tcaaccaaaa ccaccctgaa     1560
agcacagcag aattcaatga ttctgactcc ggcatttcac taaacacaag tcccagtgtg     1620
gcatcaccag aacactcagt ggaatcttcc agctatggag acacactact tggcctcagt     1680
gattctgaag tggaagagct agatagtgcc cctggaagtg tcaaacagaa tggtcctaaa     1740
acaccagtac attcttctgg ggatatggta caacccttgt caccatctca ggggcagagc     1800
actcacgtgc atgatgccca atgtgagaac acaccagaga aagaattgcc tgtaagtcct     1860
ggtcatcgga aaaccccatt cacaaaagac aaacattcaa gccgcttgga ggctcatctc     1920
acaagagatg aacttagggc aaaagctctc catatcccat tccctgtaga aaaaatcatt     1980
aacctccctg ttgttgactt caacgaaatg atgtccaaag agcagttcaa tgaagctcaa     2040
cttgcattaa ttcgggatat acgtaggagg ggtaagaata aagtggctgc tcagaattgc     2100
agaaaaagaa aactggaaaa tatagtagaa ctagagcaag atttagatca tttgaaagat     2160
gaaaaagaaa aattgctcaa agaaaaagga gaaaatgaca aaagccttca cctactgaaa     2220
aaacaactca gcaccttata tctcgaagtt ttcagcatgc tacgtgatga agatggaaaa     2280
ccttattctc ctagtgaata ctccctgcag caaacaagag atggcaatgt tttccttgtt     2340
cccaaaagta agaagccaga tgttaagaaa aactagattt aggaggattt gaccttttct     2400
gagctagttt ttttgtacta ttatactaaa agctcctact gtgatgtgaa atgctcatac     2460
tttataagta attctatgca aaatcatagc caaaactagt atagaaaata atacgaaact     2520
ttaaaaagca ttggagtgtc agtatgttga atcagtagtt tcactttaac tgtaaacaat     2580
ttcttaggac accatttggg ctagtttctg tgtaagtgta aatactacaa aaacttatttt    2640
```

```
atactgttct tatgtcattt gttatattca tagatttata tgatgatatg acatctggct   2700
aaaaagaaat tattgcaaaa ctaaccacta tgtacttttt tataaatact gtatggacaa   2760
aaaatggcat tttttatatt aaattgttta gctctggcaa aaaaaaaaaa ttttaagagc   2820
tggtactaat aaaggattat tatgactgtt aaattattaa aa                      2862

<210> SEQ ID NO 6
<211> LENGTH: 2967
<212> TYPE: DNA
<213> ORGANISM: Homo sapiens

<400> SEQUENCE: 6
ggcccttccg gggctgcgcg gctcccccgc ctcggtgccg gcaaaaatgt gcctagtcac     60
ggggccgctc tcgggggaac tgaggtcgcc ttcgggctgg gacccggagc cccttcgccg    120
cgccccaaga cctccttgag tgcgggctgc gacgcgctca ccccgctggg ccgtctgtgg    180
gcgcggcttt gcgaagtcat ccatctctcg gatcactctc tggcagcctt gagctctctt    240
gaaagcccag ccccgggacg agggaggagc gccttaagtg cccagcgggc tcagaagccc    300
cgacgtgtgg cggctgagcc gggcccccgcg cactttctcg gccggggagg ggttcgggct    360
cgggcacccg gagttggccc ctcgtaacgc cgcgggaaag tgcgggcgag ggcagtggac    420
tctgaggccg gagtcggcgg cacccggggc ttctagttcg gacgcggtgc cccctggtgg    480
cgctcaccgc gcgcgtggcc ttggcttccg tgacagcgct cggttggccg tcacagcagc    540
cctcggttgg ccctttcctg ctttatagcg tgcaaacctc gccgcgccag ggccaaggga    600
caggttggag ctgttgatct gttgcgcaat tgctattttc cccagagcgg ctttgtcttt    660
ggatttagcg tttcagaatt gcaattccaa aatgtgtaag acgggatatt ctcttctgtg    720
ctgtcaaggg acatggattt gattgacata cttttggaggc aagatataga tcttggagta    780
agtcgagaag tatttgactt cagtcagcga cggaaagagt atgagctgga aaaacagaaa    840
aaacttgaaa aggaaagaca agaacaactc caaaaggagc aagagaaagc cttttttcgct   900 cagttacaac tagatgaaga gacaggtgaa tttctcccaa ttcagccagc ccagcacatc    960
cagtcagaaa ccagtggatc tgccaactac tcccaggttg cccacattcc caaatcagat   1020
gctttgtact ttgatgactg catgcagctt ttggcgcaga cattcccgtt tgtagatgac   1080
aatgagtcac ttgttcctga tattcccggt cacatcgaga gcccagtctt cattgctact   1140
aatcaggctc agtcacctga aacttctgtt gctcaggtag cccctgttga tttagacggt   1200
atgcaacagg acattgagca agtttgggag gagctattat ccattcctga gttacagtgt   1260
cttaatattg aaaatgacaa gctggttgag actaccatgg ttccaagtcc agaagccaaa   1320
ctgacagaag ttgacaatta tcatttttac tcatctatac cctcaatgga aaaagaagta   1380
ggtaactgta gtccacattt tcttaatgct tttgaggatt ccttcagcag catcctctcc   1440
acagaagacc ccaaccagtt gacagtgaac tcattaaatt cagatgccac agtcaacaca   1500
gattttggtg atgaatttta ttctgctttc atagctgagc ccagtatcag caacagcatg   1560
ccctcacctg ctactttaag ccattcactc tctgaacttc taaatgggcc cattgatgtt   1620
tctgatctat cactttgcaa agctttcaac caaaaccacc ctgaaagcac agcagaattc   1680
aatgattctg actccggcat ttcactaaac acaagtccca gtgtggcatc accagaacac   1740
tcagtggaat cttccagcta tggagacaca ctacttggcc tcagtgattc tgaagtggaa   1800
gagctagata gtgcccctgg aagtgtcaaa cagaatggtc ctaaaacacc agtacattct   1860
```

-continued

```
tctgggata  tggtacaacc  cttgtcacca  tctcaggggc  agagcactca  cgtgcatgat   1920
gcccaatgtg  agaacacacc  agagaaagaa  ttgcctgtaa  gtcctggtca  tcggaaaacc   1980
ccattcacaa  aagacaaaca  ttcaagccgc  ttggaggctc  atctcacaag  agatgaactt   2040
agggcaaaag  ctctccatat  cccattccct  gtagaaaaaa  tcattaacct  ccctgttgtt   2100
gacttcaacg  aaatgatgtc  caaagagcag  ttcaatgaag  ctcaacttgc  attaattcgg   2160
gatatacgta  ggaggggtaa  gaataaagtg  gctgctcaga  attgcagaaa  aagaaaactg   2220
gaaaatatag  tagaactaga  gcaagattta  gatcatttga  aagatgaaaa  agaaaaattg   2280
ctcaaagaaa  aaggagaaaa  tgacaaaagc  cttcacctac  tgaaaaaaca  actcagcacc   2340
ttatatctcg  aagttttcag  catgctacgt  gatgaagatg  gaaaacctta  ttctcctagt   2400
gaatactccc  tgcagcaaac  aagagatggc  aatgttttcc  ttgttcccaa  aagtaagaag   2460
ccagatgtta  agaaaaacta  gatttaggag  gatttgacct  tttctgagct  agtttttttg   2520
tactattata  ctaaaagctc  ctactgtgat  gtgaaatgct  catactttat  aagtaattct   2580
atgcaaaatc  atagccaaaa  ctagtataga  aaataatacg  aaactttaaa  aagcattgga   2640
gtgtcagtat  gttgaatcag  tagtttcact  ttaactgtaa  acaatttctt  aggacaccat   2700
ttgggctagt  ttctgtgtaa  gtgtaaatac  tacaaaaact  tatttatact  gttcttatgt   2760
catttgttat  attcatagat  ttatatgatg  atatgacatc  tggctaaaaa  gaaattattg   2820
caaaactaac  cactatgtac  ttttttataa  atactgtatg  gacaaaaaat  ggcatttttt   2880
atattaaatt  gtttagctct  ggcaaaaaaa  aaaaatttta  agagctggta  ctaataaagg   2940
attattatga  ctgttaaatt  attaaaa                                          2967
```

Nrf-2 DEFICIENT CELLS AND USES THEREOF

CROSS-REFERENCE TO RELATED APPLICATIONS

This PCT application claims the priority benefit of Korean Patent Application No. 10-2018-0158428, filed Dec. 10, 2018, which is herein incorporated by reference in its entirety.

REFERENCE TO SEQUENCE LISTING SUBMITTED ELECTRONICALLY VIA EFS-WEB

The content of the electronically submitted sequence listing in ASCII text file (Name: 4241_010PC01_Seqlisting_ST25.txt; Size: 26,683 bytes; and Date of Creation: Dec. 9, 2019) filed with the application is herein incorporated by reference in its entirety.

FIELD OF THE DISCLOSURE

The present disclosure relates to a cell-based (e.g., T cell) anticancer immunotherapy based on Nrf2 expression. Specifically, the cells provided herein are modified to express reduced levels of Nrf2.

BACKGROUND OF THE DISCLOSURE

Myeloid-derived suppressor cells (MDSCs) in a solid tumor can generate immunosuppressive tumor microenvironment (TME) and then inhibit anti-tumor response of effector T cells through high production of reactive oxygen species (ROS) and/or Reactive Nitrogen Species (RNS). Such an environment allows tumor cells to evade anticancer immune responses and thereby promote the growth and metastasis of cancer cells, which is one of the characteristics of tumorigenesis. Such an environment is known to affect the activity of tumor-infiltrating lymphocytes (TILs), but no relevant study on response factor has been conducted on T cells. The nuclear factor E2 factor related-factor 2 (Nrf2) is one of typical factors responsible to oxidative stress (OS). Although roles of Nrf2 on cancer cells have been actively evaluated and accumulated, the influences of OS and roles of OS-responsible Nrf2 in anti-tumor responses of TILs, specifically cytotoxic CD8+ T cells have not been studied.

Roles of Nrf2 in tumorigenesis is controversial; Many previous studies suggested that canceration might be prevented when Nrf2 is activated, but the other studies have showed that canceration can be induced by abnormal or continuous activation of Nrf2 in the body. Indeed, an overexpression of Nrf2 leads to a decrease in the five-year survival rate and can induce resistance to an anticancer agent. The current problem is that no study has been conducted on Nrf2 in TILs, and that there is an urgent need for conducting relevant studies. Especially, it is necessary to develop an anticancer immunotherapy that involves modulation of Nrf2 expression in cytotoxic CD8+ T cells.

Despite the advances in cancer immunotherapy, patients with certain malignant tumors (e.g., metastatic or refractory solid tumors) continue to have very poor prognosis. Only a subset of such patients actually experience long-term cancer remission, with many patients either not responding or initially responding but eventually developing resistance to the antibodies. Sharma, P., et al., *Cell* 168(4): 707-723

(2017). Therefore, there remains a need for new treatment options with acceptable safety profile and high efficacy in cancer patients.

BRIEF SUMMARY OF THE DISCLOSURE

The inventors of the present disclosure have identified the mechanism of modulating nuclear factor E2 factor related-factor 2 (Nrf2) in cytotoxic CD8+ T cells, and have developed a T cell that inhibits Nrf2 expression and their cytotoxic functions are sustained in immunosuppressive TME. Furthermore, Nrf2 deficient human CAR-T cells are superior to a conventional T cell in production of anti-tumor cytokines, IFNg and Granzyme B.

An objective of the present disclosure is to provide a pharmaceutical component for preventing and treating cancers. In some aspects, the present disclosure provides T cells with reduced or inhibited Nrf2 expression.

The above-mentioned problem can be solved by the present disclosure, namely, by providing a pharmaceutical component for preventing and treating canceration that involves reducing or inhibiting Nrf2 expression in T cells, etc.

The present disclosure relates to an anticancer immunotherapy based on targeting Nrf2 expression in cells (e.g., T cells). A cancer cell can evade monitoring by the immune system, and one of its main mechanisms is getting a T cell into an exhausted state. The present disclosure allows deep interference with the Nrf2 expression in T cells (i.e., reducing the expression of NFE2L2 gene and/or Nrf2 protein in the cells), thereby solving the problem of T cell exhaustion shown by cancer cells. In other words, the present disclosure provides that the effect of anticancer immunotherapy against solid tumor can be improved by targeting Nrf2 expression in cells (e.g., reducing or inhibiting expression of NFE2L2 gene and/or Nrf2 protein), and this is the greatest characteristic of the present disclosure. The present disclosure can provide new T cell anticancer immunotherapy based on modulating Nrf2 expression in cells and a T cell for the second-generation anticancer immunotherapy. This technology is applicable to the preparation of CAR-T, engineered T, and TIL T cells, and to the treatment of various solid tumor, including leukemia. It can be said to be a new anticancer therapy that improves the therapeutic efficacy effectively.

Provided herein is a method of treating a tumor in a subject in need thereof, comprising administering to the subject a modified cell which expresses reduced levels of NFE2L2 gene and/or Nrf2 protein. In some aspects, the expression levels of NFE2L2 gene and/or Nrf2 protein is reduced by at least about 5%, at least about 10%, at least about 20%, at least about 30%, at least about 40%, at least about 50%, at least about 60%, at least about 70%, at least about 80%, at least about 90%, or at least about 100%, compared to a reference cell (e.g., corresponding cell that has not been modified to express lower levels of NFE2L2 gene and/or Nrf2 protein).

In some aspects, administering a modified cell disclosed herein (i.e., expressing reduced levels of NFE2L2 gene and/or Nrf2 protein) reduces a tumor volume in the subject, compared to a reference tumor volume (e.g., tumor volume in the subject prior to the administration and/or tumor volume in a subject that did not receive the administration). In certain aspects, the tumor volume is reduced by at least about 5%, at least about 10%, at least about 20%, at least about 30%, at least about 40%, at least about 50%, at least about 60%, at least about 70%, at least about 80%, at least about 90%, or at least about 100% after the administration compared to the reference tumor volume.

In some aspects, administering a modified cell disclosed herein (i.e., expressing reduced levels of NFE2L2 gene and/or Nrf2 protein) reduces a tumor weight in the subject, compared to a reference tumor weight (e.g., tumor weight in the subject prior to the administration and/or tumor weight in a subject that did not receive the administration). In certain aspects, the tumor weight is reduced by at least about 5%, at least about 10%, at least about 20%, at least about 30%, at least about 40%, at least about 50%, at least about 60%, at least about 70%, at least about 80%, at least about 90%, or at least about 100% after the administration compared to the reference tumor weight.

In some aspects, administering a modified cell disclosed herein (i.e., expressing reduced levels of NFE2L2 gene and/or Nrf2 protein) improves one or more properties of a tumor-infiltrating lymphocyte (TIL) in the subject. In certain aspects, the TIL produces an increased amount of IFN-γ when stimulated with a cognate antigen, compared to a reference TIL (e.g., TIL from a subject that did not receive the administration). In some aspects, the amount of IFN-γ produced is increased by at least about 5%, at least about 10%, at least about 20%, at least about 30%, at least about 40%, at least about 50%, at least about 60%, at least about 70%, at least about 80%, at least about 90%, or at least about 100% or more, compared to the reference TIL. In some aspects, the TIL is a CD8+ TIL. In some aspects, the TIL is a CD4+ TIL.

In some aspects, the modified cell (i.e., expressing reduced levels of NFE2L2 gene and/or Nrf2 protein) exhibits increased resistance to oxidative stress compared to a reference cell (e.g., a corresponding cell that has not been modified to express lower levels of Nrf2 protein). In certain aspects, the resistance to oxidative stress is increased by at least about 5%, at least about 10%, at least about 20%, at least about 30%, at least about 40%, at least about 50%, at least about 60%, at least about 70%, at least about 80%, at least about 90%, or at least about 100% or more, compared to the reference cell. In some aspects, the increased resistance to oxidative stress comprises an ability to proliferate, produce IFN-γ, and/or express granzyme B in the presence of an elevated concentration of a radical oxygen species. In some aspects, the radical oxygen species comprises hydrogen peroxide ($H_2O_2$).

In some aspects, the modified cell which can be administered in a method disclosed herein is an immune cell. In certain aspects, the immune cell comprises a lymphocyte, neutrophil, monocyte, macrophage, dendritic cell, or combinations thereof. In some aspects, the lymphocyte comprises a T cell, tumor-infiltrating lymphocyte (TIL), lymphokine-activated killer cell, natural killer (NK) cell, or combinations thereof. In certain aspects, the lymphocyte is a T cell. In further aspects, the T cell comprises a chimeric antigen receptor (CAR) and/or a T cell receptor (TCR), e.g., engineered TCR.

In some aspects, the tumor which can be treated with a method disclosed herein is derived from a cancer comprising a breast cancer, head and neck cancer, uterine cancer, brain cancer, skin cancer, renal cancer, lung cancer, colorectal cancer, prostate cancer, liver cancer, bladder cancer, kidney cancer, pancreatic cancer, thyroid cancer, esophageal cancer, eye cancer, stomach (gastric) cancer, gastrointestinal cancer, ovarian cancer, carcinoma, sarcoma, leukemia, lymphoma, myeloma, or a combination thereof. In certain aspects, the cancer is a colorectal cancer, skin cancer, lymphoma, lung cancer, or combinations thereof.

In some aspects, a method of treating a tumor disclosed herein comprises administering an additional therapeutic agent to the subject. In certain aspects, the additional therapeutic agent comprises a chemotherapeutic drug, targeted anti-cancer therapy, oncolytic drug, cytotoxic agent, immune-based therapy, cytokine, surgical procedure, radiation procedure, activator of a costimulatory molecule, immune checkpoint inhibitor, a vaccine, a cellular immunotherapy, or any combination thereof.

In some aspects, the additional therapeutic agent is an immune checkpoint inhibitor. In certain aspects, the immune checkpoint inhibitor comprises an anti-PD-1 antibody, anti-PD-L1 antibody, anti-LAG-3 antibody, anti-CTLA-4 antibody, anti-GITR antibody, anti-TIM3 antibody, or any combination thereof.

In some aspects, the additional therapeutic agent and the modified cell are administered concurrently. In other aspects, the additional therapeutic agent and the modified cell are administered sequentially.

In some aspects, a modified cell (i.e., expressing reduced levels of NFE2L2 gene and/or Nrf2 protein) which can be used to treat a tumor in a method disclosed herein is administered parenthetically, intramuscularly, subcutaneously, ophthalmic, intravenously, intraperitoneally, intradermally, intraorbitally, intracerebrally, intracranially, intraspinally, intraventricular, intrathecally, intracisternally, intracapsularly, intratumorally, or any combination thereof.

Present disclosure further provides a method of improving an anti-tumor immune response of a chimeric antigen receptor (CAR)-expressing cell, comprising modifying the cell to express reduced levels of NFE2L2 gene and/or Nrf2 protein, wherein the lower expression of the NFE2L2 gene and/or Nrf2 protein improves the anti-tumor immune response of the cell. In some aspects, the expression level of the NFE2L2 gene and/or Nrf2 protein in the modified cell is reduced by at least about 5%, at least about 10%, at least about 20%, at least about 30%, at least about 40%, at least about 50%, at least about 60%, at least about 70%, at least about 80%, at least about 90%, or at least about 100%, compared to a reference cell (e.g., corresponding cell that has not been modified to express lower levels of NFE2L2 gene and/or Nrf2 protein).

In some aspects, the modified cell produces an increased amount of IFN-γ when stimulated with a cognate antigen, compared to a reference cell (e.g., corresponding cell that has not been modified to express lower levels of the NFE2L2 gene and/or Nrf2 protein). In certain aspects, the amount of IFN-γ produced is increased by at least about 5%, at least about 10%, at least about 20%, at least about 30%, at least about 40%, at least about 50%, at least about 60%, at least about 70%, at least about 80%, at least about 90%, or at least about 100% or more, compared to the reference cell.

In some aspects, the modified cell exhibits increased resistance to oxidative stress compared to a reference cell (e.g., a corresponding cell that has not been modified to express lower levels of Nrf2 protein). In certain aspects, the resistance to oxidative stress is increased by at least about 5%, at least about 10%, at least about 20%, at least about 30%, at least about 40%, at least about 50%, at least about 60%, at least about 70%, at least about 80%, at least about 90%, or at least about 100% or more, compared to the reference cell. In some aspects, the increased resistance to oxidative stress comprises an ability to proliferate, produce IFN-γ, and/or express granzyme B in the presence of an elevated concentration of a radical oxygen species. In certain aspects, the radical oxygen species comprises hydrogen peroxide ($H_2O_2$).

In some aspects, modifying a cell in a method disclosed herein comprises contacting the cell with a gene editing tool that is capable of reducing the expression levels of the NFE2L2 gene and/or Nrf2 protein in the cell. In certain aspects, the gene editing tool comprises a shRNA, siRNA, miRNA, antisense oligonucleotides, CRISPR, zinc finger nuclease, TALEN, meganuclease, restriction endonuclease, or any combination thereof. In some aspects, the gene editing tool is shRNA.

In some aspects, the modified cell (i.e., expressing reduced levels of NFE2L2 gene and/or Nrf2 protein) is an immune cell. In certain aspects, the immune cell comprises a lymphocyte, neutrophil, monocyte, macrophage, dendritic cell, or combinations thereof. In some aspects, the lymphocyte comprises a T cell, tumor-infiltrating lymphocyte (TIL), lymphokine-activated killer cell, natural killer (NK) cell, or combinations thereof. In certain aspects, the lymphocyte is a T cell.

Also provided herein is a method of preparing an immune cell for chimeric antigen receptor engineering comprising contacting the immune cell with a gene editing tool to reduce an expression level of a NFE2L2 gene and/or Nrf2 protein. In some aspects, the expression levels of NFE2L2 gene and/or Nrf2 protein is reduced by at least about 5%, at least about 10%, at least about 20%, at least about 30%, at least about 40%, at least about 50%, at least about 60%, at least about 70%, at least about 80%, at least about 90%, or at least about 100%, compared to a reference cell (e.g., corresponding cell that has not been modified to express lower levels of NFE2L2 gene and/or Nrf2 protein).

In some aspects, the immune cell comprises a lymphocyte, neutrophil, monocyte, macrophage, dendritic cell, or any combination thereof. In certain aspects, the lymphocyte comprises a T cell, a tumor-infiltrating lymphocyte (TIL), a lymphokine-activated killer cell, natural killer (NK) cell, or any combination thereof. In some aspects, the lymphocyte is a T cell.

In some aspects, a gene editing tool which can be used in a method of preparing an immune cell for chimeric antigen receptor engineering comprises a shRNA, siRNA, miRNA, antisense oligonucleotides, CRISPR, zinc finger nuclease, TALEN, meganuclease, restriction endonuclease, or any combination thereof. In certain aspects, the gene editing tool is shRNA.

In some aspects, a method of preparing an immune cell for chimeric antigen receptor engineering disclosed herein further comprises modifying the immune cell to express a chimeric antigen receptor (CAR). In certain aspects, modifying the immune cell to express the CAR comprises contacting the immune cell with a nucleic acid sequence encoding the CAR.

In some aspects, a nucleic acid encoding the gene editing tool is expressed from an expression vector. In certain aspects, the nucleic acid sequence encoding the CAR is expressed from an expression vector. In some aspects, the gene editing tool and the CAR are encoded on separate expression vectors. In other aspects, the gene editing tool and the CAR are encoded on the same expression vector.

Provided herein is a pharmaceutical composition for preventing or treating cancer comprising a T cell with reduced Nrf2 expression. In some aspects, the T cell comprises a chimeric antigen receptor (CAR) and/or a T cell receptor (TCR), e.g., engineered TCR.

Also provided herein is a cell prepared by a method disclosed herein. In certain aspects, the cell comprises a chimeric antigen receptor (CAR) and/or a T cell receptor (TCR), e.g., engineered TCR. In some aspects, the cell is a T cell, tumor-infiltrating lymphocyte (TIL), lymphokine-activated killer cell, NK cell, or any combination thereof.

BRIEF DESCRIPTION OF THE DRAWINGS

FIGS. 8A and 8B show that the improved anti-tumor immune responses observed in the Nrf2−/− animals are T cell mediated. Comparison of tumor growth (FIG. 8A) and tumor weight (FIG. 8B) are provided for the following groups: (i) tumor-bearing wild-type animals that received a control IgG antibody ("WT+IgG" or "open circle"); (ii) tumor-bearing wild-type animals that received an administration of a T cell depleting anti-CD3 antibody ("WT+α-CD3" or "filled circle"); (iii) tumor-bearing Nrf2−/− animals that received a control IgG antibody ("Nrf2−/−+IgG" or "open square"); and (iv) tumor-bearing Nrf2−/− animals that received an administration of a T cell depleting anti-CD3 antibody ("Nrf2−/−+α-CD3" or "closed square").

FIG. 11 provides a comparison of tumor volume in the different animals at various time points post tumor inoculation.

FIGS. 13A and 13B provide a comparison of the anti-tumor immune response in wild-type (open circle), Nrf2-/- (closed square), and Nrf2-transgenic (closed triangle) mice inoculated with MC38 (colorectal) tumor cells. FIG. 13A shows the tumor volume in the different treatment groups at various time points post tumor inoculation. FIG. 13B provides a comparison of tumor volume at day 28 post-tumor inoculation.

In FIG. 14A, OS resistance is measured by the amount of IFN-γ produced by the T cells from the different animals upon TCR stimulation with or without H2O2. FIG. 14B provides a graphical depiction of the flow cytometry data provided in FIG. 14A. In FIG. 14C, OS resistance is measured by expression of Granzyme B. FIG. 14D provides a graphical depiction of the flow cytometry data provided in FIG. 14C. In both FIGS. 14A and 14C, (i) cells shown in the top row were neither TCR stimulated nor exposed to H2O2; (ii) cells shown in the middle row were TCR stimulated but not exposed to H2O2; and (iii) cells shown in the bottom row were both TCR stimulated and exposed to H2O2. In each of the flow plots, the boxed area to the left represent activated T cells (i.e., proliferated upon TCR stimulation) and boxed area to the right represent those T cells that did not proliferate upon TCR stimulation. Proliferation is shown based on CFSE profile.

FIGS. 15A, 15B, and 15C show the generation of a CD19-specific CAR T cell that lacks Nrf2 expression. FIG. 15A provides a schematic of the CD19 CAR construct. FIG. 15B shows the knock down of Nrf2 mRNA expression in the transduced CD19 CAR T cells using shRNA specific to Nrf2 mRNA. FIG. 15C shows the activity of the CD19-specific Nrf2-deficient CART cells to resist OS, as measured by the amount of IFN-γ produced after anti-CD3 stimulation in the presence of H2O2. The data shown on the top is for the control CART cells (i.e., expressing normal levels of Nrf2).

FIGS. 16A, 16B, and 16C show the results of Nrf2 protein expression in human T cells using CRISPR/Cas9 system. FIGS. 16A, 16B, and 16C provide results using three different guide RNAs (gRNAs) targeting Nrf2 gene with Cas9 protein. T7E1 analysis was used to detect the on-target CRISPR/Cas9 editing event on Nrf2 gene. The percentages shown represent the indel mutant rate of individual gRNAs on Nrf2 gene after modification with the Cas9/gRNA complex.

DETAILED DESCRIPTION OF THE DISCLOSURE

Figure 1:
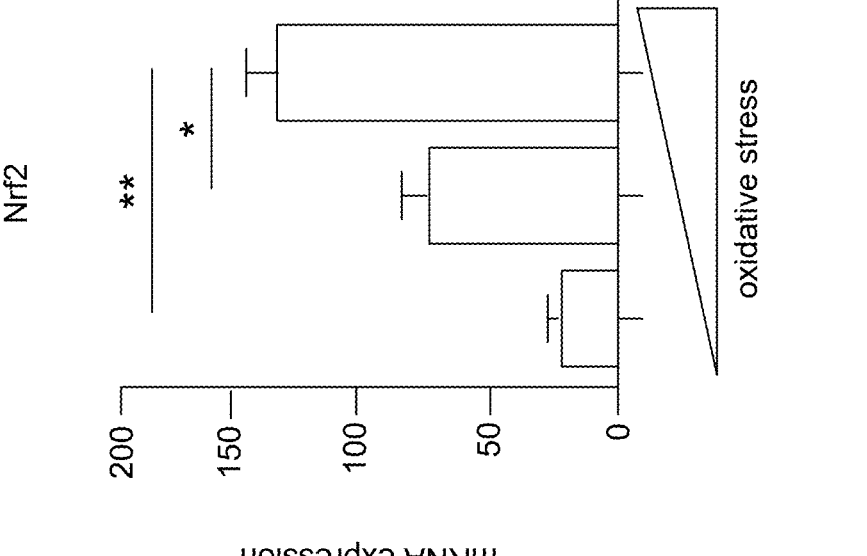
FIG. 1 shows the change in Nrf2 mRNA expression in cytotoxic CD8+ T cells with increase in oxidative stress (represented by increased $H_2O_2$ concentration).

A cancer cell can evade monitoring by the immune system, and one of its main mechanisms is getting a T cell into an exhausted state. The present disclosure allows deep interference with the Nrf2 expression in T cells, thereby solving the problem of immune exhaustion induced by TME to TILs; in other words, the effect of anticancer immunotherapy can be improved by targeting Nrf2, and this is the greatest characteristic of the present disclosure. Therefore, the present disclosure is directed to methods of treating a tumor in a subject in need thereof comprising administering a modified cell that has a reduced expression of NFE2L2 gene and/or Nrf2 protein. In some aspects, the present disclosure is directed to methods of improving anti-tumor efficacy of a CAR or TCR engineering cell. In some aspects, the present disclosure is directed to a method of preventing or inhibiting immune tolerance of an immune cell against tumor.

I. Definitions

In order that the present disclosure can be more readily understood, certain terms are first defined. As used in this application, except as otherwise expressly provided herein, each of the following terms shall have the meaning set forth below. Additional definitions are set forth throughout the application.

Throughout this disclosure, the term "a" or "an" entity refers to one or more of that entity; for example, "an antibody," is understood to represent one or more antibodies. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

As used herein, "administering" refers to the physical introduction of a therapeutic agent or a composition comprising a therapeutic agent to a subject, using any of the various methods and delivery systems known to those skilled in the art. The different routes of administration for a therapeutic agent described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, intratracheal, pulmonary, subcutaneous, subcuticular, intraarticular, subcapsular, subarachnoid, intraventricle, intravitreal, epidural, and intrasternal injection and infusion, as well as in vivo electroporation. Alternatively, a therapeutic agent described herein can be administered via a non-parenteral route, such as a topical, epidermal, or mucosal route of administration, for example, intranasally, orally, vaginally, rectally, sublingually, or topically. Administering can also be performed, for example, once, a plurality of times, and/or over one or more extended periods.

As used herein, the term "antigen" refers to any natural or synthetic immunogenic substance, such as a protein, peptide, or hapten. As used herein, the term "cognate antigen" refers to an antigen which an immune cell (e.g., T cells) recognizes and thereby, induces the activation of the immune cell (e.g., triggering intracellular signals that induce effector functions, such as cytokine production, and/or for proliferation of the cell).

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides. Unless otherwise specified, the terms "protein" and "polypeptide" can be used interchangeably.

The term "nucleic acid molecule," as used herein, is intended to include DNA molecules and RNA molecules. A nucleic acid molecule can be single-stranded or double-stranded, and can be cDNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

A "cancer" refers a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. "Cancer" as used herein refers to primary, metastatic and recurrent cancers.

As used herein, the term "immune response" refers to a biological response within a vertebrate against foreign agents, which response protects the organism against these agents and diseases caused by them. An immune response is mediated by the action of a cell of the immune system (e.g., a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4$^+$ or CD8$^+$ T cell, or the inhibition of a Treg cell. As used herein, the term "T cell" and "T lymphocytes" are interchangeable and refer to any lymphocytes produced or processed by the thymus gland. In some aspects, a T cell is a CD4+ T cell. In some aspects, a T cell is a CD8+ T cell. In some aspects, a T cell is a NKT cell.

As used herein, the term "anti-tumor immune response" refers to an immune response against a tumor antigen.

As used herein, the term "tumor infiltrating lymphocytes" or "TILs" refers to lymphocytes (e.g., effector T cells) that have migrated from the periphery (e.g., from the blood) into a tumor. In some aspects, the tumor infiltrating lymphocytes are CD4+ TILs. In other aspects, the tumor infiltrating lymphocytes are CD8+ TILs.

An increased ability to stimulate an immune response or the immune system, can result from an enhanced agonist activity of T cell costimulatory receptors and/or an enhanced antagonist activity of inhibitory receptors. An increased ability to stimulate an immune response or the immune system can be reflected by a fold increase of the EC50 or maximal level of activity in an assay that measures an immune response, e.g., an assay that measures changes in cytokine or chemokine release, cytolytic activity (determined directly on target cells or indirectly via detecting CD107a or granzymes) and proliferation. The ability to stimulate an immune response or the immune system activity can be enhanced by at least 10%, 30%, 50%, 75%, 2 fold, 3 fold, 5 fold or more.

A "subject" includes any human or nonhuman animal. The term "nonhuman animal" includes, but is not limited to, vertebrates such as nonhuman primates, sheep, dogs, and rodents such as mice, rats and guinea pigs. In some aspects, the subject is a human. The terms "subject" and "patient" are used interchangeably herein.

The term "therapeutically effective amount" or "therapeutically effective dosage" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to solid tumors, an effective amount comprises an amount sufficient to cause a tumor to shrink and/or to decrease the growth rate of the tumor (such as to suppress tumor growth) or to prevent or delay other unwanted cell proliferation. In some aspects, an effective amount is an amount sufficient to delay tumor development. In some aspects, an effective amount is an amount sufficient to prevent or delay tumor recurrence. An effective amount can be administered in one or more administrations. The effective amount of the drug or composition can: (i) reduce the number of cancer cells; (ii) reduce tumor size; (iii) inhibit, retard, slow to some extent and can stop cancer cell infiltration into peripheral organs; (iv) inhibit (i.e., slow to some extent and can stop tumor metastasis; (v) inhibit tumor growth; (vi) prevent or delay occurrence and/or recurrence of tumor; and/or (vii) relieve to some extent one or more of the symptoms associated with the cancer. In some aspects, a "therapeutically effective amount" is the amount of the modified cell herein clinically proven to affect a significant decrease in cancer or slowing of progression (regression) of cancer, such as an advanced solid tumor. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, the term "standard of care" refers to a treatment that is accepted by medical experts as a proper treatment for a certain type of disease and that is widely used by healthcare professionals. The term can be used interchangeable with any of the following terms: "best practice," "standard medical care," and "standard therapy."

By way of example, an "anti-cancer agent" promotes cancer regression in a subject or prevents further tumor growth. In certain aspects, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

As used herein, the term "immune checkpoint inhibitor" refers to molecules that totally or partially reduce, inhibit, interfere with or modulate one or more checkpoint proteins. Checkpoint proteins regulate T-cell activation or function. Numerous checkpoint proteins are known, such as CTLA-4 and its ligands CD80 and CD86; and PD-1 with its ligands PD-L1 and PD-L2. Pardoll, D. M., *Nat Rev Cancer* 12(4): 252-64 (2012). These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies.

As used herein, the term "oxidative stress" refers to the condition characterized by an excess of oxidants and/or a decrease in antioxidant levels. Cellular oxidants can include, but are not limited to, radicals of oxygen (superoxide anion, hydroxyl radical, and/or peroxy radicals); reactive non-radical oxygen species such as, for example, hydrogen peroxide and singlet oxygen; carbon radicals; nitrogen radicals; sulfur radicals; and combinations thereof. In some aspects, the condition of oxidative stress can result in, for example, cellular damage, impaired performance of cells, and/or cell death.

As used herein, the term "modified cell" refers to a cell that differs from a corresponding cell that has not been modified. As will be apparent from the disclosure, modified cells disclosed herein express reduced levels of NFE2L2 gene and/or Nrf2 protein compared to a reference cell (e.g., corresponding cell that has not been modified). In some aspects, a modified cell is produced by introducing a foreign or exogenous nucleic acid into a cell. In certain aspects, the foreign or exogenous nucleic acid can encode a gene editing tool disclosed herein. In other aspects, the foreign or exogenous nucleic acid can encode a chimeric antigen receptor (such as those described herein). A nucleic acid can be introduced into a cell by methods known in the art, such as, for example, electroporation (see, e.g., Heiser W. C. *Transcription Factor Protocols: Methods in Molecular Biology™* 2000; 130: 117-134), chemical (e.g., calcium phosphate or lipid) transfection (see, e.g., Lewis W. H., et al., *Somatic Cell Genet.* 1980 May; 6(3): 333-47; Chen C., et al., *Mol Cell Biol.* 1987 August; 7(8): 2745-2752), fusion with bacterial protoplasts containing recombinant plasmids (see, e.g., Schaffner W. *Proc Natl Acad Sci USA.* 1980 April; 77(4): 2163-7), or microinjection of purified DNA directly into the nucleus of the cell (see, e.g., Capecchi M. R. *Cell.* 1980 November; 22(2 Pt 2): 479-88).

As used herein, the term "elevated concentrations" refers to above-normal levels of a substance (e.g., a reactive oxygen species) compared to appropriate controls (e.g., healthy tissue or cells).

As used herein, the term "reactive oxygen species" refers to highly reactive chemicals, containing oxygen, that react easily with other molecules, resulting in potentially damaging modifications. Reactive oxygen species include, for example, oxygen ions, free radicals and peroxides both inorganic and organic such as hydrogen peroxide, superoxide, hydroxyl radical, lipid hydroperoxidase and singlet oxygen. They are generally very small molecules and are highly reactive due to the presence of unpaired valence shell electrons. Nearly all cancers are associated with elevated concentrations of reactive oxygen species. Liou, G., et al., *Free Radic Res* 44(5): 1-31 (2010).

The term "chimeric antigen receptor" or "CAR," as used herein, refers to a recombinant fusion protein that has an antigen-specific extracellular domain coupled to an intracellular domain that directs the cell to perform a specialized function upon binding of an antigen to the extracellular domain. The terms "artificial T cell receptor," "chimeric T-cell receptor," and "chimeric immunoreceptor" can each be used interchangeably herein with the term "chimeric antigen receptor." Chimeric antigen receptors are distinguished from other antigen binding agents by their ability to both bind MHC-independent antigen and transduce activation signals via their intracellular domain.

The antigen-specific extracellular domain of a chimeric antigen receptor recognizes and specifically binds an antigen, typically a surface-expressed antigen of a malignancy. An antigen-specific extracellular domain specifically binds an antigen when, for example, it binds the antigen with an affinity constant or affinity of interaction ($K_D$) between about 0.1 pM to about 10 for example, about 0.1 pM to about 1 µM or about 0.1 pM to about 100 nM. Methods for determining the affinity of interaction are known in the art. An antigen-specific extracellular domain suitable for use in a CAR of the present disclosure can be any antigen-binding polypeptide, a wide variety of which are known in the art. In some aspects, the antigen-binding domain is a single chain Fv (scFv). Other antibody-based recognition domains (cAb VHH (camelid antibody variable domains) and humanized versions thereof, lgNAR VH (shark antibody variable domains) and humanized versions thereof, sdAb VH (single domain antibody variable domains) and "camelized" antibody variable domains are suitable for use. In some aspects, T cell receptor (TCR) based recognition domains, such as single chain TCR (scTv, single chain two-domain TCR containing V.alpha.V.beta.) are also suitable for use.

A chimeric antigen receptor disclosed herein can also include an intracellular domain that provides an intracellular signal to the cell (expressing the CAR) upon antigen binding to the antigen-specific extracellular domain. In some aspects, the intracellular signaling domain of a CAR is responsible for activation of at least one of the effector functions of the T cell in which the chimeric receptor is expressed.

The term "intracellular domain" refers to the portion of a CAR that transduces the effector function signal upon binding of an antigen to the extracellular domain and directs the T cell to perform a specialized function. Non-limiting examples of suitable intracellular domains include the zeta chain of the T-cell receptor or any of its homologs (e.g., eta, delta, gamma, or epsilon), MB 1 chain, 829, Fc RIII, Fc RI, and combinations of signaling molecules, such as CD3.zeta. and CD28, CD27, 4-1BB, DAP-10, OX40, and combinations thereof, as well as other similar molecules and fragments. Intracellular signaling portions of other members of the families of activating proteins can be used, such as FcγRIII and FcεRI. While usually the entire intracellular domain will be employed, in many cases it will not be necessary to use the entire intracellular polypeptide. To the extent that a truncated portion of the intracellular signaling domain can find use, such truncated portion can be used in place of the intact chain as long as it still transduces the effector function signal. The term intracellular domain is thus meant to include any truncated portion of the intracellular domain sufficient to transduce the effector function signal. Typically, the antigen-specific extracellular domain is linked to the intracellular domain of the chimeric antigen receptor by a transmembrane domain. A transmembrane domain traverses the cell membrane, anchors the CAR to the T cell surface, and connects the extracellular domain to the intracellular signaling domain, thus impacting expression of the CAR on the T cell surface. Chimeric antigen receptors can also further comprise one or more costimulatory domain and/or one or more spacer. A costimulatory domain is derived from the intracellular signaling domains of costimulatory proteins that enhance cytokine production, proliferation, cytotoxicity, and/or persistence in vivo. A "peptide hinge" connects the antigen-specific extracellular domain to the transmembrane domain. The transmembrane domain is fused to the costimulatory domain, optionally a costimulatory domain is fused to a second costimulatory domain, and the costimulatory domain is fused to a signaling domain, not limited to CD3ζ. For example, inclusion of a spacer domain between the antigen-specific extracellular domain and the transmembrane domain, and between multiple scFvs in the case of tandem CAR, can affect flexibility of the antigen-binding domain(s) and thereby CAR function. Suitable transmembrane domains, costimulatory domains, and spacers are known in the art.

As used herein, the term "gene-editing" refers to the process of changing the genetic information present in the genome of a cell. This gene-editing can be performed by manipulating genomic DNA, resulting in a modification of the genetic information. In some aspects, such gene-editing can influence expression of the DNA that has been edited. In other aspects, such gene-editing does not affect the expression of the DNA that has been edited. In some aspects, gene-editing of a modified cell disclosed herein can be done using a gene editing tool described herein. Non-limiting examples of gene editing tools include RNA interference molecules (e.g., shRNA, siRNA, miRNA), antisense oligonucleotides, CRISPR, zinc finger nuclease (ZFN), transcription activator-like effector nuclease (TALEN), meganucleases, restriction endonuclease, or any combination thereof.

As used herein, the terms "ug" and "uM" are used interchangeably with "µg" and "µM," respectively.

Various aspects described herein are described in further detail in the following subsections.

II. Methods of the Disclosure

IIa. Method of Treating

The present disclosure is directed to a method for treating a tumor (or a cancer) in a subject in need thereof, comprising administering to the subject a modified cell which expresses reduced levels of NFE2L2 gene and/or Nrf2 protein. In some aspects, "reduced levels of NFE2L2 gene and/or Nrf2 protein" includes no expression of NFE2L2 gene and/or Nrf2 protein.

The term "Nrf2" or "nuclear factor erythroid 2-related factor 2" refers to a protein that belongs to the family of basic leucine zipper protein transcription factors. Nrf2 is also known as "nuclear factor, erythroid 2 like 2," "nuclear factor erythroid-derived 2-like 2," "HEBP1," and "IMD-DHH."

In humans, Nrf2 is encoded by the NFE2L2 gene which is located on chromosome 2. There are three known human Nrf2 isoforms. Isoform 1 (UniProt: Q16236-1) consists of 605 amino acids and has been chosen as the canonical sequence. Isoform 2 (UniProt: Q16236-2) consists of 589 amino acids and differs from the canonical sequence as follows: amino acids 1-16: missing. Isoform 3 (UniProt: Q16236-3) consists of 582 amino acids and differs from the canonical sequence as follows: amino acids 1-16: missing; and amino acids 135-141: missing. Table 1 (below) provides the amino acid sequences of the three known Nrf2 isoforms.

TABLE 1

Nrf2 Protein Isoforms

| Isoform 1<br>(UniProt:<br>Q16236-1) | MMDLELPPPGLPSQQDMDLIDILWRQDIDLGVSREVFDFSQRRKEYELEKQKKLEKERQE<br>QLQKEQEKAFFAQLQLDEETGEFLPIQPAQHIQSETSGSANYSQVAHIPKSDALYFDDCM<br>QLLAQTFPFVDDNEVSSATFQSLVPDIPGHIESPVFIATNQAQSPETSVAQVAPVDLDGM<br>QQDIEQVWEELLSIPELQCLNIENDKLVETTMVPSPEAKLTEVDNYHFYSSIPSMEKEVG<br>NCSPHFLNAFEDSFSSILSTEDPNQLTVNSLNSDATVNTDFGDEFYSAFIAEPSISNSMP<br>SPATLSHSLSELLNGPIDVSDLSLCKAFNQNHPESTAEFNDSDSGISLNTSPSVASPEHS<br>VESSSYGDTLLGLSDSEVEELDSAPGSVKQNGPKTPVHSSGDMVQPLSPSQGQSTHVHDA<br>QCENTPEKELPVSPGHRKTPFTKDKHSSRLEAHLTRDELRAKALHIPFPVEKIINLPVVD<br>FNEMMSKEQFNEAQLALIRDIRRRGKNKVAAQNCRKRKLENIVELEQDLDHLKDEKEKLL<br>KEKGENDKSLHLLKKQLSTLYLEVFSMLRDEDGKPYSPSEYSLQQTRDGNVFLVPKSKKP<br>DVKKN (SEQ ID NO: 1) |
| Isoform 2<br>(UniProt:<br>Q16236-2) | MDLIDILWRQDIDLGVSREVFDFSQRRKEYELEKQKKLEKERQEQLQKEQEKAFFAQLQL<br>DEETGEFLPIQPAQHIQSETSGSANYSQVAHIPKSDALYFDDCMQLLAQTFPFVDDNEVS<br>SATFQSLVPDIPGHIESPVFIATNQAQSPETSVAQVAPVDLDGMQQDIEQVWEELLSIPE<br>LQCLNIENDKLVETTMVPSPEAKLTEVDNYHFYSSIPSMEKEVGNCSPHFLNAFEDSFSS<br>ILSTEDPNQLTVNSLNSDATVNTDFGDEFYSAFIAEPSISNSMPSPATLSHSLSELLNGP<br>IDVSDLSLCKAFNQNHPESTAEFNDSDSGISLNTSPSVASPEHSVESSSYGDTLLGLSDS<br>EVEELDSAPGSVKQNGPKTPVHSSGDMVQPLSPSQGQSTHVHDAQCENTPEKELPVSPGH<br>RKTPFTKDKHSSRLEAHLTRDELRAKALHIPFPVEKIINLPVVDFNEMMSKEQFNEAQLA<br>LIRDIRRRGKNKVAAQNCRKRKLENIVELEQDLDHLKDEKEKLLKEKGENDKSLHLLKKQ<br>LSTLYLEVFSMLRDEDGKPYSPSEYSLQQTRDGNVFLVPKSKKPDVKKN (SEQ ID NO:<br>2) |
| Isoform 3<br>(UniProt:<br>Q16236-3) | MDLIDILWRQDIDLGVSREVFDFSQRRKEYELEKQKKLEKERQEQLQKEQEKAFFAQLQL<br>DEETGEFLPIQPAQHIQSETSGSANYSQVAHIPKSDALYFDDCMQLLAQTFPFVDDNESL<br>VPDIPGHIESPVFIATNQAQSPETSVAQVAPVDLDGMQQDIEQVWEELLSIPELQCLNIE<br>NDKLVETTMVPSPEAKLTEVDNYHFYSSIPSMEKEVGNCSPHFLNAFEDSFSSILSTEDP<br>NQLTVNSLNSDATVNTDFGDEFYSAFIAEPSISNSMPSPATLSHSLSELLNGPIDVSDLS<br>LCKAFNQNHPESTAEFNDSDSGISLNTSPSVASPEHSVESSSYGDTLLGLSDSEVEELDS<br>APGSVKQNGPKTPVHSSGDMVQPLSPSQGQSTHVHDAQCENTPEKELPVSPGHRKTPFTK<br>DKHSSRLEAHLTRDELRAKALHIPFPVEKIINLPVVDFNEMMSKEQFNEAQLALIRDIRR<br>RGKNKVAAQNCRKRKLENIVELEQDLDHLKDEKEKLLKEKGENDKSLHLLKKQLSTLYLE<br>VFSMLRDEDGKPYSPSEYSLQQTRDGNVFLVPKSKKPDVKKN (SEQ ID NO: 3) |

As used herein, the term "Nrf2" includes any variants or isoforms of Nrf2 which are naturally expressed by cells. The following natural variants of Nrf2 are known in the art: (i) amino acid position 31: G→R; (ii) amino acid position 43: R→Q; (iii) amino acid position 79: E→K; (iv) amino acid position 80: T→K; (v) amino acid position 81: G→S; (vi) amino acid position 99: S→P; and (vii) amino acid position 268: V→M. Accordingly, in some aspects, a modified cell disclosed herein expresses reduced levels of NFE2L2 gene and/or Nrf2 protein associated with isoform 1. In certain aspects, a modified cell disclosed herein expresses reduced levels of NFE2L2 gene and/or Nrf2 protein associated with isoform 2. In further aspects, a modified cell disclosed herein expresses reduced levels of NFE2L2 gene and/or Nrf2 protein associated with isoform 3. In still further aspects, a modified cell disclosed herein expresses reduced levels of NFE2L2 gene and/or Nrf2 protein associated with all isoforms.

In some aspects, Nrf2, or any variants and isoforms thereof, can either be isolated from cells or tissues which naturally express them or be recombinantly produced. The nucleic acid sequences of the polynucleotides encoding the above human Nrf2 isoforms are provided in Table 2 (below).

TABLE 2

Nrf2 Nucleic Acids

| Isoform 1<br>(GenBank<br>Accession No.<br>NM_006164.5) | GATTACCGAGTGCCGGGGAGCCCGGAGGAGCCGCCGACGCAGCCGCCACCGCCGCCGCCGCCGCCACCAG<br>AGCCGCCCTGTCCGCGCCGCGCCTCGGCAGCCGGAACAGGGCCGCCGTCGGGGAGCCCCAACACACGGTC<br>CACAGCTCATCATGATGGACTTGGAGCTGCCGCCGCCGGGACTCCCGTCCCAGCAGGACATGGATTTGAT<br>TGACATACTTTGGAGGCAAGATATAGATCTTGGAGTAAGTCGAGAAGTATTTGACTTCAGTCAGCGACGG<br>AAAGAGTATGAGCTGGAAAAACAGAAAAAACTTGAAAAGGAAAGACAAGAACAACTCCAAAAGGAGCAAG<br>AGAAAGCCTTTTTCGCTCAGTTACAACTAGATGAAGAGACAGGTGAATTTCTCCCAATTCAGCCAGCCCA<br>GCACATCCAGTCAGAAACCAGTGGATCTGCCAACTACTCCCAGGTTGCCCACATTCCCAAATCAGATGCT<br>TTGTACTTTGATGACTGCATGCAGCTTTTGGCGCAGACATTCCCGTTTGTAGATGACAATGAGGTTTCTT<br>CGGCTACGTTTCAGTCACTTGTTCCTGATATTCCCGGTCACATCGAGAGCCCAGTCTTCATTGCTACTAA<br>TCAGGCTCAGTCACCTGAAACTTCTGTTGCTCAGGTAGCCCCTGTTGATTTAGACGGTATGCAACAGGAC<br>ATTGAGCAAGTTTGGGAGGAGCTATTATCCATTCCTGAGTTACAGTGTCTTAATATTGAAAATGACAAGC<br>TGGTTGAGACTACCATGGTTCCAAGTCCAGAAGCCAAACTGACAGAAGTTGACAATTATCATTTTTACTC<br>ATCTATACCCTCAATGGAAAAAGAAGTAGGTAACTGTAGTCCACATTTTCTTAATGCTTTTGAGGATTCC<br>TTCAGCAGCATCCTCTCCACAGAAGACCCCAACCAGTTGACAGTGAACTCATTAAATTCAGATGCCACAG<br>TCAACACAGATTTTGGTGATGAATTTTATTCTGCTTTCATAGCTGAGCCCAGTATCAGCAACAGCATGCC<br>CTCACCTGCTACTTTAAGCCATTCACTCTCTGAACTTCTAAATGGGCCCATTGATGTTTCTGATCTATCA<br>CTTTGCAAAGCTTTCAACCAAAACCACCCTGAAAGCACAGCAGAATTCAATGATTCTGACTCCGGCATTT<br>CACTAAACACAAGTCCCAGTGTGGCATCACCAGAACACTCAGTGGAATCTTCCAGCTATGGAGACACACT<br>ACTTGGCCTCAGTGATTCTGAAGTGGAAGAGCTAGATAGTGCCCCTGGAAGTGTCAAACAGAATGGTCCT<br>AAAACACCAGTACATTCTTCTGGGGATATGGTACAACCCTTGTCACCATCTCAGGGGCAGAGCACTCACG<br>TGCATGATGCCCAATGTGAGAACACACCAGAGAAAGAATTGCCTGTAAGTCCTGGTCATCGGAAAACCCC |

TABLE 2-continued

Nrf2 Nucleic Acids

|  |  |
|---|---|
|  | ATTCACAAAAGACAAACATTCAAGCCGCTTGGAGGCTCATCTCACAAGAGATGAACTTAGGGCAAAAGCT<br>CTCCATATCCCATTCCCTGTAGAAAAAATCATTAACCTCCCTGTTGTTGACTTCAACGAAATGATGTCCA<br>AAGAGCAGTTCAATGAAGCTCAACTTGCATTAATTCGGGATATACGTAGGAGGGGTAAGAATAAAGTGGC<br>TGCTCAGAATTGCAGAAAAAGAAAACTGGAAAATATAGTAGAACTAGAGCAAGATTTAGATCATTTGAAA<br>GATGAAAAGAAAAATTGCTCAAAGAAAAAGGAGAAAATGACAAAAGCCTTCACCTACTGAAAAAACAAC<br>TCAGCACCTTATATCTCGAAGTTTTCAGCATGCTACGTGATGAAGATGGAAAACCTTATTCTCCTAGTGA<br>ATACTCCCTGCAGCAAACAAGAGATGGCAATGTTTTCCTTGTTCCCAAAAGTAAGAAGCCAGATGTTAAG<br>AAAAACTAGATTTAGGAGGATTTGACCTTTTCTGAGCTAGTTTTTTTGTACTATTATACTAAAAGCTCCT<br>ACTGTGATGTGAAATGCTCATACTTTATAAGTAATTCTATGCAAAATCATAGCCAAAACTAGTATAGAAA<br>ATAATACGAAACTTTAAAAAGCATTGGAGTGTCAGTATGTTGAATCAGTAGTTTCACTTTAACTGTAAAC<br>AATTTCTTAGGACACCATTTGGGCTAGTTTCTGTGTAAGTGTAAATACTACAAAAACTTATTTATACTGT<br>TCTTATGTCATTTGTTATATTCATAGATTTATATGATGATATGACATCTGGCTAAAAAGAAATTATTGCA<br>AAACTAACCACTATGTACTTTTTTATAAATACTGTATGGACAAAAATGGCATTTTTTATATTAAATTGT<br>TTAGCTCTGGCAAAAAAAAAAATTTTAAGAGCTGGTACTAATAAAGGATTATTATGACTGTTAAA (SEQ<br>ID NO: 4) |
| Isoform 2<br>(GenBank<br>Accession No.<br>NM_001313900.1) | GGCCCTTCCGGGGCTGCGCGGCTCCCCCGCCTCGGTGCCGGCAAAAATGTGCCTAGTCACGGGGCCGCTC<br>TCGGGGGAACTGAGGTCGCCTTCGGGCTGGGACCCGGAGCCCCTTCGCCGCGCCCCAAGACCTCCTTGAG<br>TGCGGGCTGCGACGCGCTCACCCCGCTGGGCCGTCTGTGGGCGCGGCTTTGCGAAGTCATCCATCTCTCG<br>GATCACTCTCTGGCAGCCTTGAGCTCTCTTGAAAGCCCAGCCCCGGGACGAGGGAGGAGCGCCTTAAGTG<br>CCCAGCGGGCTCAGAAGCCCCGACGTGTGGCGGCTGAGCCGGGCCCCGCGCACTTTCTCGGCCGGGGAGG<br>GGTTCGGGCTCGGGCACCCGGAGTTGGCCCCTCGTAACGCCGCGGGAAAGTGCGGGCGAGGGCAGTGGAC<br>TCTGAGGCCGGAGTCGGCGGCACCCGGGGCTTCTAGTTCGGACGCGGTGCCCCCTGGTGGCGCTCACCGC<br>GCGCGTGGCCTTGGCTTCCGTGACAGCGCTCGGTTGGCCGTCACAGCAGCCCTCGGTTGGCCCTTTCCTG<br>CTTTTATAGCGTGCAAACCTCGCCGCGCCAGGGCCAAGGGACAGGTTGGAGCTGTTGATCTGTTGCGCAAT<br>TGCTATTTTCCCCAGAGCGGCTTTGTCTTTGGATTTAGCGTTTCAGAATTGCAATTCCAAAATGTGTAAG<br>ACGGGATATTCTCTTCTGTGCTGTCAAGGGACATGGATTTGATTGACATACTTTGGAGGCAAGATATAGA<br>TCTTGGAGTAAGTCGAGAAGTATTTGACTTCAGTCAGCGACGGAAAGAGTATGAGCTGGAAAAACAGAAA<br>AAACTTGAAAAGGAAAGACAAGAACAACTCCAAAAGGAGCAAGAGAAAGCCTTTTTCGCTCAGTTACAAC<br>TAGATGAAGAGACAGGTGAATTTCTCCCAATTCAGCCAGCCCAGCACATCCAGTCAGAAACCAGTGGATC<br>TGCCAACTACTCCCAGGTTGCCCACATTCCCAAATCAGATGCTTTGTACTTTGATGACTGCATGCCAGCTT<br>TTGGCGCAGACATTCCCGTTTGTAGATGACAATGAGGTTTCTTCGGCTACGTTTCAGTCACTTGTTCCTG<br>ATATTCCCGGTCACATCGAGAGCCCAGTCTTCATTGCTACTAATCAGGCTCAGTCACCTGAAACTTCTGT<br>TGCTCAGGTAGCCCCTGTTGATTTAGACGGTATGCAACAGGACATTGAGCAAGTTTGGGAGGAGCTATTA<br>TCCATTCCTGAGTTACAGTGTCTTAATATTGAAAATGACAAGCTGGTTGAGACTACCATGGTTCCAAGTC<br>CAGAAGCCAAACTGACAGAAGTTGACAATTATCATTTTTACTCATCTATACCCTCAATGGAAAAGAAGAAGT<br>AGGTAACTGTAGTCCACATTTTCTTAATGCTTTTGAGGATTCCTTCAGCAGCATCCTCTCCACAGAAGAC<br>CCCAACCAGTTGACAGTGAACTCATTAAATTCAGATGCCACAGTCAACACAGATTTTGGTGATGAATTTT<br>ATTCTGCTTTCATAGCTGAGCCCAGTATCAGCAACAGCATGCCCTCACCTGCTACTTTAAGCCATTCACT<br>CTCTGAACTTCTAAATGGGCCCATTGATGTTTCTGATCTATCACTTTGCAAAGCTTTCAACCAAAACCAC<br>CCTGAAAGCACAGCAGAATTCAATGATTCTGACTCCGGCATTTCACTAAACACAAGTCCCAGTGTGGCAT<br>CACCAGAACACTCAGTGGAATCTTCCAGCTATGGAGACACACTACTTGGCCTCAGTGATTCTGAAGTGGA<br>AGAGCTAGATAGTGCCCCTGGAAGTGTCAAACAGAATGGTCCTAAAACACCAGTACATTCTTCTGGGGAT<br>ATGGTACAACCCTTGTCACCATCTCAGGGGCAGAGCACTCACGTGCATGATGCCCAATGTGAGAACACAC<br>CAGAGAAAGAATTGCCTGTAAGTCCTGGTCATCGGAAAACCCCATTCACAAAAGACAAACATTCAAGCCG<br>CTTGGAGGCTCATCTCACAAGAGATGAACTTAGGGCAAAAGCTCTCCATATCCCATTCCCTGTAGAAAAA<br>ATCATTAACCTCCCTGTTGTTGACTTCAACGAAATGATGTCCAAAGAGCAGTTCAATGAAGCTCAACTTG<br>CATTAATTCGGGATATACGTAGGAGGGGTAAGAATAAAGTGGCTGCTCAGAATTGCAGAAAAAGAAAACT<br>GGAAAATATAGTAGAACTAGAGCAAGATTTAGATCATTTGAAAGATGAAAAGAAAAATTGCTCAAAGAA<br>AAAGGAGAAAATGACAAAAGCCTTCACCTACTGAAAAAACAACTCAGCACCTTATATCTCGAAGTTTTCA<br>GCATGCTACGTGATGAAGATGGAAAACCTTATTCTCCTAGTGAATACTCCCTGCAGCAAACAAGAGATGG<br>CAATGTTTTCCTTGTTCCCAAAAGTAAGAAGCCAGATGTTAAGAAAAACTAGATTTAGGAGGATTTGACC<br>TTTTCTGAGCTAGTTTTTTTGTACTATTATACTAAAAGCTCCTACTGTGATGTGAAATGCTCATACTTTA<br>TAAGTAATTCTATGCAAAATCATAGCCAAAACTAGTATAGAAAATAATACGAAACTTTAAAAAGCATTGG<br>AGTGTCAGTATGTTGAATCAGTAGTTTCACTTTAACTGTAAACAATTTCTTAGGACACCATTTGGGCTAG<br>TTTCTGTGTAAGTGTAAATACTACAAAAACTTATTTATATTCATAGATTTATATGATGATATGACATCTGGCTAAAAAGAAATTATTGCAAAACTAACCACTATGTACTTTTTTATA<br>AATACTGTATGGACAAAAATGGCATTTTTTATATTAAATTGTTTAGCTCTGGCAAAAAAAAAAAATTTT<br>AAGAGCTGGTACTAATAAAGGATTATTATGACTGTTAAATTATTAAAA (SEQ ID NO: 5) |
| Isoform 3<br>(GenBank<br>Accession No.<br>NM_001145413.3) | GGCCCTTCCGGGGCTGCGCGGCTCCCCCGCCTCGGTGCCGGCAAAAATGTGCCTAGTCACGGGGCCGCTC<br>TCGGGGGAACTGAGGTCGCCTTCGGGCTGGGACCCGGAGCCCCTTCGCCGCGCCCCAAGACCTCCTTGAG<br>TGCGGGCTGCGACGCGCTCACCCCGCTGGGCCGTCTGTGGGCGCGGCTTTGCGAAGTCATCCATCTCTCG<br>GATCACTCTCTGGCAGCCTTGAGCTCTCTTGAAAGCCCAGCCCCGGGACGAGGGAGGAGCGCCTTAAGTG<br>CCCAGCGGGCTCAGAAGCCCCGACGTGTGGCGGCTGAGCCGGGCCCCGCGCACTTTCTCGGCCGGGGAGG<br>GGTTCGGGCTCGGGCACCCGGAGTTGGCCCCTCGTAACGCCGCGGGAAAGTGCGGGCGAGGGCAGTGGAC<br>TCTGAGGCCGGAGTCGGCGGCACCCGGGGCTTCTAGTTCGGACGCGGTGCCCCCTGGTGGCGCTCACCGC<br>GCGCGTGGCCTTGGCTTCCGTGACAGCGCTCGGTTGGCCGTCACAGCAGCCCTCGGTTGGCCCTTTCCTG<br>CTTTTATAGCGTGCAAACCTCGCCGCGCCAGGGCCAAGGGACAGGTTGGAGCTGTTGATCTGTTGCGCAAT<br>TGCTATTTTCCCCAGAGCGGCTTTGTCTTTGGATTTAGCGTTTCAGAATTGCAATTCCAAAATGTGTAAG<br>ACGGGATATTCTCTTCTGTGCTGTCAAGGGACATGGATTTGATTGACATACTTTGGAGGCAAGATATAGA<br>TCTTGGAGTAAGTCGAGAAGTATTTGACTTCAGTCAGCGACGGAAAGAGTATGAGCTGGAAAAACAGAAA<br>AAACTTGAAAAGGAAAGACAAGAACAACTCCAAAAGGAGCAAGAGAAAGCCTTTTTCGCTCAGTTACAAC<br>TAGATGAAGAGACAGGTGAATTTCTCCCAATTCAGCCAGCCCAGCACATCCAGTCAGAAACCAGTGGATC<br>TGCCAACTACTCCCAGGTTGCCCACATTCCCAAATCAGATGCTTTGTACTTTGATGACTGCATGCAGCTT<br>TTGGCGCAGACATTCCCGTTTGTAGATGACAATGAGTCACTTGTTCCTGATATTCCCGGTCACATCGAGA<br>GCCCAGTCTTCATTGCTACTAATCAGGCTCAGTCACCTGAAACTTCTGTTGCTCAGGTAGCCCCTGTTGA<br>TTTAGACGGTATGCAACAGGACATTGAGCAAGTTTGGGAGGAGCTATTATCCATTCCTGAGTTACAGTGT |

TABLE 2-continued

Nrf2 Nucleic Acids

```
CTTAATATTGAAAATGACAAGCTGGTTGAGACTACCATGGTTCCAAGTCCAGAAGCCAAACTGACAGAAG
TTGACAATTATCATTTTTACTCATCTATACCCTCAATGGAAAAAGAAGTAGGTAACTGTAGTCCACATTT
TCTTAATGCTTTTGAGGATTCCTTCAGCAGCATCCTCTCCACAGAAGACCCCAACCAGTTGACAGTGAAC
TCATTAAATTCAGATGCCACAGTCAACACAGATTTTGGTGATGAATTTTATTCTGCTTTCATAGCTGAGC
CCAGTATCAGCAACAGCATGCCCTCACCTGCTACTTTAAGCCATTCACTCTCTGAACTTCTAAATGGGCC
CATTGATGTTTCTGATCTATCACTTTGCAAAGCTTTCAACCAAAACCACCCTGAAAGCACAGCAGAATTC
AATGATTCTGACTCCGGCATTTCACTAAACACAAGTCCCAGTGTGGCATCACCAGAACACTCAGTGGAAT
CTTCCAGCTATGGAGACACACTACTTGGCCTCAGTGATTCTGAAGTGGAAGAGCTAGATAGTGCCCCTGG
AAGTGTCAAACAGAATGGTCCTAAAACACCAGTACATTCTTCTGGGGATATGGTACAACCCTTGTCACCA
TCTCAGGGGCAGAGCACTCACGTGCATGATGCCCAATGTGAGAACACACCAGAGAAAGAATTGCCTGTAA
GTCCTGGTCATCGGAAAACCCCATTCACAAAAGACAAACATTCAAGCCGCTTGGAGGCTCATCTCACAAG
AGATGAACTTAGGGCAAAAGCTCTCCATATCCCATTCCCTGTAGAAAAAATCATTAACCTCCCTGTTGTT
GACTTCAACGAAATGATGTCCAAAGAGCAGTTCAATGAAGCTCAACTTGCATTAATTCGGGATATACGTA
GGAGGGGTAAGAATAAAGTGGCTGCTCAGAATTGCAGAAAAAGAAAACTGGAAAATATAGTAGAACTAGA
GCAAGATTTAGATCATTTGAAAGATGAAAAAGAAAAATTGCTCAAAGAAAAAGGAGAAAATGACAAAAGC
CTTCACCTACTGAAAAAACAACTCAGCACCTTATATCTCGAAGTTTTCAGCATGCTACGTGATGAAGATG
GAAAACCTTATTCTCCTAGTGAATACTCCCTGCAGCAAACAAGAGATGGCAATGTTTTCCTTGTTCCCAA
AAGTAAGAAGCCAGATGTTAAGAAAAACTAGATTTAGGAGGATTTGACCTTTTCTGAGCTAGTTTTTTTG
TACTATTATACTAAAAGCTCCTACTGTGATGTGAAATGCTCATACTTTATAAGTAATTCTATGCAAAATC
ATAGCCAAAACTAGTATAGAAAATAATACGAAACTTTAAAAAGCATTGGAGTGTCAGTATGTTGAATCAG
TAGTTTCACTTTAACTGTAAACAATTTCTTAGGACACCATTTGGGCTAGTTTCTGTGTAAGTGTAAATAC
TACAAAAACTTATTTATACTGTTCTTATGTCATTTGTTATATTCATAGATTTATATGATGATATGACATC
TGGCTAAAAAGAAATTATTGCAAAACTAACCACTATGTACTTTTTTATAAATACTGTATGGACAAAAAAT
GGCATTTTTTATATTAAATTGTTTAGCTCTGGCAAAAAAAAAAATTTTAAGAGCTGGTACTAATAAAGG
ATTATTATGACTGTTAAATTATTAAAA (SEQ ID NO: 6)
```

In some aspects, the expression level of the NFE2L2 gene is reduced by at least about 5%, at least about 10%, at least about 20%, at least about 30%, at least about 40%, at least about 50%, at least about 60%, at least about 70%, at least about 80%, at least about 90%, or at least about 100%, compared to a reference cell (e.g., corresponding cell that has not been modified to express lower levels of the NFE2L2 gene). In some aspects, the expression level of the Nrf2 protein is reduced by at least about 5%, at least about 10%, at least about 20%, at least about 30%, at least about 40%, at least about 50%, at least about 60%, at least about 70%, at least about 80%, at least about 90%, or at least about 100%, compared to a reference cell (e.g., corresponding cell that has not been modified to express lower levels of NFE2L2 gene and/or Nrf2 protein). In certain aspects, the expression levels of both the NFE2L2 gene and the Nrf2 protein are reduced by at least about 5%, at least about 10%, at least about 20%, at least about 30%, at least about 40%, at least about 50%, at least about 60%, at least about 70%, at least about 80%, at least about 90%, or at least about 100%, compared to a reference cell (e.g., corresponding cell that has not been modified to express lower levels of the NFE2L2 gene).

In some aspects, treating a tumor comprises reducing a tumor volume in the subject. Accordingly, in certain aspects, administering the modified cell of the present disclosure (i.e., expressing reduced levels of NFE2L2 gene and/or Nrf2 protein) to the subject reduces a tumor volume in the subject, compared to a reference tumor volume. In some aspects, the reference tumor volume is the tumor volume in the subject prior to the administration of the modified cell. In further aspects, the reference tumor volume is the tumor volume in a corresponding subject that did not receive the administration. In some aspects, the tumor volume in the subject is reduced by at least about 5%, at least about 10%, at least about 20%, at least about 30%, at least about 40%, at least about 50%, at least about 60%, at least about 70%, at least about 80%, at least about 90%, or at least about 100% after the administration compared to the reference tumor volume.

In some aspects, treating a tumor comprises reducing a tumor weight in the subject. In certain aspects, a modified cell disclosed herein can reduce the tumor weight in a subject when administered to the subject. In some aspects, the tumor weight is reduced by at least about 5%, at least about 10%, at least about 20%, at least about 30%, at least about 40%, at least about 50%, at least about 60%, at least about 70%, at least about 80%, at least about 90%, or at least about 100% after the administration compared to a reference tumor weight. In some aspects, the reference tumor weight is the tumor weight in the subject prior to the administration of the modified cell. In further aspects, the reference tumor weight is the tumor weight in a corresponding subject that did not receive the administration.

In some aspects, administering a modified cell of the present disclosure can increase the number and/or percentage of TILs (e.g., CD4$^+$ or CD8$^+$) in a tumor of the subject. In certain aspects, the number and/or percentage of TILs in a tumor is increased by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, or at least about 300% or more compared to a reference (e.g., corresponding value in a subject that did not receive the modified cell or the same subject prior to the administration of the modified cell).

In some aspects, administering a modified cell of the present disclosure (i.e., expressing reduced levels of NFE2L2 gene and/or Nrf2 protein) can reduce the number and/or percentage of regulatory T cells (Tregs) in a tumor of a subject. In some aspects, the regulatory T cells are CD4$^+$ regulatory T cells. In some aspects, the regulatory T cells are Foxp3$^+$. In certain aspects, the number and/or percentage of regulatory T cells in a tumor is decreased by at least about 5%, at least about 10%, at least about 20%, at least about 30%, at least about 40%, at least about 50%, at least about 60%, at least about 70%, at least about 80%, at least about 90%, or about 100% compared to a reference (e.g., the corresponding number and/or percentage in a subject that did not receive an administration of the modified cell).

In some aspects, administering a modified cell disclosed herein can increase the ratio of CD8$^+$ TILs to Tregs in a tumor of a subject. In certain aspects, the ratio of CD8+ TILs to Tregs is increased by at least about 5%, at least about 10%, at least about 20%, at least about 30%, at least about 40%, at least about 50%, at least about 60%, at least about 70%, at least about 80%, at least about 90%, at least about 100%, at least about 125%, at least about 150%, at least about 200%, at least about 250%, or at least about 300% after the administration compared to a reference (e.g., number and/or percentage of TILs in a tumor of a subject that did not receive an administration of the modified cell).

In some aspects, administering a modified cell disclosed herein can decrease the number and/or percentage of myeloid-derived suppressor cells (MDSCs) in the tumor of a subject. As used herein, the term "myeloid-derived suppressor cells" (MDSCs) refers to a heterogeneous population of immune cells that are defined by their myeloid origin, immature state, and ability to potently suppress T cell responses. They are known to expand in certain pathological conditions, such as chronic infections and cancers. In certain aspects, the MDSCs are monocytic MDSCs (M-MDSCs). In other aspects, the MDSCs are polymorphonuclear MDSCs (PMN-MDSCs). In some aspects, the number and/or percentage of MDSCs in the tumor is decreased by at least about 5%, at least about 10%, at least about 20%, at least about 30%, at least about 40%, at least about 50%, at least about 60%, at least about 70%, at least about 80%, at least about 90%, or about 100% compared to a reference (e.g., value in a corresponding subject that did not receive an administration of the modified cell).

In some aspects, administering a modified cell disclosed herein can increase the ratio of CD8+ TILs to MDSCs in a tumor of a subject. In certain aspects, the ratio of CD8+ TILs to MDSCs is increased by at least about 5%, at least about 10%, at least about 20%, at least about 30%, at least about 40%, at least about 50%, at least about 60%, at least about 70%, at least about 80%, at least about 90%, at least about 100%, at least about 125%, at least about 150%, at least about 200%, at least about 250%, or at least about 300% after the administration compared to a reference (e.g., value in a corresponding subject that did not receive an administration of the modified cell).

In some aspects, a modified cell disclosed herein (i.e., expresses reduced levels of NFE2L2 gene and/or Nrf2 protein) comprises immune cells. In certain aspects, immune cells comprise a lymphocyte, neutrophil, monocyte, macrophage, dendritic cell, or combinations thereof. In further aspects, a modified immune cell disclosed herein is a lymphocyte. In some aspects, a lymphocyte comprises a T cell, a tumor-infiltrating lymphocyte (TIL), a lymphokine-activated killer cell, a natural killer (NK) cell, or any combination thereof. In further aspects, a modified immune cell can further comprise a chimeric antigen receptor (CAR). In some aspects, a modified immune cell can further comprise a T cell receptor, e.g., an engineered TCR. Accordingly, in certain aspects, a modified cell disclosed herein is a T cell. In some aspects, a modified cell disclosed herein is a TIL. In some aspects, a modified cell disclosed herein is an NK cell. In some aspects, a modified cell disclosed herein is a lymphokine-activated killer cell. In some aspects, the T cell comprises a CAR. In other aspects, a modified cell disclosed herein is a NK cell. In certain aspects, the NK cell comprises a CAR. In further aspects, a modified cell of the presence disclosure comprises both T cells and NK cells. In certain aspects, the T cells and NK cells both comprise CARs.

In some aspects, the present methods can be used to modify any immune cell type. In other aspects, the present methods are used to modify cells for any adoptive cell transfer (ACT) therapy (also known as adoptive cell therapy). ACT therapy can be an autologous therapy or allogenic therapy. In some aspects, the ACT therapy includes, but are not limited to a CAR T therapy, a tumor-infiltrating lymphocyte (TIL) therapy, an NK cell therapy, or any combination thereof.

In some aspects, the present methods can be used to modify TILs for a TIL therapy. The use of TILs as an adoptive cell transfer therapy to treat cancer have been studied for more than two decades using TIL adoptive cell therapy for melanoma. Rosenberg S A et al., (July 2011). *Clinical Cancer Research* 17 (13): 4550-7 (July 2011). In Adoptive T cell transfer therapy, TILs are expanded ex vivo from surgically resected tumors that have been cut into small fragments or from single cell suspensions isolated from the tumor fragments. Multiple individual cultures are established, grown separately and assayed for specific tumor recognition. TILs are expanded over the course of a few weeks. Selected TIL lines that presented best tumor reactivity are then further expanded in a "rapid expansion protocol" (REP), which uses anti-CD3 activation for a typical period of two weeks. The TILs grown in the culture can be modified any time during the ex vivo process so that the expression of NFE2L2 gene and/or Nrf2 protein is reduced. The final post-REP TIL is infused back into the patient. The process can also involve a preliminary chemotherapy regimen to deplete endogenous lymphocytes in order to provide the adoptively transferred TILs with enough access to surround the tumor sites.

In some aspects, the present methods can be used to modify a T cell with T cell receptors, e.g., engineered TCRs. As used herein, the term "engineered TCR" or "engineered T-cell receptor" refers to a T-cell receptor (TCR) engineered to specifically bind with a desired affinity to a major histocompatibility complex (MHC)/peptide target antigen that is selected, cloned, and/or subsequently introduced into a population of T-cells.

In some aspects, a modified cell disclosed herein (i.e., expressing reduced levels of NFE2L2 gene and/or Nrf2 protein) can have one or more improved properties. In certain aspects, improving one or more properties of a cell (e.g., immune cell, e.g., tumor-infiltrating lymphocytes) can help treat a tumor (e.g., reduce tumor volume and/or tumor weight). The one or more properties that can be improved with the present disclosure include any properties of a cell (e.g., TILs) that can be useful in treating cancers. For instance, in certain aspects, such properties include: (i) increased expansion and/or proliferation; (ii) increased persistence and/or survival (e.g., less exhausted/anergic); (iii) increased anti-tumor activity (e.g., ability to target and kill a tumor cell); and (iv) combinations thereof.

In some aspects, the expansion and/or proliferation of a modified cell disclosed herein is increased by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, or at least about 300% or more compared to a reference (e.g., corresponding value in a subject that did not receive the modified cell or the same subject prior to the administration of the modified cell). In some aspects, the persistence and/or survival of a modified cell disclosed herein is increased by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, or at least about 300% or more compared to a reference (e.g., corresponding value in a subject that did not receive the modified cell or the same subject prior to the administration of the modified cell). In further aspects, the anti-tumor activity of a modified cell disclosed herein is increased by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, or at least about 300% or more compared to a reference (e.g., corresponding value in a subject that did not receive the modified cell or the same subject prior to the administration of the modified cell).

In some aspects, the one or more properties can comprise the ability of a cell (e.g., TILs) to produce effector molecules that are useful in treating tumors. In certain aspects, effector molecules comprise a cytokine. Non-limiting examples of effector molecules include IFN-γ, TNF-α, IL-2, Granzyme B, Perforin, CD107a or combinations thereof. Accordingly, in some aspects, a modified cell disclosed herein can produce an increased amount of IFN-γ when stimulated with an antigen, such as a cognate antigen (e.g., tumor antigen). In certain aspects, the amount of IFN-γ produced is increased by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, or at least about 300% or more compared to a reference cell (e.g., a corresponding cell that has not been modified to express reduced levels of NFE2L2 gene and/or Nrf2 protein).

As described herein, Nrf2 has been described in the art as being important in protecting cells from oxidative stress that can be caused by agents such as reactive oxygen and nitrogen species. Applicant has discovered that the modified cells disclosed herein (i.e., express reduced levels of NFE2L2 gene and/or Nrf2 protein) exhibit increased resistance to oxidative stress compared to a reference cell. In some aspects, the reference cell is a corresponding cell which has not been modified to express reduced levels of NFE2L2 gene and/or Nrf2 protein. In certain aspects, the resistance to oxidative stress of the modified cells disclosed herein is increased by at least about 5%, at least about 10%, at least about 20%, at least about 30%, at least about 40%, at least about 50%, at least about 60%, at least about 70%, at least about 80%, at least about 90%, or at least about 100% or more compared to the reference cell.

In some aspects, a modified cell disclosed herein can be modified using a gene editing tool. In some aspects, a modified cell disclosed herein can be modified using RNAi. In some aspects, a modified cell disclosed herein can be modified using antisense oligonucleotides. Further description of useful gene editing tools for the present disclosure are provided elsewhere herein.

In some aspects, the modified cells described herein can be further modified to express a chimeric antigen receptor. In some aspects, the modified CAR expressing cells can have improved anticancer properties.

Not being bound by any theory, the modified cell of the present disclosure is capable of reducing or preventing T cell exhaustion.

Whether a cell exhibits increased resistance to oxidative stress can be measured by any methods available in the art. In some aspects, increasing the resistance of a cell to oxidative stress can result in the cell to exhibit improved function. For instance, in certain aspects, a modified cell disclosed herein can proliferate even in the presence of elevated concentrations of a radical oxygen species. In some aspects, a modified cell of the present disclosure can express cytolytic molecules even in the presence of elevated concentrations of a radical oxygen species. In certain aspects, cytolytic molecules comprise granzyme B. In further aspects, a modified cell of the present disclosure can produce cytokines even in the presence of elevated concentrations of a radical oxygen species. In some aspects, cytokines comprise IFN-γ. In some aspects, radical oxygen species comprises hydrogen peroxide ($H_2O_2$). In certain aspects, a modified cell disclosed herein can (i) proliferate, (ii) express cytolytic molecules, and (iii) produce cytokines even in the presence of elevated concentrations of a radical oxygen species.

As described herein, the modified cells of the present disclosure (i.e., expresses reduced levels of NFE2L2 gene and/or Nrf2 protein) can be used to treat variety of cancer types. Non-limiting examples of cancers (or tumors) that can be treated with methods disclosed herein include squamous cell carcinoma, small-cell lung cancer (SCLC), non-small cell lung cancer, squamous non-small cell lung cancer (NSCLC), nonsquamous NSCLC, gastrointestinal cancer, renal cancer (e.g., clear cell carcinoma), ovarian cancer, liver cancer (e.g., hepatocellular carcinoma), colorectal cancer, endometrial cancer, kidney cancer (e.g., renal cell carcinoma (RCC)), prostate cancer (e.g., hormone refractory prostate adenocarcinoma), thyroid cancer, pancreatic cancer, cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus (e.g., gastroesophageal junction cancer), cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, tumor angiogenesis, pituitary adenoma, Kaposi's sarcoma, epidermoid cancer, squamous cell cancer, T-cell lymphoma, environmentally-induced cancers including those induced by asbestos, virus-related cancers or cancers of viral origin (e.g., human papilloma virus (HPV-related or -originating tumors)), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CIVIL), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosaassociated lymphoid tissue (MALT) lymphoma, anaplastic (e.g., Ki 1$^+$) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary effusion lymphoma, B cell lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyosarcoma; seminoma, teratocarcinoma, tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, and any combinations thereof.

In some aspects, a cancer (or tumor) that can be treated with the modified cells disclosed herein comprises a breast cancer, head and neck cancer, uterine cancer, brain cancer, skin cancer, renal cancer, lung cancer, colorectal cancer, prostate cancer, liver cancer, bladder cancer, kidney cancer, pancreatic cancer, thyroid cancer, esophageal cancer, eye cancer, stomach (gastric) cancer, gastrointestinal cancer, carcinoma, sarcoma, leukemia, lymphoma, myeloma, or a combination thereof. In certain aspects, a cancer (or tumor) that can be treated with the present disclosure is breast cancer. In some aspects, breast cancer is a triple negative breast cancer (TNBC). In some aspects, a cancer (or tumor) that can be treated is a brain cancer. In certain aspects, brain cancer is a glioblastoma. In some aspects, a cancer (or tumor) that can be treated with the present disclosure is skin cancer. In some aspects, skin cancer is a basal cell carcinoma (BCC), cutaneous squamous cell carcinoma (cSCC), melanoma, Merkel cell carcinoma (MCC), or a combination thereof. In certain aspects, a head and neck cancer is a head and neck squamous cell carcinoma. In further aspects, a lung cancer is a small cell lung cancer (SCLC). In some aspects, an esophageal cancer is gastroesophageal junction cancer. In certain aspects, a kidney cancer is renal cell carcinoma. In some aspects, a liver cancer is hepatocellular carcinoma. In certain aspects, cancers that can be treated with the present disclosure comprise a colorectal cancer, skin cancer, lymphoma, lung cancer, or combinations thereof.

In some aspects, the modified cells disclosed herein can be used in combination with other therapeutic agents (e.g., anti-cancer agents and/or immunomodulating agents). Accordingly, in certain aspects, a method of treating a tumor disclosed herein comprises administering the modified cells of the present disclosure in combination with one or more additional therapeutic agents. Such agents can include, for example, chemotherapeutic drug, targeted anti-cancer therapy, oncolytic drug, cytotoxic agent, immune-based therapy, cytokine, surgical procedure, radiation procedure, activator of a costimulatory molecule, immune checkpoint inhibitor, a vaccine, a cellular immunotherapy, or any combination thereof. In some aspects, the modified cells disclosed herein (i.e., expressing reduced levels of NFE2L2 gene and/or Nrf2 protein) can be used in combination with a standard of care treatment (e.g., surgery, radiation, and chemotherapy). Methods described herein can also be used as a maintenance therapy, e.g., a therapy that is intended to prevent the occurrence or recurrence of tumors.

In some aspects, the modified cells of the present disclosure can be used in combination with one or more anti-cancer agents, such that multiple elements of the immune pathway can be targeted. Non-limiting of such combinations include: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells (e.g., myeloid-derived suppressor cells); a therapy that stimulates positive immune regulation, e.g., with agonists that stimulate the CD-137, OX-40, and/or CD40 or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; blocking of immuno repressive cytokines; or any combination thereof.

In some aspects, an anti-cancer agent comprises an immune checkpoint inhibitor (i.e., blocks signaling through the particular immune checkpoint pathway). Non-limiting examples of immune checkpoint inhibitors that can be used in the present methods comprise a CTLA-4 antagonist (e.g., anti-CTLA-4 antibody), PD-1 antagonist (e.g., anti-PD-1 antibody, anti-PD-L1 antibody), TIM-3 antagonist (e.g., anti-TIM-3 antibody), or combinations thereof. Non-limiting examples of such immune checkpoint inhibitors include the following: anti-PD1 antibody (e.g., nivolumab)(OPDIVO®), pembrolizumab (KEYTRUIDA®; MK-3475), pidilizumab (CT-011), PDR001, MEDI0680 (AMP-514), TSR-042, REGN2810, JS001, AMP-224 (GSK-2661380), PF-06801591, BGB-A317, BI 754091, SHR-1210, and combinations thereof); anti-PD-L1 antibody (e.g., atezolizumab (TECENTRTQ®; RG7446; MPDL3280A; R05541267), durvalumab (MEDI4736, IMFINZI®), BMS-936559, avelumab)(BAVENCIO®), LY3300054, CX-072

(Proclaim-CX-072), FAZ053, KN035, MDX-1105, and combinations thereof); and anti-CTLA-4 antibody (e.g., ipilimumab)(YERVOY®), tremelimumab (ticilimumab; CP-675,206), AGEN-1884, ATOR-1015, and combinations thereof).

In some aspects, an anti-cancer agent comprises an immune checkpoint activator (i.e., promotes signaling through the particular immune checkpoint pathway). In certain aspects, immune checkpoint activator comprises OX40 agonist (e.g., anti-OX40 antibody), LAG-3 agonist (e.g. anti-LAG-3 antibody), 4-1BB (CD137) agonist (e.g., anti-CD137 antibody), GITR agonist (e.g., anti-GITR antibody), or combinations thereof.

In some aspects, a modified cell disclosed herein is administered to the subject prior to or after the administration of the additional therapeutic agent. In other aspects, the modified cell is administered to the subject concurrently with the additional therapeutic agent. In certain aspects, the modified cell and the additional therapeutic agent can be administered concurrently as a single composition in a pharmaceutically acceptable carrier. In other aspects, the modified cell and the additional therapeutic agent are administered concurrently as separate compositions.

In some aspects, a subject that can be treated with the present disclosure is a nonhuman animal such as a rat or a mouse. In some aspects, the subject that can be treated is a human.

IIb. Method of Improving an Immune Response

In some aspects, the present disclosure is directed to method of improving an immune response in a subject. In particular, the methods disclosed herein can be used to improve (e.g., increase) the immune response, e.g., preventing, reducing, or inhibiting immune tolerance, of an immune cell therapy, e.g., a chimeric antigen receptor (CAR)-expressing cell or an engineered T cell receptor (TCR) expressing cell in a subject. In certain aspects, the immune response is an anti-tumor immune response. In certain aspects, improving an immune response comprises preventing, reducing, or inhibiting immune tolerance. Accordingly, provided herein is a method of improving an anti-tumor immune response of a CAR-expressing cell or a TCR-expressing cell, the method comprising modifying the cell to express reduced levels of NFE2L2 gene and/or Nrf2 protein. In some aspects, the reduced expression of NFE2L2 gene and/or Nrf2 protein improves the anti-tumor immune response of the CAR-expressing cell or a TCR-expressing cell. In some aspects, the reduced expression of NFE2L2 gene and/or Nrf2 protein reduces or inhibits the immune tolerance of the CAR-expressing cell or a TCR-expressing cell.

In some aspects, the expression level of the NFE2L2 gene and/or Nrf2 protein of a CAR-expressing cell or a TCR-expressing cell is reduced by at least about 5%, at least about 10%, at least about 20%, at least about 30%, at least about 40%, at least about 50%, at least about 60%, at least about 70%, at least about 80%, at least about 90%, or at least about 100%, compared to a reference cell (e.g., corresponding cell that has not been modified to express lower levels of NFE2L2 gene and/or Nrf2 protein). In certain aspects, the expression of NFE2L2 gene and/or Nrf2 protein in the CAR-expressing cell or TCR-expressing cell is completely inhibited after the modification.

In some aspects, the anti-tumor immune response of a modified CAR-expressing cell or TCR-expressing cell (i.e., modified to express reduced levels of NFE2L2 gene and/or Nrf2 protein) is increased by at least about at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, or at least about 300% or more, compared to a reference anti-tumor immune response (e.g., anti-tumor immune response of a cell that has not been modified to express reduced levels of NFE2L2 gene and/or Nrf2 protein).

The anti-tumor immune response of a CAR-expressing cell or a TCR-expressing cell can be measured using various methods known in the art. For example, in some aspects, the anti-tumor immune response of a CAR-expressing cell or a TCR-expressing cell can be observed by measuring (e.g., with ELISA or flow cytometry) the amount of effector molecules that the cell produces upon stimulation with cognate antigen. In certain aspects, an effector molecule comprises a cytokine, e.g., such as those that are useful in treating tumors. Non-limiting examples of effector molecules include IFN-γ, TNF-α, IL-2, Granzyme B, Perforin, CD107a, or combinations thereof. In certain aspects, the cytokine is IFN-γ. Accordingly, in some aspects, improving an anti-tumor response of a cell comprises increasing the amount of IFN-γ produced by the cell. In some aspects, modified CAR-expressing cells or modified TCR-expressing cells (i.e., expressing reduced levels of NFE2L2 gene and/or Nrf2 protein) produce an increased amount of IFN-γ when stimulated with a cognate antigen (e.g., tumor antigen) compared to a reference cell (e.g., corresponding cell that has not been modified to express lower levels of NFE2L2 gene and/or Nrf2 protein). In certain aspects, the amount of IFN-γ produced is increased by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, or at least about 300% or more compared to the reference cell.

In some aspects, the anti-tumor immune response of a CAR-expressing cell or a TCR-expressing cell can be measured by assessing the proliferative capacity of the cell upon stimulation with cognate antigen (e.g., tumor antigen). In certain aspects, modified CAR-expressing cells or modified TCR-expressing cells (i.e., expressing reduced levels of NFE2L2 gene and/or Nrf2 protein) exhibit increased proliferation upon stimulation compared to a reference cell (e.g., corresponding cell that has not been modified to express lower levels of NFE2L2 gene and/or Nrf2 protein). In some aspects, the proliferation of the modified CAR-expressing cells or modified TCR-expressing cells is increased by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, or at least about 300% or more compared to the reference cell.

In some aspects, the anti-tumor immune response of a CAR-expressing cell or a TCR-expressing cell can be assessed by observing the expression of different phenotypic markers on the surface of the cells (e.g., using flow cytometry). For instance, in certain aspects, improving the anti-tumor immune response of a CAR-expressing cell or a TCR-expressing cell (i.e., by reducing the expression of NFE2L2 gene and/or Nrf2 protein) comprises reducing the expression of one or more immune checkpoint inhibitor molecules on the cells (e.g., PD-1). Accordingly, in some aspects, the modified CAR-expressing cells or modified TCR-expressing cells disclosed herein express reduced levels of one or more immune checkpoint inhibitors. In certain aspects, the expression level of one or more immune checkpoint inhibitor molecules is reduced by at least about 5%, at least about 10%, at least about 20%, at least about 30%, at least about 40%, at least about 50%, at least about 60%, at least about 70%, at least about 80%, at least about 90%, or about 100% compared to a reference cell (e.g., corresponding cell that has not been modified to express lower levels of NFE2L2 gene and/or Nrf2 protein).

In some aspects, improving the anti-tumor immune response of a CAR-expressing cell or a TCR-expressing cell comprises increasing the expression of markers associated with effector activity (e.g., anti-tumor activity). Non-limiting examples of markers associated with effector activity includes Ki-67, granzyme B, T-bet, Eomes, CXCR3, or combinations thereof. As will be apparent to those skilled in the art, in some aspects, markers associated with effector activity can also be cytokines, such as those described above (e.g., IFN-γ, TNF-α, IL-2). In certain aspects, the marker associated with effector activity is granzyme B. In some aspects, a modified CAR-expressing cell or TCR-expressing cell disclosed herein expresses greater level of granzyme B compared to a reference cell (e.g., corresponding cell that has not been modified to express lower levels of NFE2L2 gene and/or Nrf2 protein). In certain aspects, the expression level of granzyme B in the modified CAR-expressing cell or TCR-expressing cell is increased by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, or at least about 300% or more compared to the reference cell.

In some aspects, reducing the expression of NFE2L2 gene and/or Nrf2 protein in a CAR-expressing cell or a TCR-expressing cell can increase the resistance of the CAR-expressing cell or TCR-expressing cell to oxidative stress, such as those caused by reactive oxygen species (ROS) and/or reactive nitrogen species (RNS). In some aspects, the resistance to oxidative stress is increased by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, or at least about 300% or more compared to a reference cell (e.g., corresponding cell that has not been modified to express lower levels of NFE2L2 gene and/or Nrf2 protein).

As described herein, resistance of a cell to oxidative stress can be measured by various methods known in the art. In some aspects, resistance to oxidative stress can be observed by assessing whether a cell remains functional and/or viable in the presence of oxidative stress (e.g., elevated concentrations of a radical oxygen species). In certain aspects, a modified CAR-expressing cell disclosed herein can proliferate in the presence of elevated concentrations of a radical oxygen species. In some aspects, a modified CAR-expressing cell disclosed herein can express cytolytic molecules in the presence of elevated concentrations of a radical oxygen species. In certain aspects, cytolytic molecules comprise granzyme B. In further aspects, a modified CAR-expressing cell or TCR-expressing cell of the present disclosure can produce cytokines in the presence of elevated concentrations of a radical oxygen species. In some aspects, cytokines comprise IFN-γ. In some aspects, radical oxygen species comprises hydrogen peroxide ($H_2O_2$). In certain aspects, a modified CAR-expressing cell disclosed herein can (i) proliferate, (ii) express cytolytic molecules, and (iii) produce cytokines in the presence of elevated concentrations of a radical oxygen species.

To reduce the expression of NFE2L2 gene and/or Nrf2 protein in a CAR-expressing cell or a TCR-expressing cell, any methods known in the art for reducing the expression of a gene and/or protein in a cell can be used. For instance, in some aspects, the expression of NFE2L2 gene, and the Nrf2 protein encoded thereof, of a CAR-expressing cell or a TCR-expressing cell can be reduced by contacting the cell with a gene editing tool that is capable of reducing the expression levels of the NFE2L2 gene, and the Nrf2 protein encoded thereof. Non-limiting examples of the gene editing tool are shown elsewhere herein.

While the above methods for reducing the expression of NFE2L2 gene and/or Nrf2 protein is provided in the context of CAR-expressing cells, those skilled in the art will recognize that the methods disclosed herein can be used for any cells, where reducing the expression of NFE2L2 gene and/or Nrf2 protein is desired. In some aspects, a cell that can be modified (i.e., to reduce the expression of NFE2L2 gene and/or Nrf2 protein) is an immune cell. In certain aspects, the immune cell comprises a lymphocyte, neutrophil, monocyte, macrophage, dendritic cell, or combinations thereof. In some aspects, a lymphocyte comprises a T cell, tumor-infiltrating lymphocyte (TIL), lymphokine-activated killer cell, natural (NK) cell, or combinations thereof. In certain aspects, a lymphocyte is a T cell, e.g., CD4+ T cell or a CD8+ T cell. In further aspects, a lymphocyte is a tumor infiltrating lymphocyte (TIL). In certain aspects, a TIL is a CD8+ TIL. In other aspects, a TIL is a CD4+ TIL. Accordingly, in some aspects, a CAR-expressing cell that can be modified to express reduced levels of NFE2L2 gene and/or Nrf2 protein is an immune cell. In certain aspects, a CAR-expressing cell that can be modified to express reduced levels of NFE2L2 gene and/or Nrf2 protein is a T cell (i.e., CART cells). In some aspects, a CAR-expressing cell or a TCR-expressing cell that can be modified to express reduced levels of NFE2L2 gene and/or Nrf2 protein is a NK cell (i.e., CAR NK cells).

In some aspects, the contacting of the gene editing tool with a cell to be modified can occur in vivo, in vitro, ex vivo, or combinations thereof. In certain aspects, the contacting occurs in vivo (e.g., gene therapy). In other aspects, the contacting occurs in vitro. In further aspects, the contacting occurs ex vivo.

IIc. Cells with Reduced Levels of NFE2L2 Gene and/or Nrf2 Protein

In some aspects, the present disclosure provides cells, e.g., immune cells, e.g., CAR or TCR-expressing cells, wherein the cells express reduced levels of NFE2L2 gene and/or Nrf2 protein. In certain aspects, the expression of NFE2L2 gene and/or Nrf2 protein of an immune cell, e.g., a CAR-expressing cell or a TCR-expressing cell produced by the present disclosure, is reduced by at least about 5%, at least about 10%, at least about 20%, at least about 30%, at least about 40%, at least about 50%, at least about 60%, at least about 70%, at least about 80%, at least about 90%, or at least about 100%, compared to a reference cell (e.g., corresponding cell that has not been modified to express lower levels of NFE2L2 gene and/or Nrf2 protein). In some aspects, the expression of NFE2L2 gene and/or Nrf2 protein in a CAR-expressing cell or a TCR-expressing cell is completely inhibited.

In some aspects, the present disclosure is directed to a method of preparing a cell for chimeric antigen receptor or T cell receptor engineering comprises contacting the cell with a gene editing tool to reduce the expression level of NFE2L2 gene and/or Nrf2 protein in the cell. As disclosed herein the expression levels of NFE2L2 gene and/or Nrf2 protein in a CAR-expressing cell or a TCR-expressing cell can be reduced using various methods. In certain aspects, those methods comprise one or more gene editing tools described elsewhere herein. In some aspects, the expression of NFE2L2 gene, and the Nrf2 protein encoded thereof, is reduced in a CAR-expressing cell or a TCR-expressing cell by contacting the cell with a shRNA (e.g., that specific to the NFE2L2 gene). In further aspects, the expression of NFE2L2 gene, and the Nrf2 protein encoded thereof, is reduced by contacting the cell with a CRISPR (e.g., CRISPR-Cas9 system) (e.g., that specific to the NFE2L2 gene).

In some aspects, contacting a cell with a gene editing tool comprises different routes of delivery. Generally, for the gene editing tools disclosed herein to reduce the expression of NFE2L2 gene and/or Nrf2 protein in a cell, the gene editing tool must be able to enter the cell and bind to the gene of interest. In some aspects, any delivery vehicle known in the art for delivering molecules of interest to a cell can be used. See, e.g., U.S. Pat. No. 10,047,355 B2, which is herein incorporated by reference in its entirety. Additional disclosure relating to vectors that can be used are provided elsewhere in the present disclosure.

In some aspects, a method of preparing a cell for chimeric antigen receptor engineering further comprises modifying the cell to express a CAR or a TCR. In certain aspects, modifying the cell to express a CAR or TCR comprises contacting the cell with a nucleic acid sequence encoding the CAR. In some aspects, the nucleic acid sequence encoding the CAR is expressed from a vector (e.g., expression vector).

In some aspects, CARs or TCRs that can be expressed on a modified cell disclosed herein target one or more antigens expressed on a tumor cell, such as a malignant B cell, a malignant T cell, or malignant plasma cell. In certain aspects, a CAR can target an antigen selected from CD2, CD3ε, CD4, CD5, CD7, CD19, TRAC, TCRβ, BCMA, CLL-1, CS1, CD38, the extracellular portion of the APRIL protein, or combinations thereof. Other non-limiting examples of antigens that a CAR can bind to include TSHR, CD123, CD22, CD30 CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-I3Ra2, Mesothelin, IL-HRa, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gplOO, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WTl, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, NL-IAP, ERG (TMPRSS2 ETS fusion gene), NA17, PAX3, Androgen receptor, Cyclin BI, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, and any combinations thereof.

In certain aspects, a modified cell of the present disclosure can express a T cell receptor (TCR) targeting a tumor antigen. T-cell receptor is a heterodimer composed of 2 different transmembrane polypeptide chains: an α chain and a β chain, each consisting of a constant region, which anchors the chain inside the T-cell surface membrane, and a variable region, which recognizes and binds to the antigen presented by MHCs. The TCR complex is associated with 6 polypeptides forming 2 heterodimers, CD3γε and CD3δε, and 1 homodimer CD3ζ, which together forms the CD3 complex. T-cell receptor-engineered T-cell therapy utilizes the modification of T cells that retain these complexes to specifically target the antigens expressed by particular tumor cells.

In some aspects, the modified TCR engineered cells can target main types: shared tumor-associated antigens (shared TAAs) and unique tumor-associated antigens (unique TAAs), or tumor-specific antigens. The former can include, without any limitation, cancer-testis (CT) antigens, overexpressed antigens, and differentiation antigens, while the latter can include, without any limitation, neoantigens and oncoviral antigens. Human papillomavirus (HPV) E6 protein and HPV E7 protein belong to the category of oncoviral antigens.

In some aspects, the modified TCR engineered cells can target a CT antigen, e.g., melanoma-associated antigen (MAGE) including, but not limited to, MAGE-A1, MAGE-A2, MAGE-A3, MAGE-A4, MAGE-A6, MAGE-A8, MAGE-A9.23, MAGE-A10, and MAGE-A12. In some aspects, the modified TCR engineered cells can target glycoprotein (gp100), melanoma antigen recognized by T cells (MART-1), and/or tyrosinase, which are mainly found in melanomas and normal melanocytes. In some aspects, the modified TCR engineered cells can target Wilms tumor 1 (WT1), i.e., one kind of overexpressed antigen that is highly expressed in most acute myeloid leukemia (AML), acute lymphoid leukemia, almost every type of solid tumor and several critical tissues, such as heart tissues. In some aspects, the modified TCR engineered cells can target mesothelin, another kind of overexpressed antigen that is highly expressed in mesothelioma but is also present on mesothelial cells of several tissues, including trachea.

In some aspects, the modified TCR engineered cells can target any neoantigen, which can be formed by random somatic mutations specific to individual tumors.

In some aspects, a modified immune cell of the present disclosure, e.g., a CAR T or NK cells or a TCR-engineered T cell, can target any one of the tumor antigens. Non-limiting examples of the antigens that the modified TCR engineered cells can target include CD2, CD3ε, CD4, CD5, CD7, CD19, TRAC, TCRβ, BCMA, CLL-1, CS1, CD38, the extracellular portion of the APRIL protein, TSHR, CD123, CD22, CD30, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, Mesothelin, IL-l lRa, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gplOO, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin Bl, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, and any combinations thereof.

In some aspects, a cell that can be prepared to express a CAR or a TCR comprises an immune cell. In certain aspects, an immune cell comprises a lymphocyte, neutrophil, monocyte, macrophage, dendritic cell, or combinations thereof. In some aspects, an immune cell is a lymphocyte. In certain aspects, a lymphocyte comprises a T cell, tumor-infiltrating lymphocyte (TIL), lymphokine-activated killer cell, natural killer (NK) cell, or combinations thereof. In some aspects, an immune cell that can be prepared to express a CAR is a T cell (CAR T cell), e.g., CD8+ T cell or CD4+ T cell. In certain aspects, the T cells are natural killer T cells (NKT cells). In further aspects, an immune cell is a NK cell (CAR NK cell).

In some aspects, a CAR-expressing cell disclosed herein is a CAR T cell. In certain aspects, the CAR T cell is a mono CAR T cell. In further aspects, the CAR T cell is a genome-edited CAR T cell. In certain aspects, the CAR T cell is a dual CAR T cell. In some aspects, the CAR T cell is a tandem CAR T cell. In some aspects, a CAR-expressing cell disclosed herein is a CAR NKT cell. In certain aspects, the CAR NKT cell is a mono CAR NKT cell. In further aspects, the CAR NKT cell is a dual CAR NKT cell. In some aspects, the CAR NKT cell is a tandem CAR NKT cell. Examples of such CAR T cells and CAR NKT cells are provided in International Application No. PCT/US2019/044195.

In some aspects, a gene editing tool disclosed herein is expressed from a vector comprising a nucleic acid sequence encoding the gene editing tool. In certain aspects, the nucleic acid sequence encoding the gene editing tool and the nucleic acid sequence encoding the CAR or TCR are on separate vectors. In further aspects, the nucleic acid sequence encoding the gene editing tool and the nucleic acid sequence encoding the CAR or TCR are on the same vector.

As described herein, CAR or TCR-expressing cells produced by the methods disclosed herein (i.e., expressing reduced levels of NFE2L2 gene and/or Nrf2 protein) can exhibit improved properties. For example, in certain aspects, a CAR or TCR-expressing cell produced herein can exhibit greater effector activity compared to a reference cell (e.g., CAR or TCR-expressing cell that has not been modified to express lower levels of NFE2L2 gene and/or Nrf2 protein). In some aspects, a CAR or TCR-expressing cell disclosed herein (i.e., expressing reduced levels of NFE2L2 gene and/or Nrf2 protein) produce increased amount of IFN-γ when stimulated with an antigen, such as a cognate antigen (e.g., tumor antigen). In some aspects, the amount of IFN-γ produced is increased by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, or at least about 300% or more compared to a reference cell (e.g., CAR or TCR-expressing cell that has not been modified to express lower levels of NFE2L2 gene and/or Nrf2 protein).

In some aspects, the CAR or TCR-expressing cells of the present disclosure exhibit increased resistance to oxidative stress compared to a reference cell (e.g., CAR or TCR-expressing cell that has not been modified to express lower levels of NFE2L2 gene and/or Nrf2 protein). In certain aspects, CAR or TCR-expressing cells described herein can proliferate in the presence of elevated concentrations of a radical oxygen species. In further aspects, a CAR or TCR-expressing cell disclosed herein can express cytolytic molecules in the presence of elevated concentrations of a radical oxygen species. In certain aspects, cytolytic molecules comprise granzyme B. In some aspects, a CAR or TCR-expressing cell produced by the methods described herein can produce cytokines (e.g., IFN-γ) in the presence of elevated concentrations of a radical oxygen species. In some aspects, radical oxygen species comprises hydrogen peroxide ($H_2O_2$).

IId. Gene Editing Tools

One or more gene editing tools can be used to modify the cells of the present disclosure. Non-limiting examples of the gene editing tools are disclosed below:

CRISPR/Cas System

In some aspects, the gene editing tool that can be used in the present disclosure comprises a CRISPR/Cas system. Such systems can employ, for example, a Cas9 nuclease, which in some instances, is codon-optimized for the desired cell type in which it is to be expressed (e.g., T cells, e.g., CAR-expressing T cells). Such systems can also employ a guide RNA (gRNA) that comprises two separate molecules. In certain aspects, the two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA" or "scaffold") molecule.

A crRNA comprises both the DNA-targeting segment (single stranded) of the gRNA and a stretch of nucleotides that forms one half of a double stranded RNA (dsRNA) duplex of the protein-binding segment of the gRNA. A corresponding tracrRNA (activator-RNA) comprises a stretch of nucleotides that forms the other half of the dsRNA duplex of the protein-binding segment of the gRNA. Thus, a stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. The crRNA additionally provides the single stranded DNA-targeting segment. Accordingly, a gRNA comprises a sequence that hybridizes to a target sequence (e.g., Nrf2 mRNA), and a tracrRNA. Thus, a crRNA and a tracrRNA (as a corresponding pair) hybridize to form a gRNA. If used for modification within a cell, the exact sequence and/or length of a given crRNA or tracrRNA molecule can be designed to be specific to the species in which the RNA molecules will be used (e.g., humans).

Naturally occurring genes encoding the three elements (Cas9, tracrRNA and crRNA) are typically organized in operon(s). Naturally occurring CRISPR RNAs differ depending on the Cas9 system and organism but often contain a targeting segment of between 21 to 72 nucleotides length, flanked by two direct repeats (DR) of a length of between 21 to 46 nucleotides (see, e.g., WO2014/131833). In the case of S. pyogenes, the DRs are 36 nucleotides long and the targeting segment is 30 nucleotides long. The 3' located DR is complementary to and hybridizes with the corresponding tracrRNA, which in turn binds to the Cas9 protein.

Alternatively, a CRISPR system used herein can further employ a fused crRNA-tracrRNA construct (i.e., a single transcript) that functions with the codon-optimized Cas9. This single RNA is often referred to as a guide RNA or gRNA. Within a gRNA, the crRNA portion is identified as the "target sequence" for the given recognition site and the tracrRNA is often referred to as the "scaffold." Briefly, a short DNA fragment containing the target sequence is inserted into a guide RNA expression plasmid. The gRNA expression plasmid comprises the target sequence (in some aspects around 20 nucleotides), a form of the tracrRNA sequence (the scaffold) as well as a suitable promoter that is active in the cell and necessary elements for proper processing in eukaryotic cells. Many of the systems rely on custom, complementary oligos that are annealed to form a double stranded DNA and then cloned into the gRNA expression plasmid.

The gRNA expression cassette and the Cas9 expression cassette are then introduced into the cell. See, for example, Mali P et al., (2013) *Science* 2013 Feb. 15; 339(6121):823-6; Jinek M et al., *Science* 2012 Aug. 17; 337(6096):816-21; Hwang W Y et al., *Nat Biotechnol* 2013 March; 31(3):227-9; Jiang W et al., *Nat Biotechnol* 2013 March; 31(3):233-9; and Cong L et al., *Science* 2013 Feb. 15; 339(6121):819-23, each of which is herein incorporated by reference in its entirety. See also, for example, WO/2013/176772 A1, WO/2014/065596 A1, WO/2014/089290 A1, WO/2014/093622 A2, WO/2014/099750 A2, and WO/2013142578 A1, each of which is herein incorporated by reference in its entirety.

In some aspects, the Cas9 nuclease can be provided in the form of a protein. In some aspects, the Cas9 protein can be provided in the form of a complex with the gRNA. In other aspects, the Cas9 nuclease can be provided in the form of a nucleic acid encoding the protein. The nucleic acid encoding the Cas9 nuclease can be RNA (e.g., messenger RNA (mRNA)) or DNA. In some aspects, the gRNA can be provided in the form of RNA. In other aspects, the gRNA can be provided in the form of DNA encoding the RNA. In some aspects, the gRNA can be provided in the form of separate crRNA and tracrRNA molecules, or separate DNA molecules encoding the crRNA and tracrRNA, respectively.

In some aspects, the gRNA comprises a third nucleic acid sequence encoding a Clustered Regularly Interspaced Short Palindromic Repeats (CRISPR) RNA (crRNA) and a trans-activating CRISPR RNA (tracrRNA). In certain aspects, the Cas protein is a type I Cas protein. In further aspects, the Cas protein is a type II Cas protein. In certain aspects, the type II Cas protein is Cas9. In some aspects, the type II Cas, e.g., Cas9, is a human codon-optimized Cas.

In some aspects, the Cas protein is a "nickase" that can create single strand breaks (i.e., "nicks") within the target nucleic acid sequence without cutting both strands of double stranded DNA (dsDNA). Cas9, for example, comprises two nuclease domains—a RuvC-like nuclease domain and an HNH-like nuclease domain—which are responsible for cleavage of opposite DNA strands. Mutation in either of these domains can create a nickase. Examples of mutations creating nickases can be found, for example, WO/2013/176772 A1 and WO/2013/142578 A1, each of which is herein incorporated by reference.

In certain aspects, two separate Cas proteins (e.g., nickases) specific for a target site on each strand of dsDNA can create overhanging sequences complementary to overhanging sequences on another nucleic acid, or a separate region on the same nucleic acid. The overhanging ends created by contacting a nucleic acid with two nickases specific for target sites on both strands of dsDNA can be either 5' or 3' overhanging ends. For example, a first nickase can create a single strand break on the first strand of dsDNA, while a second nickase can create a single strand break on the second strand of dsDNA such that overhanging sequences are created. The target sites of each nickase creating the single strand break can be selected such that the overhanging end sequences created are complementary to overhanging end sequences on a different nucleic acid molecule. The complementary overhanging ends of the two different nucleic acid molecules can be annealed by the methods disclosed herein. In some aspects, the target site of the nickase on the first strand is different from the target site of the nickase on the second strand.

TALEN

In some aspects, a gene editing tool that can be used to edit (e.g., reduce or inhibit) the expression of NFE2L2 gene and/or Nrf2 protein is a nuclease agent, such as a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI.

The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al., (2010) PNAS 10.1073/pnas.1013133107; Scholze & Boch (2010) Virulence 1:428-432; Christian et al., *Genetics* (2010) 186:757-761; Li et al., (2010) *Nuc. Acids Res.* (2010) doi:10.1093/nar/gkq704; and Miller et al., (2011) *Nature Biotechnology* 29:143-148; all of which are herein incorporated by reference in their entirety.

Non-limiting examples of suitable TAL nucleases, and methods for preparing suitable TAL nucleases, are disclosed, e.g., in US Patent Application No. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1 (each hereby incorporated by reference).

In various aspects, TAL effector nucleases are engineered that cut in or near a target nucleic acid sequence in, e.g., a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In some aspects, each monomer of the TALEN comprises 12-25 TAL repeats, wherein each TAL repeat binds a 1 bp subsite. In certain aspects, the nuclease agent is a chimeric protein comprising a TAL repeat-based DNA binding domain operably linked to an independent nuclease. In further aspects, the independent nuclease is a FokI endonuclease. In some aspects, the nuclease agent comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by about 6 bp to about 40 bp cleavage site, and wherein the FokI nucleases dimerize and make a double strand break at a target sequence.

In some aspects, the nuclease agent comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by a 5 bp or 6 bp cleavage site, and wherein the FokI nucleases dimerize and make a double strand break.

Zinc Finger Nuclease (ZFN)

In some aspects, a gene editing tool useful for the present disclosure includes a nuclease agent, such as a zinc-finger nuclease (ZFN) system. Zinc finger-based systems comprise a fusion protein comprising two protein domains: a zinc finger DNA binding domain and an enzymatic domain. A "zinc finger DNA binding domain", "zinc finger protein", or "ZFP" is a protein, or a domain within a larger protein, that binds DNA in a sequence-specific manner through one or more zinc fingers, which are regions of amino acid sequence within the binding domain whose structure is stabilized through coordination of a zinc ion. The zinc finger domain, by binding to a target DNA sequence (e.g., NFE2L2), directs the activity of the enzymatic domain to the vicinity of the sequence and, hence, induces modification of the endogenous target gene in the vicinity of the target sequence. A zinc finger domain can be engineered to bind to virtually any desired sequence. As disclosed herein, in some aspects, the zinc finger domain binds a DNA sequence that encodes the Nrf2 protein. Accordingly, after identifying a target genetic locus containing a target DNA sequence at which cleavage or recombination is desired (e.g., a target locus in a target gene referenced in Table 1), one or more zinc finger binding domains can be engineered to bind to one or more target DNA sequences in the target genetic locus. Expression of a fusion protein comprising a zinc finger binding domain and an enzymatic domain in a cell, effects modification in the target genetic locus.

In some aspects, a zinc finger binding domain comprises one or more zinc fingers. Miller et al., (1985) EMBO J. 4:1609-1614; Rhodes (1993) Scientific American February: 56-65; U.S. Pat. No. 6,453,242. Typically, a single zinc finger domain is about 30 amino acids in length. An individual zinc finger binds to a three-nucleotide (i.e., triplet) sequence (or a four-nucleotide sequence which can overlap, by one nucleotide, with the four-nucleotide binding site of an adjacent zinc finger). Therefore, the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. Binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain. In some aspects, the DNA-binding domains of individual ZFNs comprise between three and six individual zinc finger repeats and can each recognize between 9 and 18 basepairs.

Zinc finger binding domains can be engineered to bind to a sequence of choice. See, for example, Beerli et al., (2002) *Nature Biotechnol.* 20:135-141; Pabo et al., (2001) *Ann. Rev. Biochem.* 70:313-340; Isalan et al., (2001) *Nature Biotechnol.* 19:656-660; Segal et al., (2001) *Curr. Opin. Biotechnol.* 12:632-637; Choo et al., (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection.

Selection of a target DNA sequence for binding by a zinc finger domain can be accomplished, for example, according to the methods disclosed in U.S. Pat. No. 6,453,242. It will be clear to those skilled in the art that simple visual inspection of a nucleotide sequence can also be used for selection of a target DNA sequence. Accordingly, any means for target DNA sequence selection can be used in the methods described herein. A target site generally has a length of at least 9 nucleotides and, accordingly, is bound by a zinc finger binding domain comprising at least three zinc fingers. However, binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

The enzymatic domain portion of the zinc finger fusion proteins can be obtained from any endo- or exonuclease. Exemplary endonucleases from which an enzymatic domain can be derived include, but are not limited to, restriction endonucleases and homing endonucleases. See, for example, 2002-2003 Catalogue, New England Biolabs, Beverly, Mass.; and Belfort et al., (1997) *Nucleic Acids Res.* 25:3379-3388. Additional enzymes which cleave DNA are known (e.g., 51 Nuclease; mung bean nuclease; pancreatic DNaseI; micrococcal nuclease; yeast HO endonuclease; see also Linn et al., (eds.) Nucleases, Cold Spring Harbor Laboratory Press, 1993). One or more of these enzymes (or functional fragments thereof) can be used as a source of cleavage domains.

Exemplary restriction endonucleases (restriction enzymes) suitable for use as an enzymatic domain of the ZFPs described herein are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487, 994; as well as Li et al., (1992) *Proc. Natl. Acad. Sci. USA* 89:4275-4279; Li et al., (1993) *Proc. Natl. Acad. Sci. USA* 90:2764-2768; Kim et al., (1994a) *Proc. Natl. Acad. Sci. USA* 91:883-887; Kim et al., (1994b) *J. Biol. Chem.* 269: 31,978-31,982. Thus, in some aspects, fusion proteins comprise the enzymatic domain from at least one Type IIS restriction enzyme and one or more zinc finger binding domains.

An exemplary Type IIS restriction enzyme, whose cleavage domain is separable from the binding domain, is FokI. This particular enzyme is active as a dimer. Bitinaite et al., (1998) *Proc. Natl. Acad. Sci. USA* 95: 10,570-10,575. Thus, for targeted double-stranded DNA cleavage using zinc finger-FokI fusions, two fusion proteins, each comprising a FokI enzymatic domain, can be used to reconstitute a catalytically active cleavage domain. Alternatively, a single polypeptide molecule containing a zinc finger binding domain and two FokI enzymatic domains can also be used. Exemplary ZFPs comprising FokI enzymatic domains are described in U.S. Pat. No. 9,782,437.

Meganuclease

In some aspects, a gene editing tool that be used to regulate Nrf2 expression in a cell includes a nuclease agent such as a meganuclease system. Meganucleases have been classified into four families based on conserved sequence motifs, the families are the "LAGLIDADG," "GIY-YIG," "H-N-H," and "His-Cys box" families. These motifs participate in the coordination of metal ions and hydrolysis of phosphodiester bonds.

HEases are notable for their long recognition sites, and for tolerating some sequence polymorphisms in their DNA substrates. Meganuclease domains, structure and function are known, see, for example, Guhan and Muniyappa (2003) *Crit Rev Biochem Mol Biol* 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764.

In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) *Nucleic Acids Res* 31:2952-62; Chevalier et al., (2002) *Mol Cell* 10:895-905; Gimble et al., (2003) *Mol Biol* 334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800; Chames et al., (2005) *Nucleic Acids Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346; each of which is herein incorporated by reference in its entirety.

Any meganuclease can be used herein, including, but not limited to, I-SceI, I-SceII, I-SceIII, I-SceIV, I-SceV, I-SecVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP, PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

In some aspects, the meganuclease recognizes double-stranded DNA sequences of 12 to 40 base pairs. In some aspects, the meganuclease recognizes one perfectly matched target sequence in the genome. In some aspects, the meganuclease is a homing nuclease. In some aspects, the homing nuclease is a "LAGLIDADG" family of homing nuclease. In some aspects, the "LAGLIDADG" family of homing nuclease is selected from I-SceI, I-CreI, I-Dmol, or combinations thereof.

Restriction Endonuclease

In some aspects, a gene editing tool useful for the present disclosure includes a nuclease agent such as a restriction endonuclease, which includes Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) *Nucleic Acids Res* 31:418-20), Roberts et al., (2003) *Nucleic Acids Res* 31:1805-12, and Belfort et al., (2002) in Mobile DNA II, pp. 761-783, Eds. Craigie et al., (ASM Press, Washington, D.C.).

As described herein, in some aspects, a gene editing tool (e.g., CRISPR, TALEN, meganuclease, restriction endonuclease, RNAi, antisense oligonucleotides) can be introduced into the cell by any means known in the art. In certain aspects, the polypeptide encoding the particular gene editing tool can be directly introduced into the cell. Alternatively, a polynucleotide encoding the gene editing tool can be introduced into the cell. In some aspects, when a polynucleotide encoding the gene editing tool is introduced into the cell, the gene editing tool can be transiently, conditionally or constitutively expressed within the cell. Thus, the polynucleotide encoding the gene editing tool can be contained in an expression cassette and be operably linked to a conditional promoter, an inducible promoter, a constitutive promoter, or a tissue-specific promoter. Alternatively, the gene editing tool is introduced into the cell as an mRNA encoding or comprising the gene editing tool.

RNAi

In some aspects, a gene editing tool that can be used to reduce the expression of Nrf2 in a cell includes an RNA interference molecule ("RNAi"). As used herein, RNAi are RNA polynucleotide that mediates the decreased the expression of an endogenous target gene product by degradation of a target mRNA through endogenous gene silencing pathways (e.g., Dicer and RNA-induced silencing complex (RISC)). Non-limiting examples of RNAi agents include micro RNAs (also referred to herein as "miRNAs"), short hair-pin RNAs (shRNAs), small interfering RNAs (siRNAs), RNA aptamers, or combinations thereof.

In some aspects, the gene editing tools useful for the present disclosure comprises one or more miRNAs. "miRNAs" refer to naturally occurring, small non-coding RNA molecules of about 21-25 nucleotides in length. In some aspects, the miRNAs useful for the present disclosure are at least partially complementary to a Nrf2 mRNA molecule. miRNAs can downregulate (e.g., decrease) expression of an endogenous target gene product (i.e., Nrf2 protein) through translational repression, cleavage of the mRNA, and/or deadenylation.

In some aspects, a gene editing tool that can be used with the present disclosure comprises one or more shRNAs. "shRNAs" (or "short hairpin RNA" molecules) refer to an RNA sequence comprising a double-stranded region and a loop region at one end forming a hairpin loop, which can be used to reduce and/or silence a gene expression. The double-stranded region is typically about 19 nucleotides to about 29 nucleotides in length on each side of the stem, and the loop region is typically about three to about ten nucleotides in length (and 3'- or 5'-terminal single-stranded overhanging nucleotides are optional). shRNAs can be cloned into plasmids or in non-replicating recombinant viral vectors to be introduced intracellularly and result in the integration of the shRNA-encoding sequence into the genome. As such, an shRNA can provide stable and consistent repression of endogenous target gene (i.e., Nrf2) translation and expression.

In some aspects, a gene editing tool disclosed herein comprises one or more siRNAs. "siRNAs" refer to double stranded RNA molecules typically about 21-23 nucleotides in length. The siRNA associates with a multi protein complex called the RNA-induced silencing complex (RISC), during which the "passenger" sense strand is enzymatically cleaved. The antisense "guide" strand contained in the activated RISC then guides the RISC to the corresponding mRNA because of sequence homology and the same nuclease cuts the target mRNA (i.e., Nrf2 mRNA), resulting in specific gene silencing. In certain aspects, an siRNA is 18, 19, 20, 21, 22, 23 or 24 nucleotides in length and has a 2 base overhang at its 3' end. siRNAs can be introduced to an individual cell and/or culture system and result in the degradation of target mRNA sequence (i.e., Nrf2 mRNA). siRNAs and shRNAs are further described in Fire et al., *Nature* 391:19, 1998 and U.S. Pat. Nos. 7,732,417; 8,202, 846; and 8,383,599; each of which is herein incorporated by reference in its entirety.

Antisense Oligonucleotides

In some aspects, a gene editing tool that can be used to reduce the expression of Nrf2 in a cell includes antisense oligonucleotides. As used herein, "antisense oligonucleotide" or "ASO" refer to an oligonucleotide capable of modulating expression of a target gene (i.e., Nrf2) by hybridizing to a target nucleic acid, in particular to a contiguous sequence on a target nucleic acid. Antisense oligonucleotides are not essentially double stranded and are therefore not siRNAs or shRNAs.

In some aspects, ASOs useful for the present disclosure are single stranded. It is understood that single stranded oligonucleotides of the present disclosure can form hairpins or intermolecular duplex structures (duplex between two molecules of the same oligonucleotide), as long as the degree of intra or inter self-complementarity is less than approximately 50% across of the full length of the oligonucleotide. In some aspects, ASOs useful for the present disclosure can comprise one or more modified nucleosides or nucleotides, such as 2' sugar modified nucleosides. Additional modifications that can be made to an ASO (e.g., such as those that can be used to inhibit or reduce Nrf2 expression) are provided in, e.g., US Publ. No. 2019/0275148 A1.

In some aspects, ASOs can reduce the expression of Nrf2 protein via nuclease mediated degradation of the Nrf2 transcript (e.g., mRNA), where the ASOs are capable of recruiting a nuclease, e.g., RNase H, such as RNaseH1. RNase H is a ubiquitous enzyme that hydrolyzes the RNA strand of an RNA/DNA duplex. Accordingly, in certain aspects, once bound to the target sequence (e.g., Nrf2 mRNA), ASOs can induce the degradation of the Nrf2 mRNA and thereby, reduce the expression of Nrf2 protein.

In some aspects, an ASO comprises one or more morpholinos. "Morpholino," as used herein, refers to a modified nucleic acid oligomer wherein standard nucleic acid bases are bound to morpholine rings and are linked through phosphorodiamidate linkages. Similar to siRNA and shRNA, morpholinos bind to complementary mRNA sequences. However, morpholinos function through steric-inhibition of mRNA translation and alteration of mRNA splicing rather than targeting complementary mRNA sequences for degradation.

As disclosed herein, the above examples of gene editing tools are not intended to be limiting and any gene editing tool available in the art can be used to reduce or inhibit the expression of NFE2L2 gene and/or Nrf2 protein.

III. Nucleic Acids and Vectors

Further aspect described herein pertains to one or more nucleic acid molecules that comprise a gene editing tool for reducing the expression of NFE2L2 gene and/or Nrf2 protein in a cell and/or that encode a chimeric antigen receptor or a T cell receptor that can be expressed in the modified cell of the present disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and can or cannot contain intronic sequences. In certain aspects, the nucleic acid is a cDNA molecule. Nucleic acids described herein can be obtained using standard molecular biology techniques known in the art.

In some aspects, the present disclosure provides a vector comprising an isolated nucleic acid molecule comprising a gene editing tool for reducing the expression of NFE2L2 gene and/or Nrf2 protein in a cell and/or that encode a chimeric antigen receptor or a T cell receptor that can be expressed in the modified cell of the present disclosure. As described herein, such vectors can be used to modify a cell (e.g., CAR-expressing cells) to express reduced levels of NFE2L2 gene and/or Nrf2 protein, wherein such modified cells can be used to treat a disease or disorder, such as cancer.

Suitable vectors for the disclosure include expression vectors, viral vectors, and plasmid vectors. In some aspects, the vector is a viral vector.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

As used herein, viral vectors include, but are not limited to, nucleic acid sequences from the following viruses: retrovirus, such as Moloney murine leukemia virus, Harvey murine sarcoma virus, murine mammary tumor virus, and Rous sarcoma virus; lentivirus; adenovirus; adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA.

In some aspects, a vector is derived from an adeno-associated virus. In other aspects, a vector is derived from a lentivirus. Examples of the lentiviral vectors are disclosed in WO9931251, WO9712622, WO9817815, WO9817816, and WO9818934, each which is incorporated herein by reference in its entirety.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, CA.). Other plasmids are well-known to those of ordinary skill in the art. Additionally, plasmids can be custom designed using standard molecular biology techniques to remove and/or add specific fragments of DNA.

IV. Pharmaceutical Compositions

Further provided herein are compositions comprising a cell which has been modified to express reduced levels of NFE2L2 gene and/or Nrf2 protein (e.g., such as those cells described herein) and a pharmaceutically acceptable carrier, excipient, or stabilizer. As described herein, such pharmaceutical compositions can be used to prevent and/or treat a cancer. As described herein, in some aspects, the modified cell present in a pharmaceutical composition disclosed herein is an immune cell, such as a T cell (e.g., CAR or TCR-expressing T cells) or NK cells (e.g., CAR or TCR-expressing NK cells).

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

A pharmaceutical composition can be formulated for any route of administration to a subject. Specific examples of routes of administration include intramuscularly, subcutaneously, ophthalmic, intravenously, intraperitoneally, intradermally, intraorbitally, intracerebrally, intracranially, intraspinally, intraventricular, intrathecally, intracisternally, intracapsularly, or intratumorally. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutical compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, each of which is herein incorporated by reference in its entirety.

The compositions to be used for in vivo administration can be sterile. This is readily accomplished by filtration through, e.g., sterile filtration membranes.

All references, patents or applications, U.S. or foreign, cited in the application are hereby incorporated by reference as if written herein in their entireties. Where any inconsistencies arise, material literally disclosed herein controls.

EXAMPLES

The present disclosure will be described in detail below with reference to examples. It should be understood that the described examples are intended to merely exemplify, instead of limiting, the present disclosure.

Figure 2:
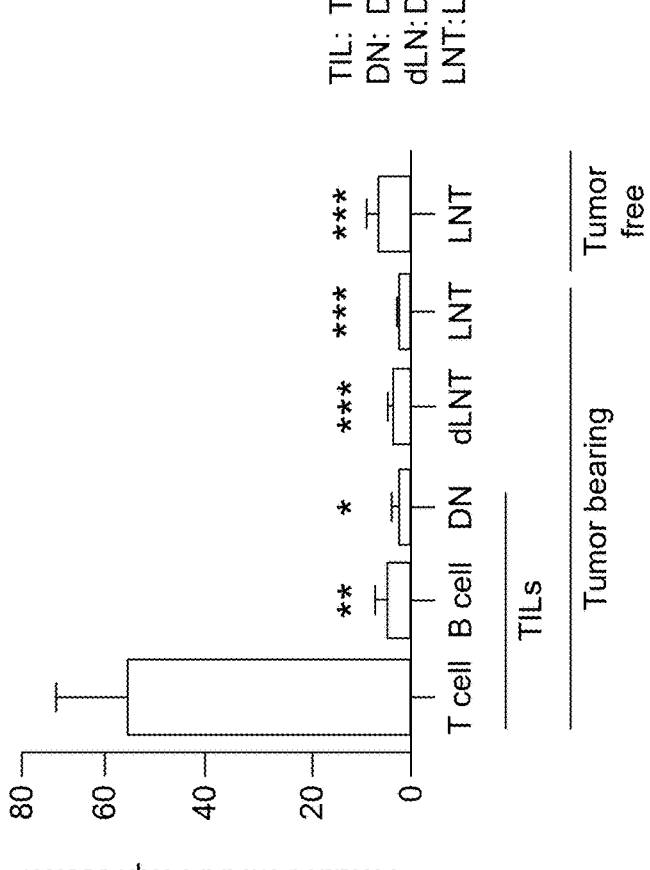
FIG. 2 shows the Nrf2 mRNA expression in different cell populations isolated from tissues of tumor-bearing and -free mice. The different cells shown include (from left to right): (i) tumor-infiltrating T cells (from tumor-bearing mice); (ii) tumor-infiltrating B cells (from tumor-bearing mice); (iii) non-T and non-B TILs (DN) (from tumor-bearing mice); (iv) T cells from draining lymph nodes ("dLN") (from tumor-bearing mice); (v) T cells from non-draining lymph nodes (from tumor-bearing mice); (vi) T cells from non-draining lymph nodes (from tumor-free mice).

Example 1. Determination of the Nrf2 mRNA Expression Level in Tumor-Infiltrating T Cells The level of nuclear factor E2 factor related-factor 2 (Nrf2) mRNA expression in tumor-infiltrating T cells was determined. Nrf2 plays an important role in protecting cells from oxidative stress-mediated damage. To better understand the relationship between Nrf2 and oxidative stress, T cells were treated with varying concentrations of hydrogen peroxide, a known inducer of oxidative stress. As shown in FIG. 1, with increase in oxidative stress (i.e., higher concentration of H2O2), T cells expressed higher levels of Nrf2 mRNA. [0018] Nearly all cancers are associated with elevated oxidative stress. To better understand this phenomenon, T cells from tumors and/or different lymph nodes were isolated from tumor bearing mice. As a control, T cells from the lymph nodes of healthy mice were also isolated. As shown in FIG. 2, the level of Nrf2 mRNA expression in tumor-infiltrating T cells was very high compared with those in draining Lymph Nodes (dLNs) or any other T cell of lymph node in the tumor-bearing mice. This result demonstrates the selectivity of the Nrf2 expression in tumor infiltrating T lymphocytes.

Example 2. Determination of Anticancer Reaction that Changed with Modulation of Nrf2 Expression To begin understanding how modulating Nrf2 expression can affect anti-tumor immune response, an Nrf2-deleted mouse was prepared for in vivo determination of T cell-mediated anticancer reaction that changed with modulation of Nrf2 expression.

2-1. Determination of the Ability to Inhibit Cancer Cell Proliferation

In order to determine the ability to inhibit cancer cell proliferation along with changes in modulation of Nrf2 expression, cancer cells were injected into the Nrf2-deleted mouse and a wild-type mouse, and then tumor volumes were measured. Specifically, melanoma (B16) cells were injected into the Nrf2-deleted mouse and the wild-type mouse; then, the proliferation of the cancer cells was observed by measuring tumor volume at various time points post tumor inoculation. The results are shown in FIGS. 3 and 4.

Figure 3:
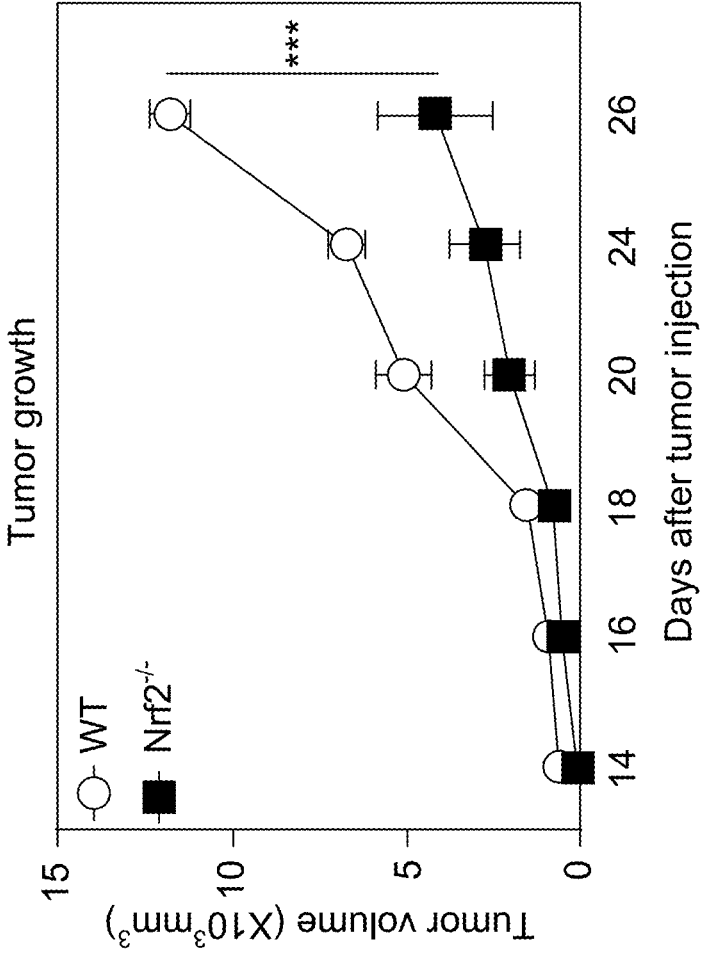
FIG. 3 shows melanoma growth rate in Nrf2 deficient and WT mice. Specifically, FIG. 3 provides a comparison of tumor growth in Nrf2−/− mice and wild-type mice (i.e., expressing normal levels of Nrf2) at different time points post tumor (i.e., melanoma) inoculation.
Figure 4:
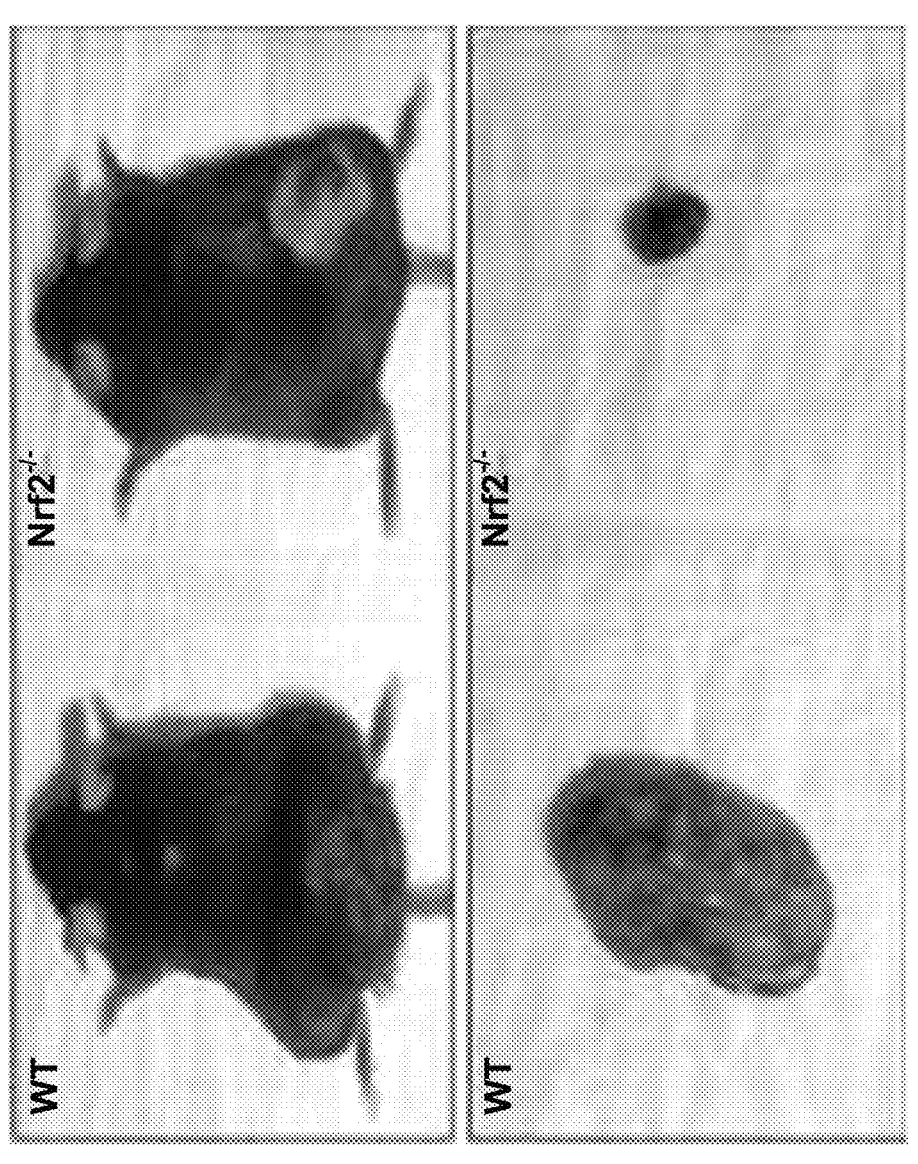
FIG. 4 shows an image of the melanoma proliferation (i.e., growth) that changed with Nrf2 expression. Specifically, FIG. 4 provides an image of the melanoma tumor isolated from wild-type (left) and Nrf2−/− (right) mice.

As shown in FIGS. 3 and 4, after injection of the melanoma cells, a significant effect of inhibiting the cancer cell proliferation was observed in the Nrf2-deleted mouse. For instance, by about day 19 post tumor inoculation, there was a significant difference in tumor volume between the wild-type and Nrf2-/- animals.

To confirm that the observed anti-tumor effect was not unique to melanoma, lymphoma cells were injected into the Nrf2-deleted mouse and the wild-type mouse; then, the proliferation of the cancer cells was again observed by measuring tumor volume at various time points post tumor inoculation. The results are shown in FIGS. 5 and 6.

Figure 5:
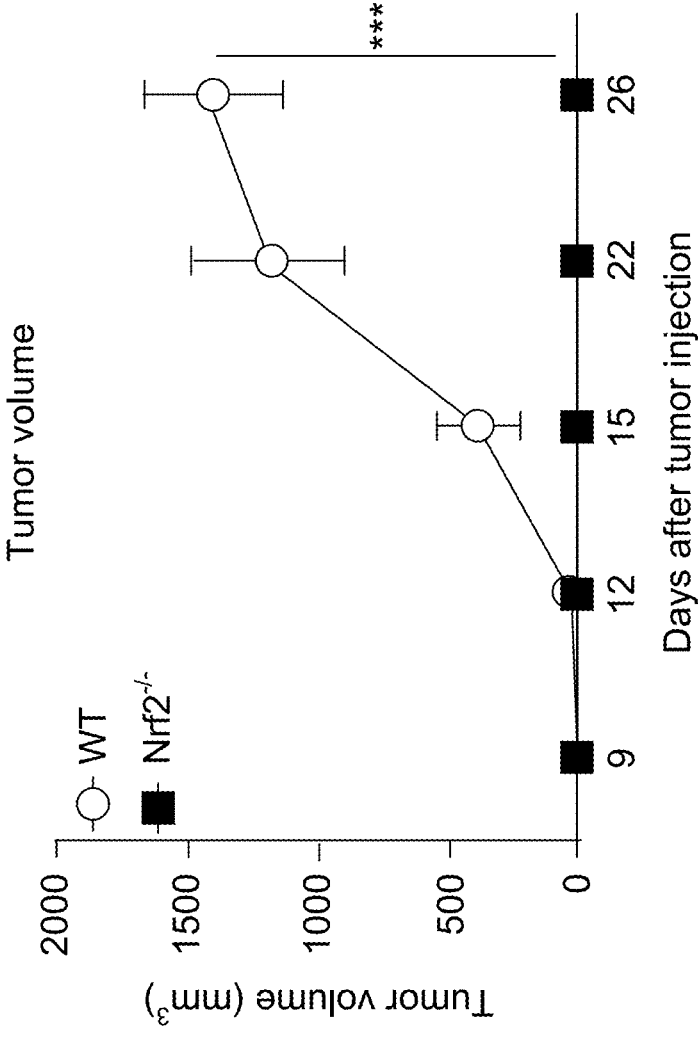
FIG. 5 shows lymphoma proliferation that changed with Nrf2 expression. Specifically, FIG. 5 provides a comparison of tumor volume in Nrf2−/− mice and wild-type mice (i.e., expressing normal levels of Nrf2) at different time points post tumor (i.e., lymphoma) inoculation.
Figure 6:
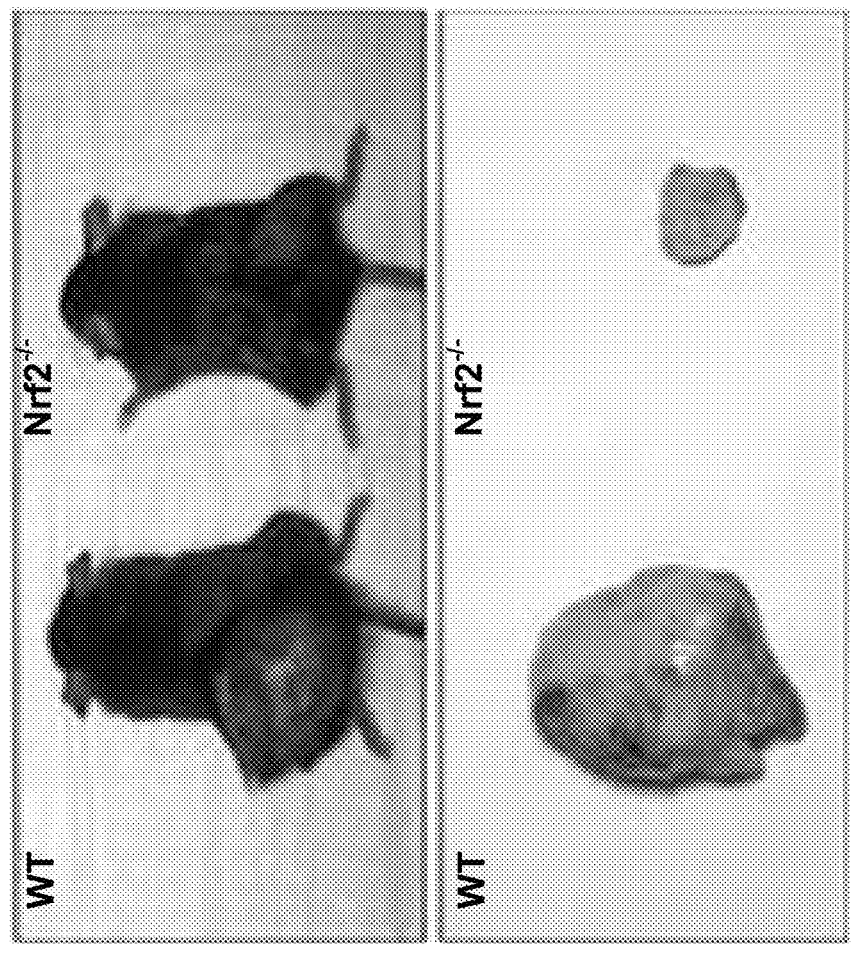
FIG. 6 shows an image of the lymphoma proliferation (i.e., growth) that changed with Nrf2 expression. Specifically, FIG. 6 provides an image of the lymphoma tumor isolated from wild-type (left) and Nrf2−/− (right) mice.

As shown in FIGS. 5 and 6, after injection of the lymphoma cells, a significant effect of inhibiting the cancer cell proliferation was observed in the Nrf2-deleted mouse, in which the tumor volume had greatly decreased.

2-2. Determination of the Ability to Inhibit Cancer Cell Metastasis

Next, in order to determine the ability to inhibit cancer cell metastasis along with changes in modulation of Nrf2 expression, lung carcinoma cells were injected (intravenously) into the Nrf2-deleted mouse and the wild-type mouse; then, the cancer cell metastasis was observed. The result is shown in FIG. 7.

Figure 7:
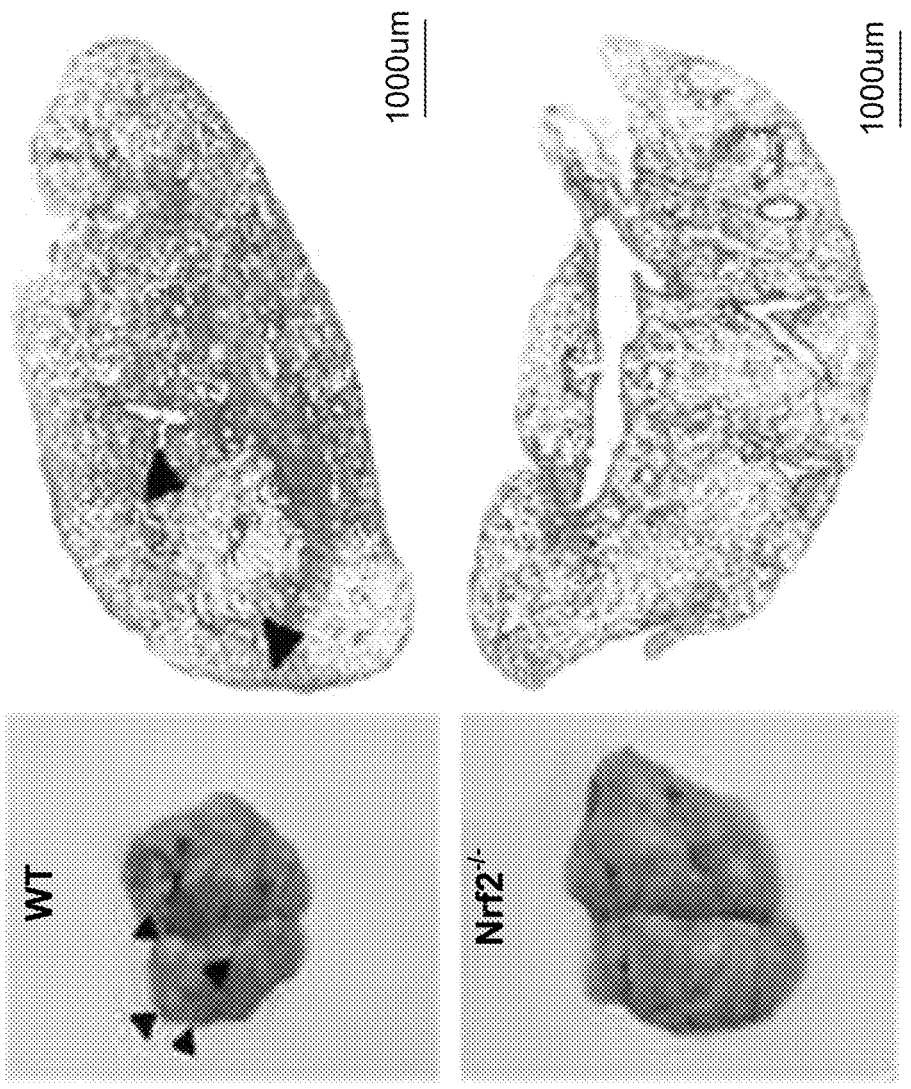
FIG. 7 shows an image of the cancer cell metastasis in the lung of wild-type and Nrf2−/− mice that changed with Nrf2 expression. The images to the left show photographic depiction of the lung tissue isolated from a representative wild-type (top) and Nrf2−/− (bottom) animals. The images to the right provide immunohistochemistry images of the lung tissues from wild-type (top) and Nrf2−/− (bottom) animals. Tumors are identified in the images with arrows.

As shown in FIG. 7, after injection of the lung carcinoma cells, noticeable tumor growth was observed in the lungs of wild-type animals, indicating that the administered tumor cells had spread to the lung tissues. In contrast, a significant effect of inhibiting cancer cell metastasis was observed in the Nrf2-deleted mouse.

The above results suggest the potential benefit of reducing Nrf2 expression in treating cancer.

Example 3. Determination of T Cell-Mediated Anticancer Reaction that Changed with Modulation of Nrf2 Expression 3-1. Determination of T Cell-Mediated Anticancer Reaction The Nrf2-deleted mouse would give strong anticancer reactions to various cancer cells, which was confirmed in the above-described example 2. In order to determine whether the above-described phenomenon was a T cell-mediated anticancer reaction, treatment was performed such that the Nrf2-deleted mouse and the wild-type mouse went into a T cell-deficient state. Specifically, anti-CD3 antibody was administered to deplete the T cells. Some of the animals from both the tumor-bearing wild-type and Nrf2-deleted animals received the anti-CD3 antibody (control animals received an IgG control antibody); then, the cancer cell proliferation was observed by measuring both the tumor volume and tumor weight at various time points post tumor inoculation. The result is shown in FIGS. 8A and 8B.

Figures 8A, 8B:
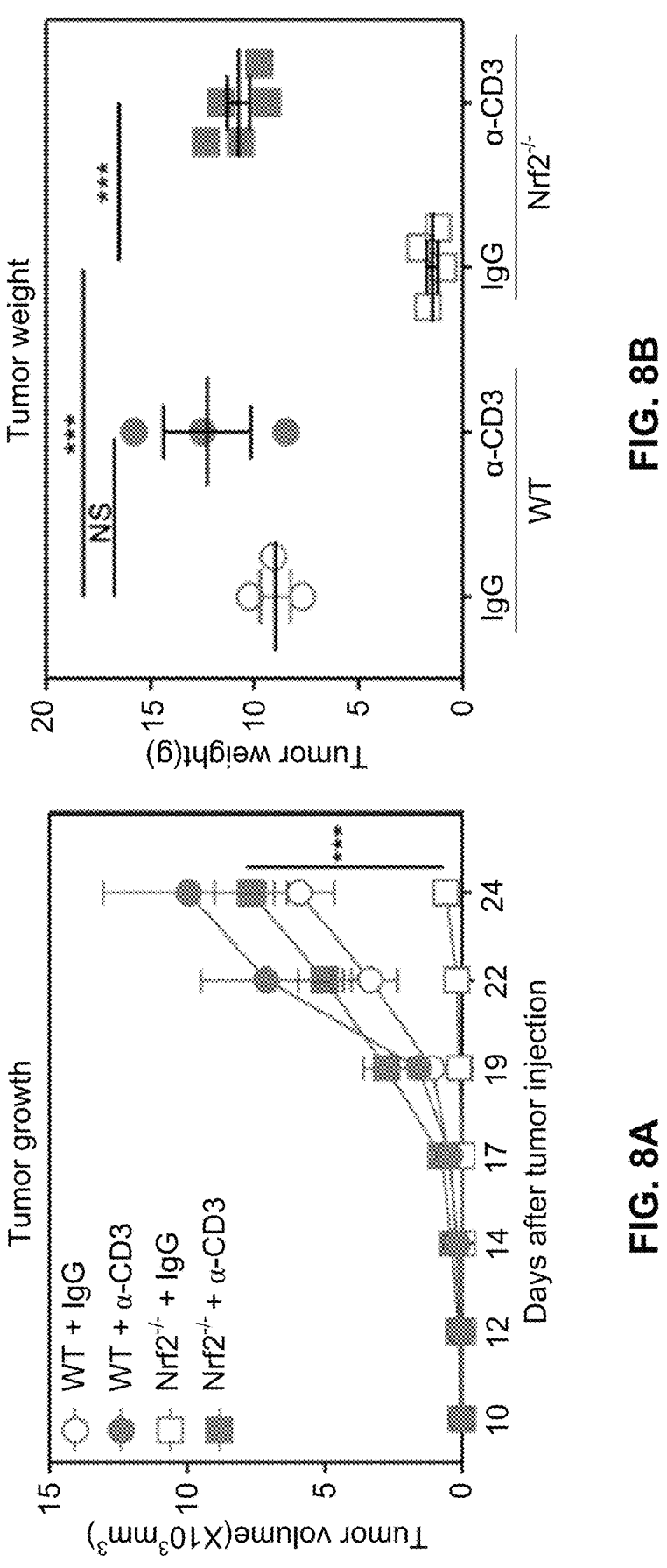
FIGS. 8A and 8B show T cell-mediated anti-tumor immune responses that changed with Nrf2 expression. Specifically.

As shown in FIGS. 8A and 8B, when the Nrf2-deleted mouse was in a T cell-deficient state, the effect of inhibiting cancer cell proliferation in the mouse had disappeared. The above-described results confirmed a close relationship between anticancer reaction and T cells during an Nrf2 deficiency.

Figures 9A, 9B:
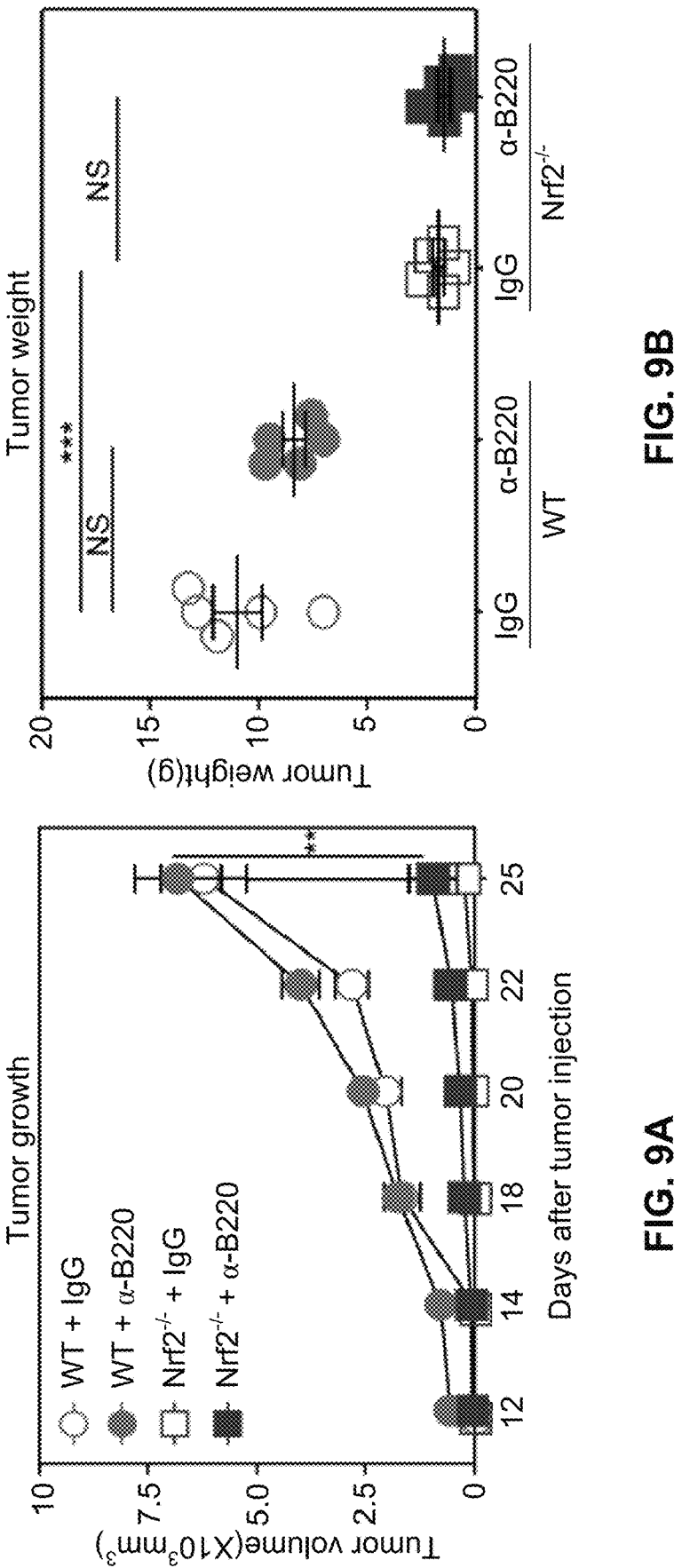
FIGS. 9A and 9B provide that the improved anti-tumor immune responses observed in the Nrf2−/− animals is not dependent on B cells. Comparison of tumor growth (FIG. 9A) and tumor weight (FIG. 9B) are provided for the following groups: (i) tumor-bearing wild-type animals that received a control IgG antibody ("WT+IgG" or "open circle"); (ii) tumor-bearing wild-type animals that received an administration of a B cell depleting anti-B220 antibody ("WT+α-B220" or "filled circle"); (iii) tumor-bearing Nrf2-/- animals that received a control IgG antibody ("Nrf2-/-+IgG" or "open square"); and (iv) tumor-bearing Nrf2-/- animals that received an administration of a B cell depleting anti-B220 antibody ("Nrf2-/-+α-B220" or "closed square").

To further confirm that the enhanced anti-tumor immune response observed in the Nrf2-deleted animals was T cell-mediated, anti-B220 antibody was used to deplete B cells in both tumor-bearing wild-type and Nrf2-deleted animals. As shown in FIGS. 9A and 9B, depletion of B cells had no effect on anti-tumor immune response. In the Nrf2-deleted animals, both the tumor volume and tumor weight was comparable in both animals that received the anti-B220 antibody and those that received the control IgG antibody.

The above results confirm that the anti-tumor immune response observed in the Nrf2-deleted animals was mediated primarily by T cells.

3-2. Determination of the Level of Cancer Toxic CD8 T Cell Activation Along with Changes in Nrf2 Expression To understand how the deletion of Nrf2 affects T cell function, the level of cancer toxic CD8 T cell activation that changed along with changes in Nrf2 expression was observed, thereby confirming the relationship between the level of cancer toxic CD8 T cell activation and anticancer reaction. Specifically, CD4+ T cells and CD8+ T cells were isolated from tumor-bearing wild-type and Nrf2-deleted animals. The cells were isolated from either the tumor (i.e., TILs) or from the draining lymph nodes. Then, the T cells were TCR stimulated and the amount of IFN-γ and IL-17 produced were measured. The result is shown in FIG. 10.

Figure 10:
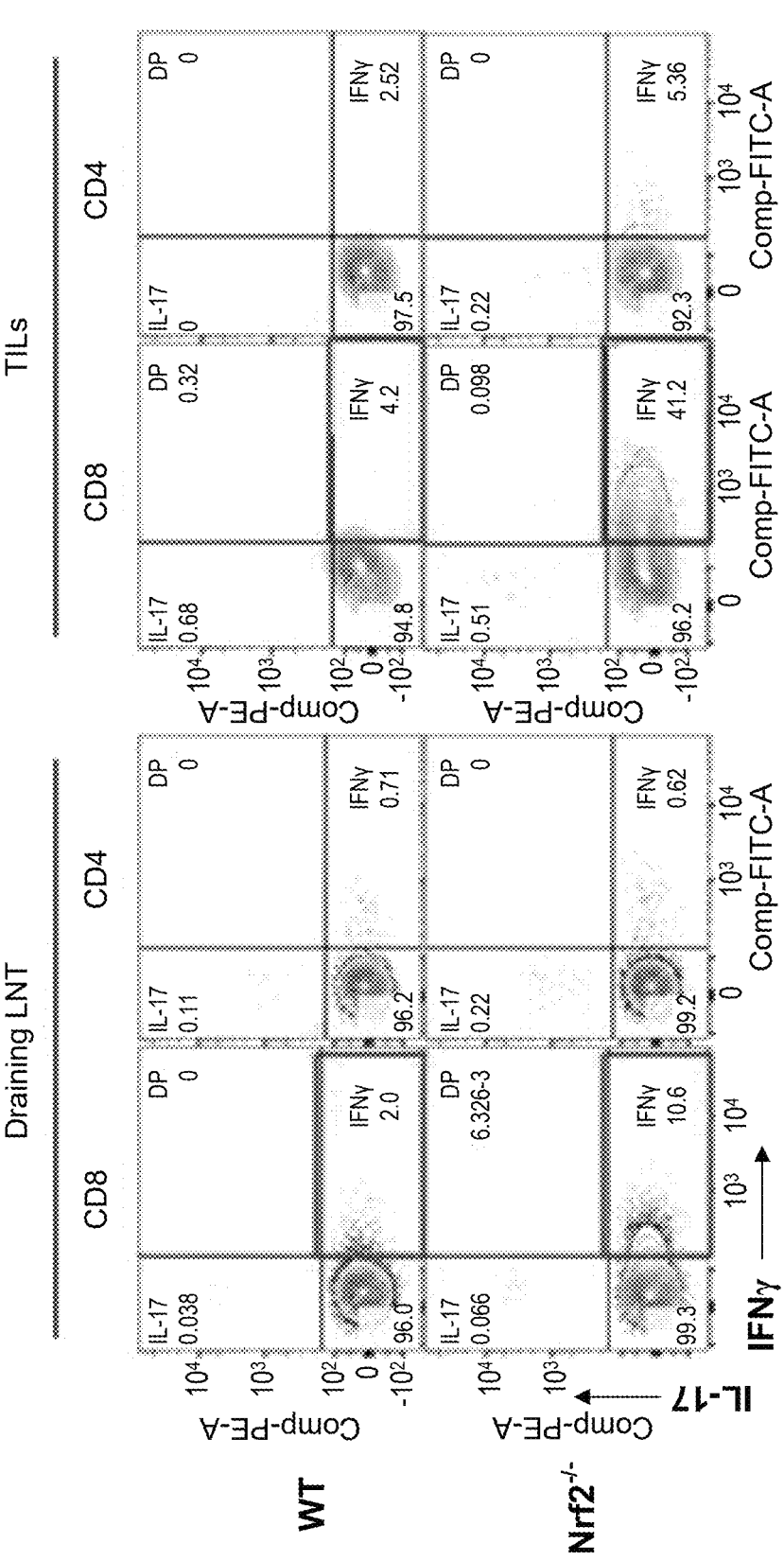
FIG. 10 shows a T cell activity that changed with Nrf2 expression. Specifically, FIG. 10 provides a comparison of IL-17 (y-axis) and IFN-γ (x-axis) production by draining lymph node T cells ("Draining LNT") and TILs isolated from tumor-bearing wild-type (top) and Nrf2-/- (bottom) animals. The two different categories of T cells are further divided based on their CD4 and CD8 expression.

As shown in FIG. 10, a significant increase in the amount of IFNγ secreted by the cancer cytotoxic CD8 T cells was observed in the Nrf2-deleted mouse. No significant differences were observed among CD4+ T cells. The increase in IFN-γ production was observed in both CD8+ T cells isolated from the draining lymph nodes and the tumors. However, the difference was much more dramatic for CD8+ TILs. The above-described result confirmed the ability of Nrf2 to reversely and deeply interfere with T cell responsiveness and activity.

3-3. Determination of the Anticancer Efficacy of Cancer Toxic CD8 T Cells on an In Vivo Model Based on the 3-1 and 3-2 results obtained in the above-described examples, the anticancer efficacy of cancer toxic CD8 T cells on an in vivo mouse model was determined. Specifically, OVA antigen-specific CD8 T cells (OT-I cells) subjected to Nrf2 expression deficiency treatment were injected into a mouse in which cancer cells were transplanted (for expressing the OVA antigen), and then the effect of cancer cell inhibition was observed. As controls, T cells from wild-type and Nrf2+/− animals were isolated and administered to the wild-type tumor bearing animals. The result is shown in FIG. 11.

Figure 11:
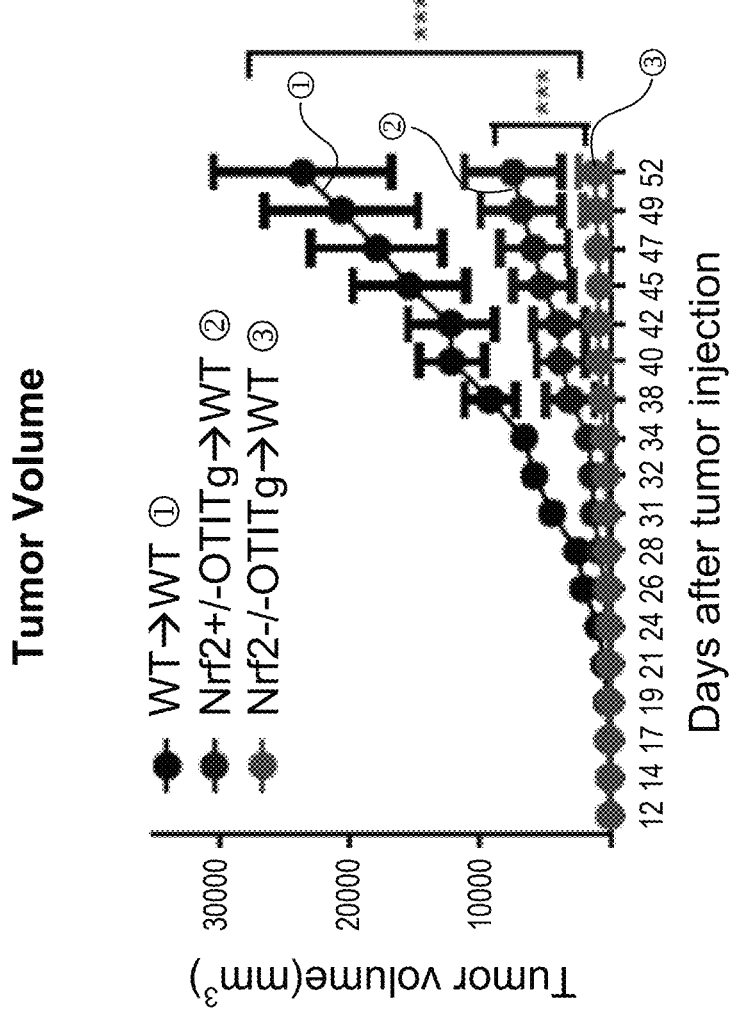
FIG. 11 shows the anticancer efficacy of Nrf2-deleted toxic CD8+ T cells in adoptive transfer model. Specifically, OVA-specific CD8+ T cells from wild-type, Nrf2+/-, or Nrf2-/- mice were isolated and adoptively transferred into wild-type animals that were inoculated with EG7-OVA tumor cells. The different treatment groups are as follows: (1) WT cells into WT mice; (2) Nrf2+/- cells into WT mice; and (3) Nrf2-/- cells into WT mice.
Figure 12:
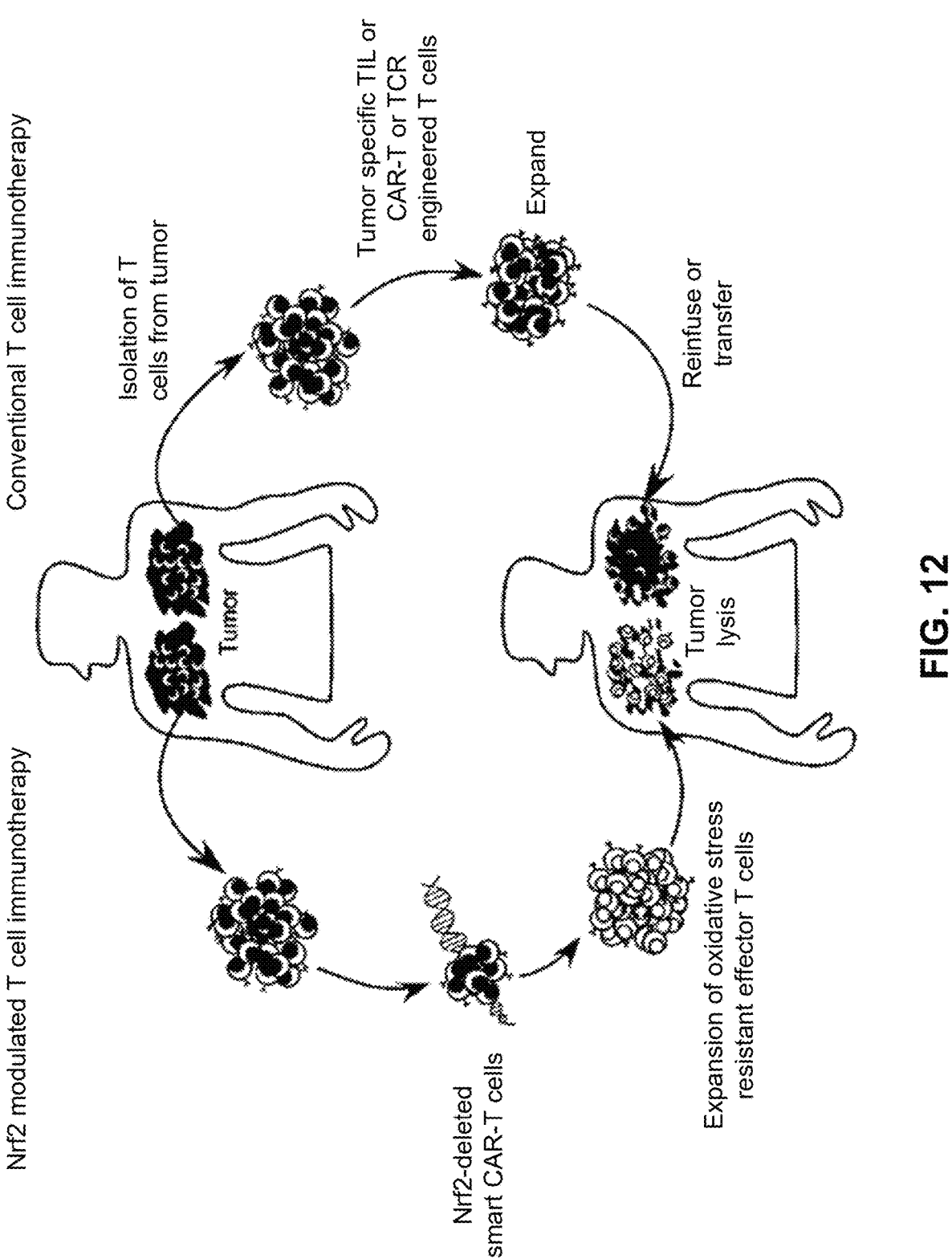
FIG. 12 shows a schematic drawing for the flow of the present disclosure, namely, a tumor immunotherapy that involves the modulation of Nrf2 expression in cytotoxic CD8+ T cells.
Figure 14A:
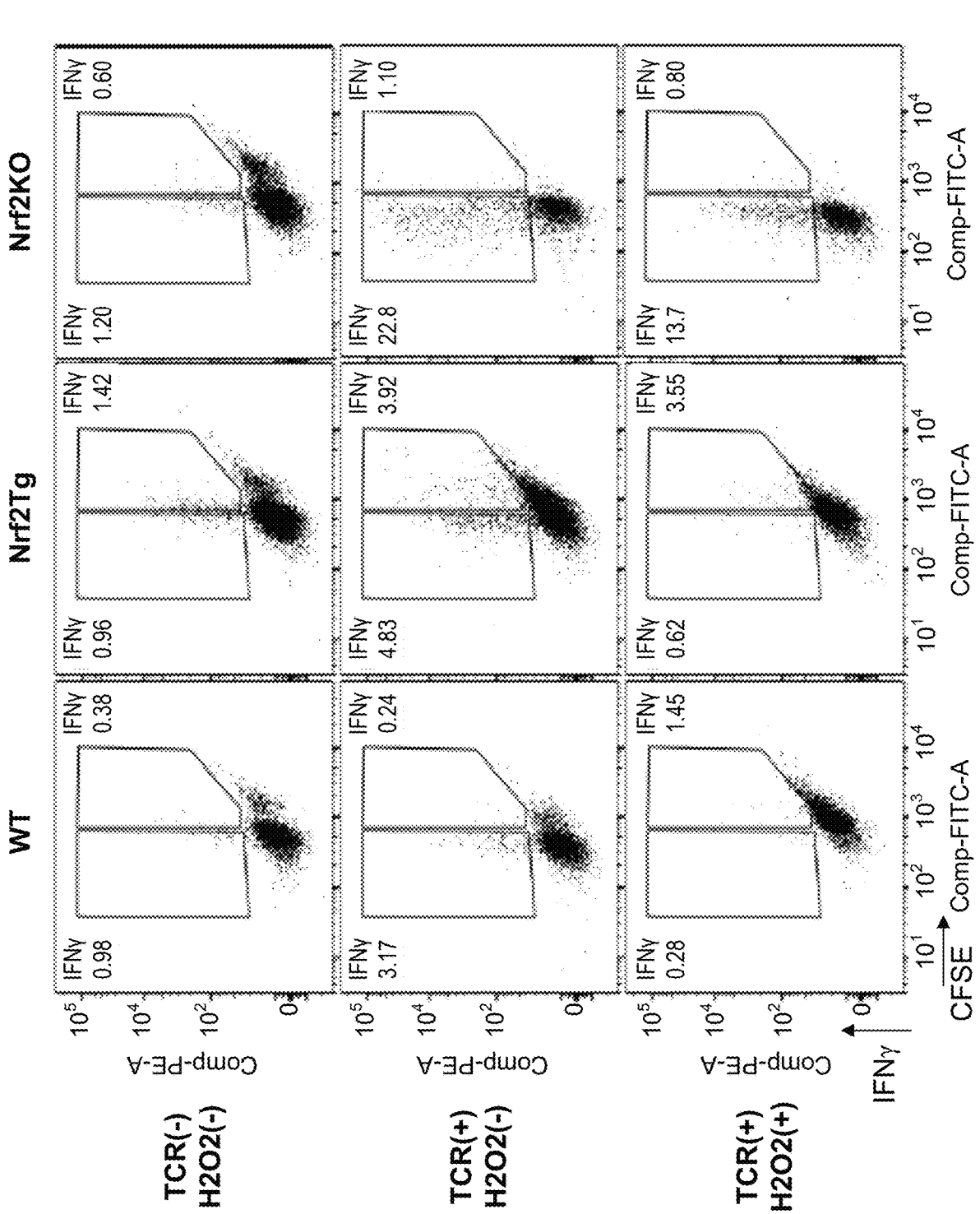
FIGS. 14A, 14B, 14C, and 14D show the function of T cells isolated from wild-type (left column, "WT"), Nrf2-transgenic (middle column, "Nrf2Tg"), and Nrf2-/- (right column, "Nrf2KO") animals to resist oxidative stress (OS) provided in the presence of hydrogen peroxide ($H_2O_2$).
Figure 14B:
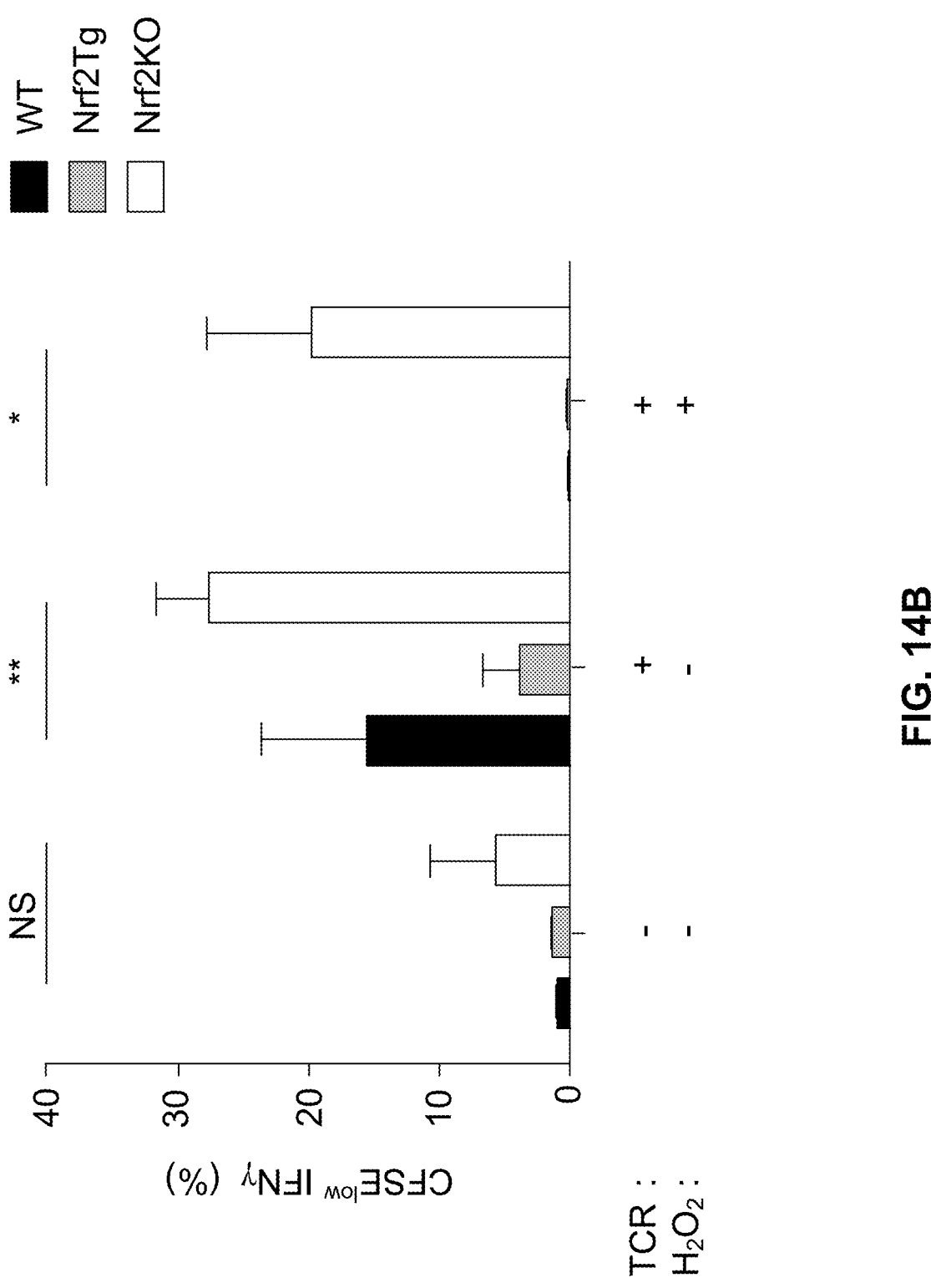
Figure 14C:
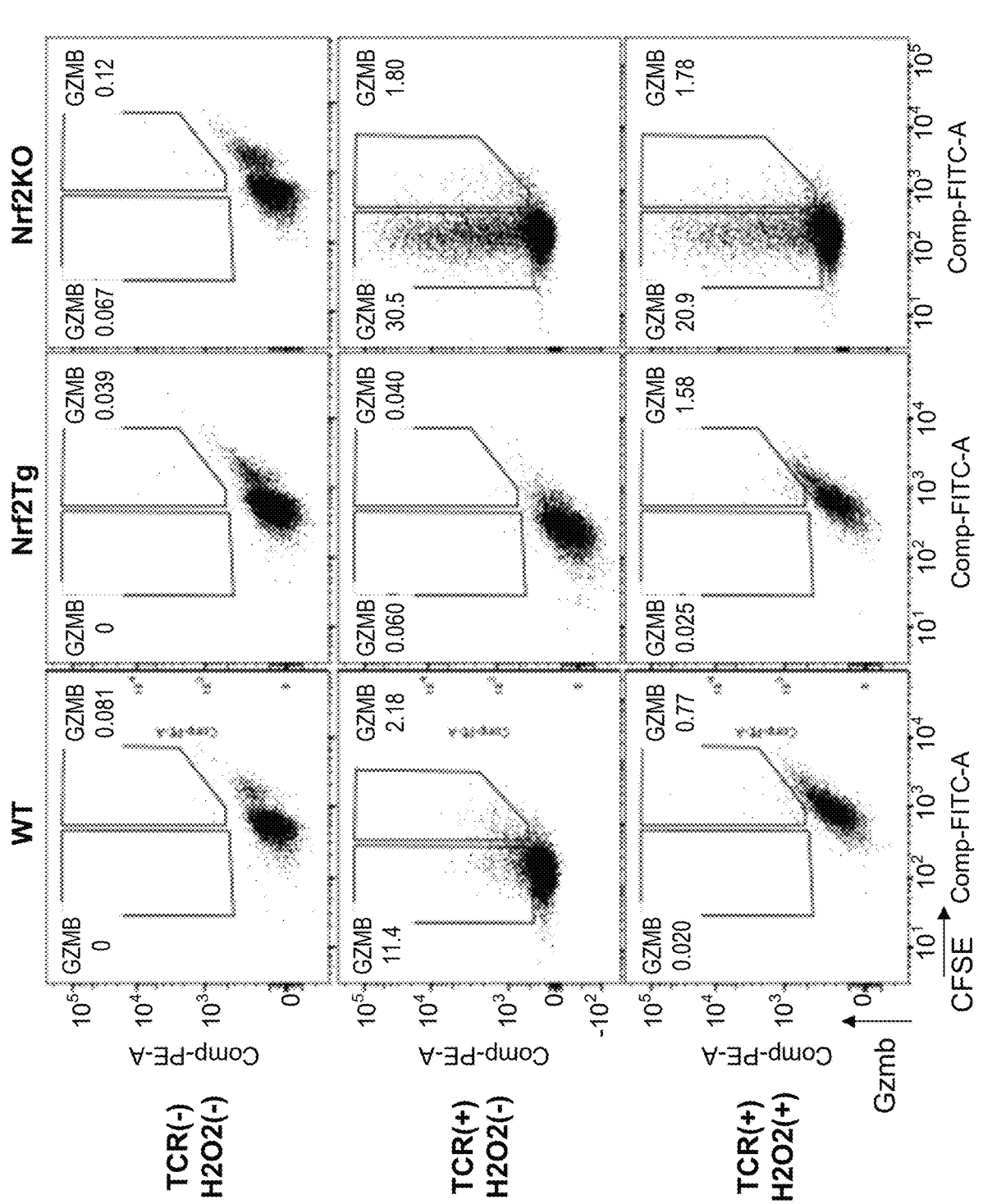
Figure 14D:
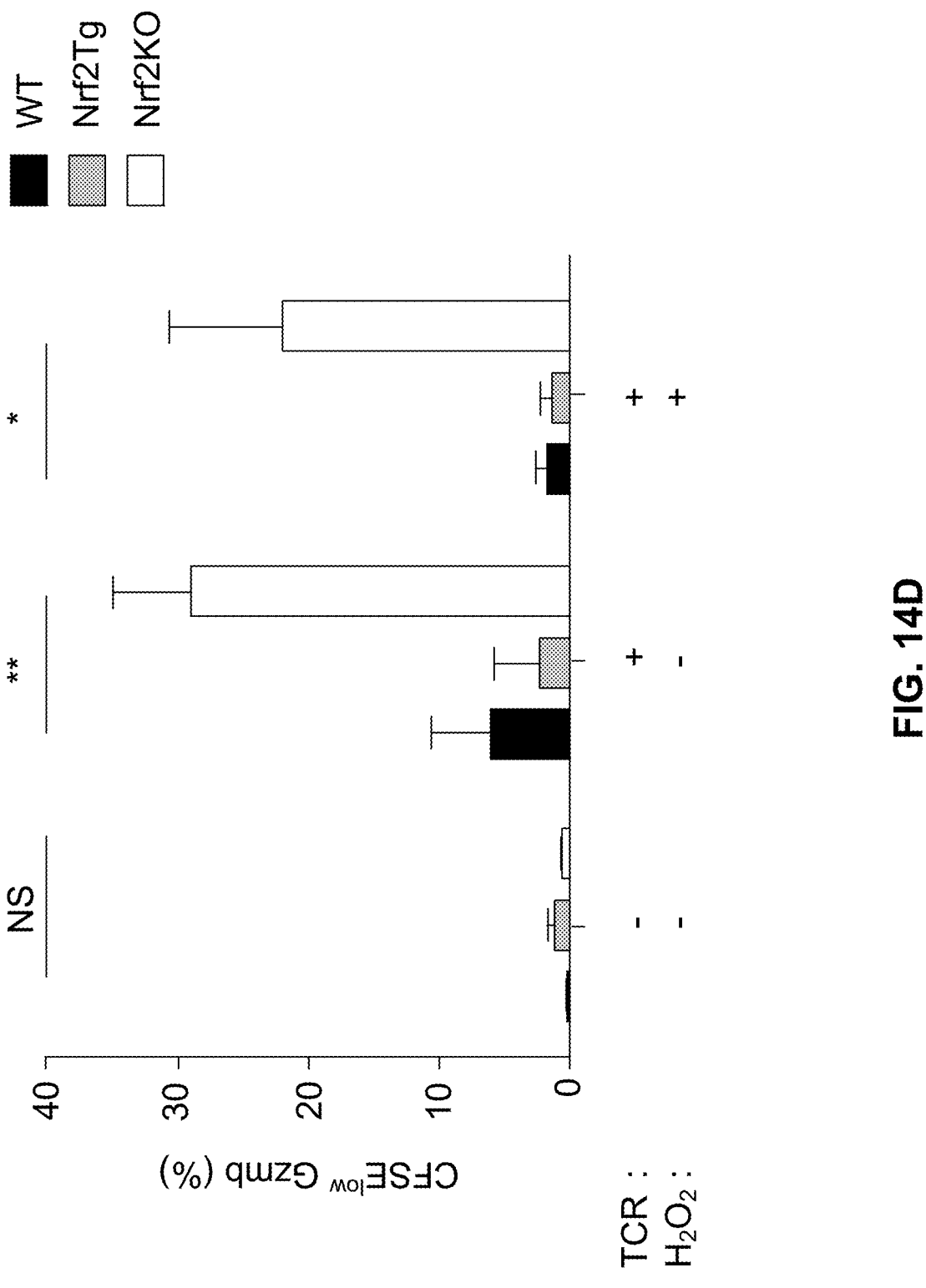

As shown in FIG. 11, a significant effect of cancer cell inhibition was observed in the mouse in which Nrf2-deleted-specific CD8 T cells (OT-I cells) were injected. An intermediate effect was observed when T cells from Nrf2+/− animals were used for the adoptive transfer. The above-described result confirmed that Nrf2 expression is able to decrease the responsiveness of CD8 T cells, performing counteraction (inverse interference) in inhibition of cancer cell proliferation.

Example 4: Further Analysis of the Relationship Between Nrf2 Expression and Anti-Tumor Immune Response To further confirm the results observed in the above examples, MC38 (colorectal) tumor cells were administered to the following animals: (i) wild-type; (ii) Nrf2-deleted; and (iii) transgenic mice overexpressing Nrf2 ("Nrf2Tg"). Then, as described in the earlier examples, the anti-tumor immune response in the different groups was observed by measuring tumor volume at various time points post tumor inoculation.

Figures 13A, 13B:
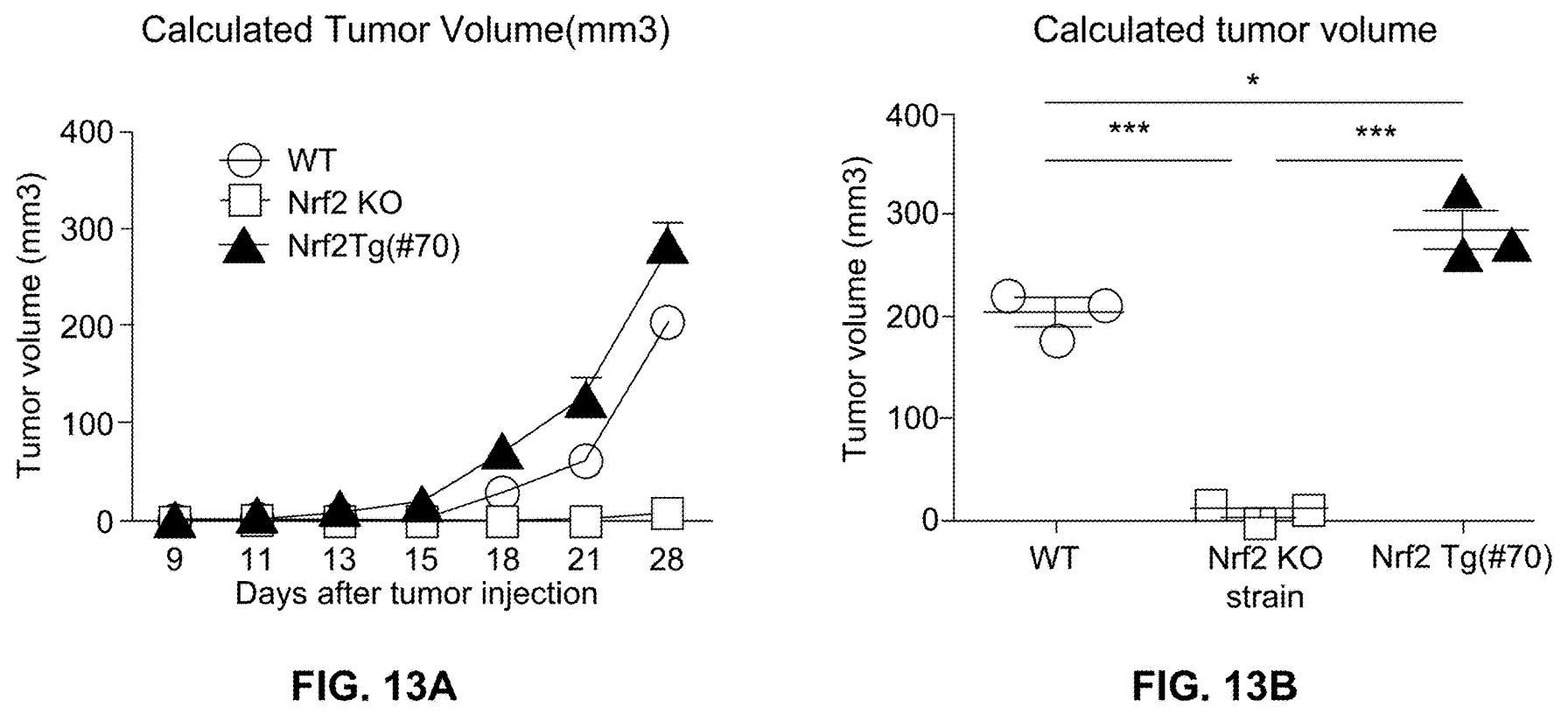

As shown in FIGS. 13A and 13B, the deletion of Nrf2 expression also improved the anti-tumor immune response against colorectal tumor cells. This result further confirms that reducing Nrf2 expression can have therapeutic benefits against many different cancer types. Moreover, the above data suggests that the ability of T cells to treat tumors is inversely proportional to the Nrf2 expression. For instance, in the Nrf2-transgenic animals, tumor volume was even greater than the wild-type animals.

Example 5: Analysis of the Resistance of Nrf2-Deleted T Cells to Oxidative Stress To identify potential mechanisms by which T cells from Nrf2-deleted animals can mount a more effective anti-tumor immune response, the ability of the T cells from wild-type, Nrf2-transgenic, and Nrf2-deleted animals to produce IFN-γ and granzyme B upon TCR stimulation was measured both in the presence and absence of hydrogen peroxide.

As shown in FIGS. 14A-14D, only T cells from the Nrf2-deleted animals were able to produce IFN-γ and granzyme B in the presence of hydrogen peroxide. This result suggests that the T cells in the Nrf2-deleted animals remain functional and are more resistant to oxidative stress induced in many cancer types.

Example 6: Construction of a CAR T Cell with Reduced Nrf2 Expression

Figure 15A:
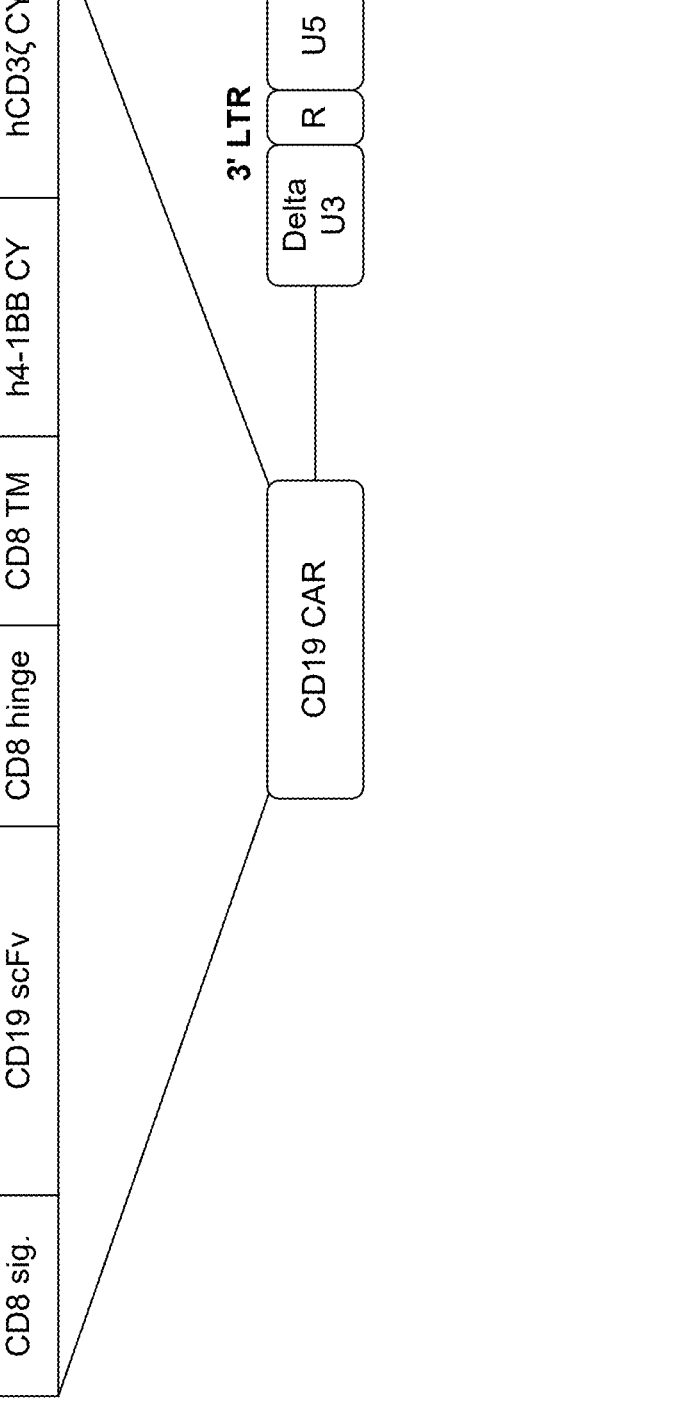
Figures 15B, 15C:
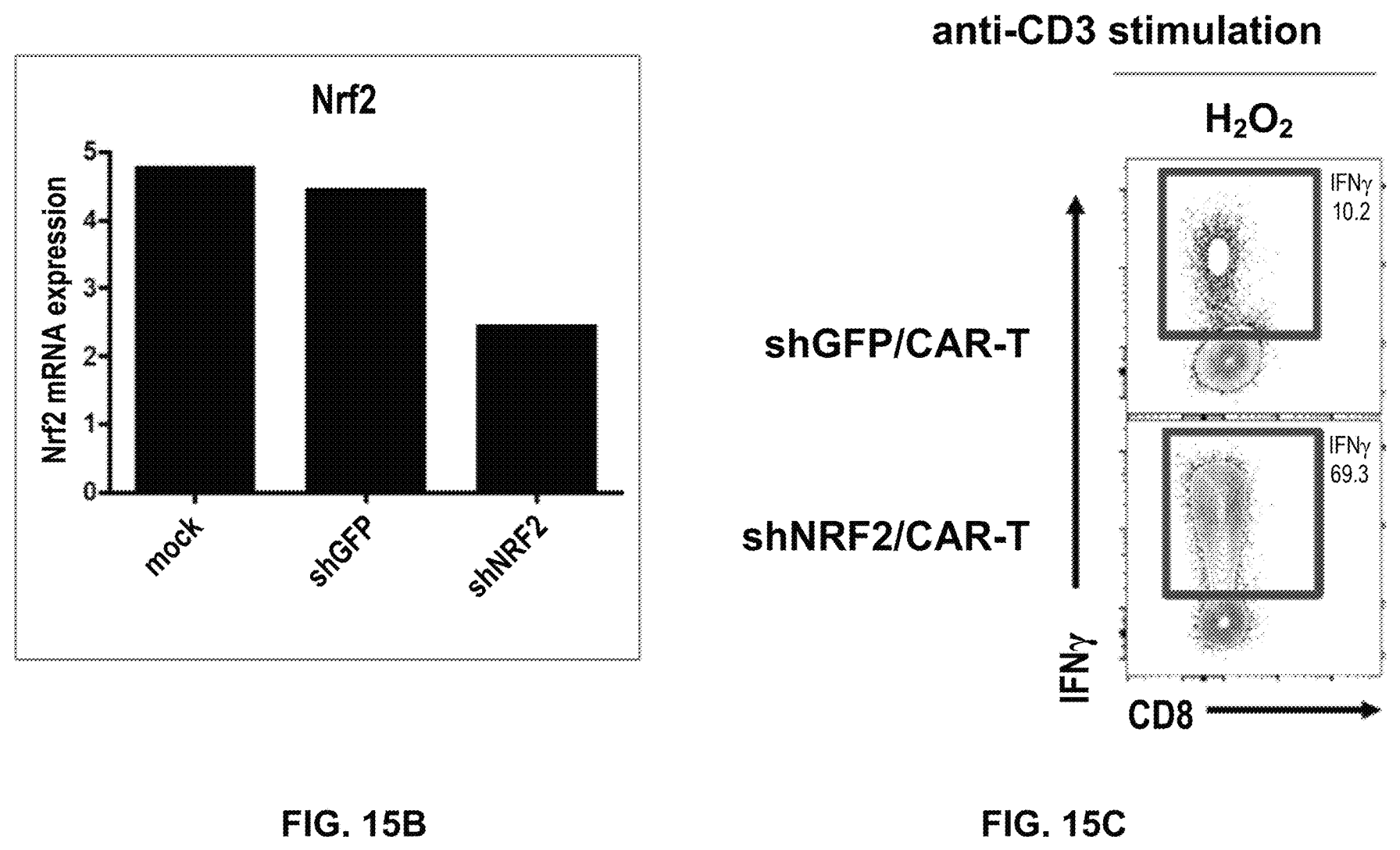

The above results confirm the potential benefit of using Nrf2-deleted T cells to treat cancer. In the pursuit of developing such immunotherapy, CD19-specific CAR T cells with reduced Nrf2 expression was constructed. FIG. 15A provides a schematic of the construct used to generate the CAR T cells. FIG. 15B provides that using the construct provided in FIG. 15A, CD19-specific CAR T cells were generated, where the Nrf2 mRNA expression was reduced by about 50%. Even with only a 50% reduction, as shown in FIG. 15C, the CAR T cells exhibited improved resistance to oxidative stress. Compared to the control CAR T cells that expressed normal levels of Nrf2, significantly greater percentage of the CAR T cells with reduced Nrf2 expression produced IFN-γ in the presence of hydrogen peroxide.

Figures 16A, 16B, 16C:
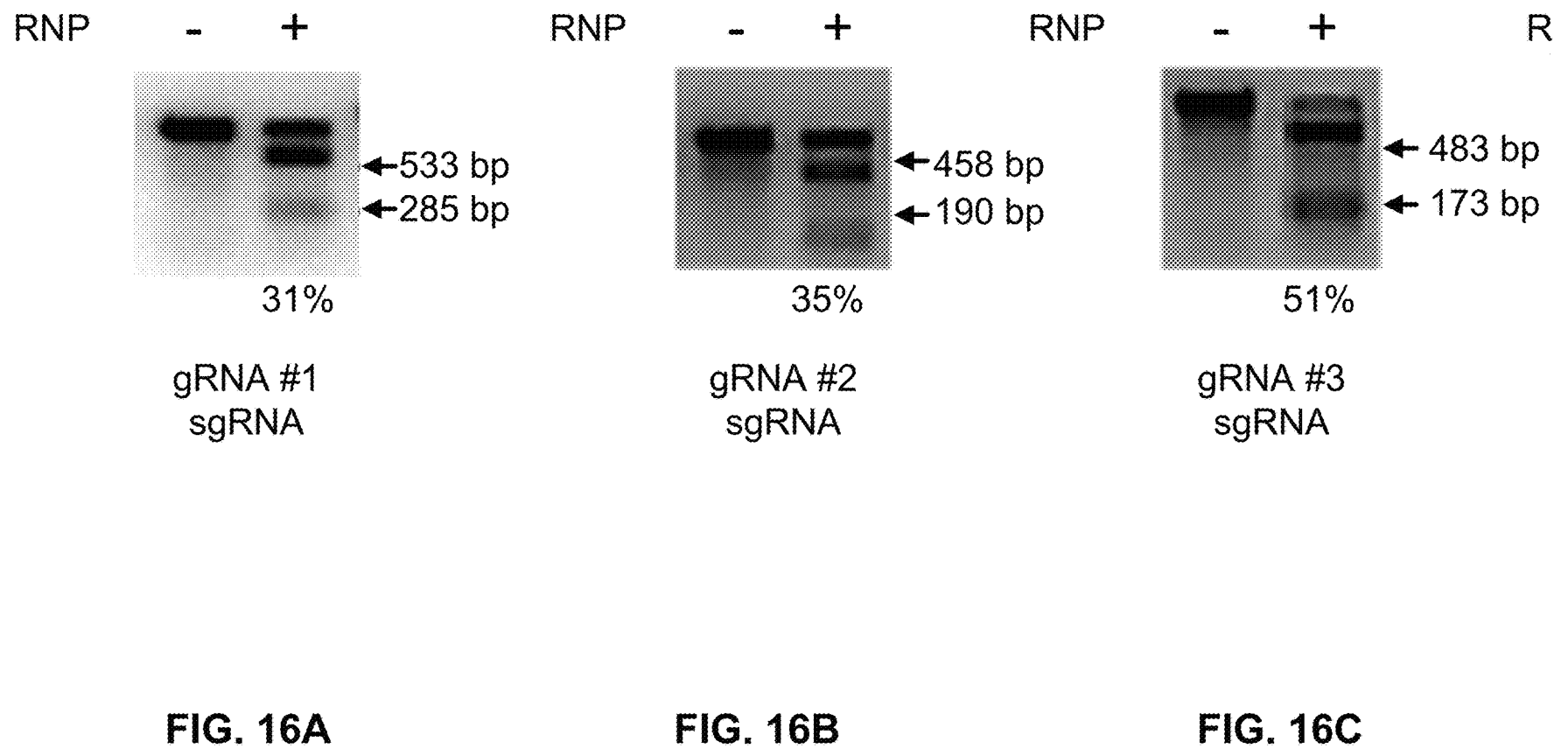

Next, to identify other methods of reducing Nrf2 expression in T cells (e.g., CAR T cells), CRISPR/Cas9 system was used. FIGS. 16A, 16B, and 16C provide the results using three different guide RNAs that target Nrf2. Table 3 (below) provides the number of mutations, insertions, and deletions that were observed using the different guide RNAs. As shown, Nrf2 deficient human T cells were successfully generated with 83% efficacy using CRISPR/Cas9 system (specifically guide RNA identified as "Sg3").

TABLE 3

| Target | Total Counts | Mutated Counts | Insertions | Deletions | Insertion/deletion Frequency |
|--------|-------------|----------------|------------|-----------|------------------------------|
| Sg1 | 25378 | 5 | 0 | 5 | 5 (0.0%) |
| | 37365 | 24661 | 76 | 24585 | 24661 (66%) |
| Sg2 | 35691 | 2 | 0 | 2 | 2 (0.0%) |
| | 29936 | 9000 | 335 | 8665 | 9000 (30.1%) |
| Sg3 | 47543 | 8 | 0 | 8 | 8 (0.0%) |
| | 27186 | 22649 | 2879 | 19770 | 22649 (83.3%) |

Collectively, the above results demonstrate that CAR-expressing cells, such as CAR T cells, with reduced Nrf2 expression could be a viable treatment options for many different cancers.

---

What is claimed is:

1. A method of treating a tumor in a subject in need thereof, comprising administering to the subject a modified cell which expresses a reduced expression level of a NFE2L2 gene and/or a protein encoded thereof, compared to a corresponding non-modified cell, wherein the modified cell comprises a chimeric antigen receptor (CAR) and/or a T cell receptor (TCR).

2. The method of claim 1, wherein the expression level of the NFE2L2 gene and/or protein encoded thereof is reduced by at least about 50%, compared to the corresponding non-modified cell.

3. The method of claim 1, wherein after the administration: (i) a tumor volume in the subject is reduced, (ii) a tumor weight in the subject is reduced, (iii) one or more properties of a tumor-infiltrating lymphocyte (TIL) in the subject is improved, or (iv) any combination of (i)-(iii).

4. The method of claim 1, wherein the modified cell exhibits increased resistance to oxidative stress compared to the corresponding non-modified cell.

5. The method of claim 1, wherein the modified cell comprises a T cell, tumor-infiltrating lymphocyte (TIL), lymphokine-activated killer cell, natural killer (NK) cell, or any combination thereof.

6. The method of claim 5, wherein the T cell is a CD8+ T cell, CD4+ T cell, NKT cell, or a combination thereof.

7. A method of preparing an immune cell for chimeric antigen receptor (CAR) and/or T cell receptor (TCR) engineering comprising contacting the immune cell with a gene editing tool which is capable of reducing an expression level of a NFE2L2 gene and/or protein encoded thereof, and, further comprising modifying the immune cell to express a CAR and/or a TCR.

8. The method of claim 7, wherein, after the contacting, the expression level of the NFE2L2 gene and/or protein encoded thereof is reduced by at least about 50%, compared to a corresponding immune cell that was not contacted with the gene editing tool.

9. The method of claim 7, wherein the immune cell comprises a T cell, tumor-infiltrating lymphocyte (TIL), lymphokine-activated killer cell, natural killer (NK) cell, or any combination thereof.

10. The method of claim 7, wherein the gene editing tool comprises a shRNA, siRNA, miRNA, antisense oligonucleotides, CRISPR, zinc finger nuclease, TALEN, meganuclease, restriction endonuclease, or any combination thereof.

11. A CAR and/or TCR-expressing immune cell prepared by the method of claim 7.

12. A pharmaceutical composition comprising the CAR and/or TCR-expressing immune cell of claim 11.

* * * * *